US009645498B2

(12) United States Patent
Hatakeyama

(10) Patent No.: US 9,645,498 B2
(45) Date of Patent: May 9, 2017

(54) DEVELOPER AND PATTERNING PROCESS USING THE SAME
(71) Applicant: SHIN-ETSU CHEMICAL CO., LTD., Tokyo (JP)
(72) Inventor: Jun Hatakeyama, Jyoetsu (JP)
(73) Assignee: SHIN-ETSU CHEMICAL CO., LTD., Tokyo (JP)
( * ) Notice: Subject to any disclaimer, the term of this patent is extended or adjusted under 35 U.S.C. 154(b) by 0 days.
(21) Appl. No.: 14/949,418
(22) Filed: Nov. 23, 2015
(65) Prior Publication Data
US 2016/0195813 A1 Jul. 7, 2016
(30) Foreign Application Priority Data Jan. 5, 2015 (JP) ................................. 2015-000196

(51) Int. Cl.
G03F 7/32 (2006.01)
C07C 211/63 (2006.01)
G03F 7/004 (2006.01)
C07C 381/12 (2006.01)
C08F 220/18 (2006.01)
C08F 220/38 (2006.01)
C08F 220/22 (2006.01)
C08F 220/30 (2006.01)
H01L 21/027 (2006.01)
G03F 7/039 (2006.01)
G03F 7/20 (2006.01)
C07C 219/16 (2006.01)

(52) U.S. Cl.
CPC ............ G03F 7/322 (2013.01); C07C 211/63 (2013.01); C07C 219/16 (2013.01); C07C 381/12 (2013.01); C08F 220/18 (2013.01); C08F 220/22 (2013.01); C08F 220/30 (2013.01); C08F 220/38 (2013.01); G03F 7/004 (2013.01); G03F 7/0045 (2013.01); G03F 7/0046 (2013.01); G03F 7/0397 (2013.01); G03F 7/2041 (2013.01); G03F 7/32 (2013.01); G03F 7/325 (2013.01); H01L 21/0274 (2013.01)

(58) Field of Classification Search
CPC . G03F 7/004; G03F 7/325; G03F 7/32; G03F 7/20; C08F 220/18; C08F 220/22; C08F 220/30; C08F 220/38; C07C 381/12; C07C 211/62; C07C 211/63; H01L 21/0274
USPC .... 430/270.1, 322, 325, 329, 330, 331, 434, 430/435; 564/286, 291, 295; 526/281, 526/286, 242, 319, 326
See application file for complete search history.

(56) References Cited

U.S. PATENT DOCUMENTS 4,833,067 A * 5/1989 Tanaka ..................... G03F 7/322
430/309
5,575,901 A * 11/1996 Hulme ................... C07C 209/68
204/522
5,576,459 A * 11/1996 Osborn ................... C07C 51/412
562/553
6,448,420 B1 9/2002 Kinsho et al.
6,727,387 B2 * 4/2004 Mukkamala ............ A01N 33/12
254/390
7,214,806 B2 * 5/2007 Lang ...................... C07C 217/42
210/700
8,703,384 B2 * 4/2014 Kobayashi ............ G03F 7/0045
430/270.1
8,835,687 B2 * 9/2014 Kim ....................... C07C 201/12
564/414
2002/0081521 A1 6/2002 Takeda et al.
2002/0106589 A1 * 8/2002 Rodney .................. C07C 43/178
430/325
2007/0231708 A1 10/2007 Matsumaru et al.
2008/0090172 A1 4/2008 Hatakeyama et al.
2008/0118860 A1 5/2008 Harada et al.
2008/0161217 A1 * 7/2008 Zhang ..................... G03F 7/426
510/176
2008/0241736 A1 10/2008 Kobayashi et al.
2009/0202943 A1 * 8/2009 Ohsawa ................. G03F 7/0045
430/285.1
2009/0233223 A1 * 9/2009 Tachibana ............ G03F 7/0045
430/270.1

FOREIGN PATENT DOCUMENTS

| CA | 2049772 A1 | 2/1992 |
|---|---|---|
| JP | H04-230645 A | 8/1992 |
| JP | 2000-327633 A | 11/2000 |
| JP | 2005-084365 A | 3/2005 |
| JP | 2006-045311 A | 2/2006 |
| JP | 2006-169302 A | 6/2006 |
| JP | 3865048 B2 | 1/2007 |
| JP | 2008-111103 A | 5/2008 |
| JP | 2008-122932 A | 5/2008 |
| JP | 2008-239918 A | 10/2008 |
| JP | 2012208325 A * | 10/2012 |

* cited by examiner

Primary Examiner — Amanda C Walke
(74) Attorney, Agent, or Firm — Oliff PLC

(57) ABSTRACT

The present invention provides a developer for a photosensitive resist composition, comprising a compound represented by the general formula (1)

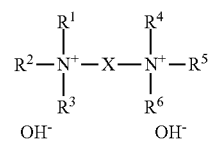

wherein $R^1$ to $R^6$ represent a linear, branched, or cyclic alkyl group having 1 to 4 carbon atoms; and X represents a linear or branched alkylene group having 6 to 16 carbon atoms and optionally having an ester group. There can be provided a developer that can prevent the occurrence of pattern collapse and connection between patterns, i.e. bridge defect after development and can provide a resist pattern with small edge roughness.

20 Claims, No Drawings ial hydroxide (TMAH) developer, hydrophobicity of a polymer is enhanced; however, a hydrophobic polymer causes the problem of bad affinity with the TMAH developer which is a water-soluble alkaline developer.

DEVELOPER AND PATTERNING PROCESS USING THE SAME

BACKGROUND OF THE INVENTION

Field of the Invention

The present invention relates to a developer suitably used for development of a photosensitive resist composition, particularly a chemically amplified positive resist composition, and to a patterning process using the same.

Description of the Related Art

As LSI advances toward higher integration and high processing speed, miniaturization of pattern rule is progressing rapidly. Especially, the expansion of the flash memory market and the increase in memory capacity lead this miniaturization. As the cutting-edge technology for miniaturization, the 65-nm node device is being mass-produced by an ArF lithography; and mass-production of the 45-nm node by an ArF immersion lithography as the next generation technology is under preparation. A candidate for the next generation 32-nm node that is under investigation includes: the immersion lithography by a super high NA lens formed of a combination of a liquid having a higher refractive index than water, a lens having a high refractive index, and a resist film having a high refractive index; a lithography by a vacuum ultraviolet (EUV) with a wavelength of 13.5 nm; and a double exposure of an ArF lithography (double patterning lithography).

A high energy beam having extremely short wavelength, such as electron beam (EB) and X-ray, is hardly absorbed into a composition such as a hydrocarbon used in a resist composition, so that a resist composition based on polyhydroxystyrene is under investigation. The resist composition for EB has been practically used for drawing a mask, but some problems recently arise in a technique for manufacturing a mask. For example, a reduction projection exposure apparatus having a reduction rate of ⅕ has been used since the age when g-beam is used as the exposure light, however, as the chip size and the diameter of the projection lens increase, the reduction rate shifts to ¼, which causes the problem that a dimensional deviation of a mask affects a dimensional change of a pattern on a wafer. In this context, it is pointed out that as a pattern becomes finer, a dimensional deviation on a wafer tends to be larger than a dimensional deviation of a mask; and thus, Mask Error Enhancement Factor (MEEF) is calculated from a dimensional change of a mask as the denominator and a dimensional change on a wafer as the numerator. In a 45-nm pattern, MEEF often exceeds 4. When the reduction rate is ¼ and MEEF is 4, accuracy equivalent to an unmagnified mask is substantially required for mask production.

As to the exposure apparatus for mask production, an exposure apparatus using laser beam or EB has been used to enhance line-width accuracy. Moreover, increasing the acceleration voltage of an electron beam gun enables further miniaturization; and thus, the acceleration voltage has been increased from 10 keV to 30 keV, and 50 keV with the recent main stream, and further study of 100 keV is taking place.

Note that, deterioration in sensitivity of the resist film is becoming a problem as the acceleration voltage is increased. As the acceleration voltage is increased, the forward scattering effect within the resist film becomes smaller, so that contrast of the electron beam drawing energy is enhanced thereby leading to improvement in resolution and size controllability, while sensitivity of the resist film is deteriorated because the electron passes through the resist film with free draining condition. In the exposure apparatus for mask production, direct drawing is done by way of a one-stroke sketch, so that the deterioration in sensitivity of the resist film causes the decrease in productivity; and thus, this is not desirable. Accordingly, a resist film with higher sensitivity is required, and investigation of a chemically amplified resist composition is getting underway.

In addition, with the miniaturization of a pattern of the EB lithography for mask production, thinning of the resist film is progressing in order to prevent pattern collapse during development due to a high aspect ratio. In the photolithography, thinning of the resist film significantly contributes to enhancement of the resolution. This is because a device became more flattened by introduction of CMP and others. In mask production, a substrate is flat, so that film thickness of the resist film formed on the substrate to be processed (e.g., Cr, MoSi, and $SiC_2$) is determined on the basis of the light shielding rate and the phase difference control. To make the film thinner, dry etching resistance of the resist film needs to be enhanced.

Generally, it is said that there is a relationship between the carbon density and the dry etching resistance of the resist film. In the EB drawing, which is not influenced by absorption, the resist composition based on a novolac polymer having a high etching resistance has been developed. An indene copolymer shown in Patent Document 1 and an acenaphthylene copolymer shown in Patent Document 2 not only have high carbon density but also show an enhanced etching resistance by rigid main chain structures due to the cycloolefin structures.

It has been reported that a soft X-ray exposure having a wavelength of 5 to 20 nm (EUV) is less absorbed by carbon atoms. The increase of carbon density is effective to enhance not only the dry etching resistance but also the transmittance at the range of the soft X-ray wavelength.

With the progress of pattern miniaturization, there arise the problem of blur of the figure due to acid diffusion. For ensuring the resolution of a fine pattern with a dimensional size of 45 nm or less, the control of acid diffusion is important besides the enhancement of the dissolution contrast, which has been conventionally suggested. However, in a chemically amplified resist composition, sensitivity and contrast are increased by acid diffusion, so that if the acid diffusion is extremely controlled by reducing the post exposure bake (PEB) temperature and time, the sensitivity and the contrast are significantly decreased. There is a close relationship between the kind of an acid-labile group and the acid diffusion distance, and thus, it is desired to develop an acid-labile group that advances the deprotection reaction at an extremely short acid diffusion distance.

On the other hand, the trade-off relationship has been reported among the sensitivity, edge roughness, and resolution. When the sensitivity is increased, the edge roughness and the resolution are deteriorated, and when acid diffusion is controlled, the edge roughness and the sensitivity are decreased although the resolution is enhanced. With regard to this, addition of an acid generator capable of generating bulky acid is effective to control acid diffusion, but the control of acid diffusion leads to the reduction in edge roughness and sensitivity, as mentioned above. Thus, it has been suggested to copolymerize the polymer with an acid generator of an onium salt having a polymerizable olefin. Patent Documents 3 to 5 describe a sulfonium salt and an iodonium salt having a polymerizable olefin, capable of generating a specific sulfonic acid. The photoresist using a base polymer copolymerized with a polymerizable acid generator can reduce edge roughness and simultaneously enhance both properties of resolution and edge roughness since acid diffusion is small and the acid generator is uniformly dispersed into the polymer.

Moreover, the EUV lithography has severe problems of pattern collapse and bridge defect. These problems are supposed to be caused by swelling of the resist film in a developer. To reduce the swell in an aqueous tetramethylammonium hydroxide (TMAH) solution, a developer of an aqueous tetrabutylammonium hydroxide (TBAH) solution has been investigated, but it is still inadequate for a pattern formation of 20 nm or less. Therefore, it has been desired to develop a further developer that can prevent swelling.

PRIOR ART DOCUMENTS

Patent Documents

Patent Document 1: Japanese Patent No. 3865048
Patent Document 2: Japanese Patent Laid-Open Publication No. 2006-169302
Patent Document 3: Japanese Patent Laid-Open Publication No. H04-230645
Patent Document 4: Japanese Patent Laid-Open Publication No. 2005-084365
Patent Document 5: Japanese Patent Laid-Open Publication No. 2006-045311

SUMMARY OF THE INVENTION

The present invention has been done to solve the above problems, and an object thereof is to provide a developer that can prevent the occurrence of pattern collapse and connection between patterns, i.e. bridge defect after development and provide a resist pattern with small edge roughness, and to further provide a patterning process using the same.

To accomplish the above objects, the present invention provides a developer for a photosensitive resist composition, comprising a compound represented by the general formula (1)

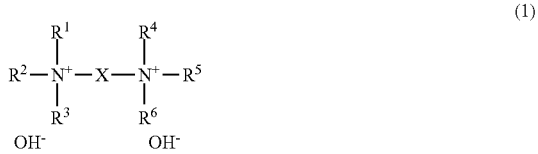

(1)

wherein $R^1$ to $R^6$ represent a linear, branched, or cyclic alkyl group having 1 to 4 carbon atoms; and X represents a linear or branched alkylene group having 6 to 16 carbon atoms and optionally having an ester group.

Such a developer can reduce swell of the resist film in the developer, whereby the occurrence of pattern collapse and connection between patterns, i.e. bridge defect after development of the photosensitive resist composition can be prevented, and a resist pattern with small edge roughness can be obtained.

The compound represented by the general formula (1) is preferably contained in an amount of 0.1 to 20% by mass based on a total amount of the developer.

The above amount is preferable since the effect of the compound represented by the general formula (1) is sufficiently exhibited.

The compound represented by the general formula (1) is preferably any of hexamethonium hydroxide, decamethonium hydroxide, and succinylcholine hydroxide.

The developer containing such a compound can prevent the occurrence of pattern collapse and bridge defect more effectively, and provide a resist pattern with smaller edge roughness.

The developer of the present invention preferably further comprises 0.0001 to 5% by mass of an acetylene alcohol represented by the general formula (AA-1),

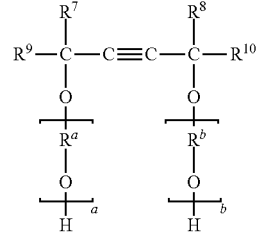

(AA-1)

wherein $R^7$ to $R^{10}$ each represent an identical or different alkyl group having 1 to 20 carbon atoms; $R^a$ and $R^b$ each represent an identical or different alkylene group having 1 to 10 carbon atoms; and "a" and "b" are each an integer satisfying $0 \leq a+b \leq 60$.

When the acetylene alcohol is contained, foaming of the developer can be suppressed and the surface tension can be lowered.

Moreover, the present invention also provides a patterning process comprising the steps of: applying a photosensitive resist composition onto a substrate; performing exposure to a high energy beam after heat treatment; performing development by using the above-mentioned developer.

The patterning process using the developer of the present invention can prevent the occurrence of pattern collapse and bridge defect and provide a resist pattern with small edge roughness.

The photoresist composition is preferably a chemically amplified positive resist composition an alkali dissolution rate of which is increased by acid.

In addition, a base resin of the chemically amplified positive resist composition is preferably a polymer compound that contains a repeating unit having an acid-labile group and a repeating unit having a hydroxyl group and/or a lactone ring as an adhesive group.

The developer of the present invention can be suitably used for development of the chemically amplified positive resist composition as mentioned above.

In addition, it is preferred that the polymer compound has a weight average molecular weight within a range of 1,000 to 500,000, and the repeating unit having an acid-labile group is one or more repeating units selected from repeating units a1 and a2 represented by the general formula (2), in which a hydrogen atom of a carboxyl group or a phenolic hydroxyl group is substituted with an acid-labile group,

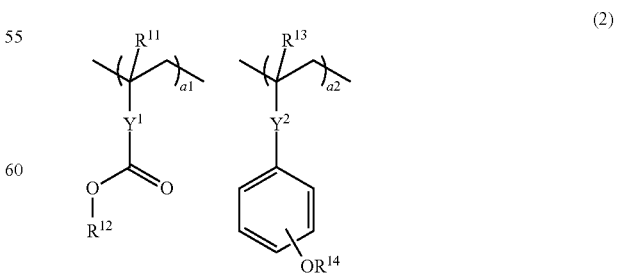

(2)

wherein $R^{11}$ and $R^{13}$ independently represent a hydrogen atom or a methyl group; $R^{12}$ and $R^{14}$ represent an acid-labile group; $Y^1$ represents a single bond or a divalent linking group having 1 to 12 carbon atoms and any one or more of an ester group, a lactone ring, a phenylene group, and a naphthylene group; $Y^2$ represents a single bond, an ester group, or an amide group; $0 \leq a1 \leq 0.9$; $0 \leq a \leq 0.9$; and $0 < a1+a2 < 1.0$.

The polymer compound having the repeating unit represented by the general formula (2) can be suitably used for the patterning process of the present invention. Also, when the weight average molecular weight of the polymer compound is in the above range, the resist composition is excellent in heat resistance, and there is no possibility of lowering the solubility in alkaline solution and causing a footing profile after patterning.

In addition, the polymer compound preferably further contains one or more repeating units selected from repeating units b1 to b3 having a sulfonium salt structure represented by the general formula (3),

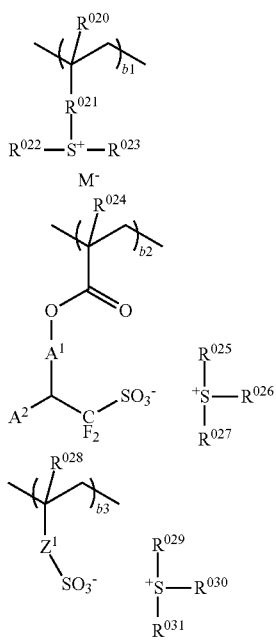

(3)

wherein $R^{020}$, $R^{024}$, and $R^{028}$ represent a hydrogen atom or a methyl group; $R^{021}$ represents a single bond, a phenylene group, —O—$R^{033}$—, or —C(=O)—Y—$R^{033}$—, where Y represents an ether group or a NH group, and $R^{033}$ represents a phenylene group or a linear, branched, or cyclic alkylene group or alkenylene group having 1 to 6 carbon atoms and optionally containing a carbonyl group, an ester group, an ether group, or a hydroxyl group; $R^{022}$, $R^{023}$, $R^{025}$, $R^{026}$, $R^{027}$, $R^{029}$, $R^{030}$, and $R^{031}$ may be the same or different and represent a linear, branched, or cyclic alkyl group having 1 to 12 carbon atoms and optionally containing a carbonyl group, an ester group, or an ether group, an aryl group having 6 to 12 carbon atoms, an aralkyl group having 7 to 20 carbon atoms, or a thiophenyl group; $A^1$ represents a single bond, -$A^0$-C(=O)—O—, -$A^0$-O—, or -$A^0$-O—C (=O)—, where $A^0$ represents a linear, branched, or cyclic alkylene group having 1 to 12 carbon atoms and optionally containing a carbonyl group, an ester group, or an ether group; $A^2$ represents a hydrogen atom, a $CF_3$ group, or =O; $Z^1$ represents a single bond, a methylene group, an ethylene group, a phenylene group, a fluorinated phenylene group, —O—$R^{032}$—, or —C(=O)—$Z^2$—$R^{032}$—, where $Z^2$ represents an ether group or a NH group, and $R^{032}$ represents a phenylene group, a fluorinated phenylene group, a phenylene group substituted with a trifluoromethyl group, or a linear, branched, or cyclic alkylene group or alkenylene group having 1 to 6 carbon atoms and optionally containing a carbonyl group, an ester group, an ether group, or a hydroxyl group; $M^-$ represents a non-nucleophilic counter ion; $0 \leq b1 \leq 0.3$; $0 \leq b2 \leq 0.3$; $0 \leq b3 \leq 0.3$; and $0 < b1+b2+b3 \leq 0.3$.

When the above repeating unit is further contained, edge roughness of the pattern after development can be further improved.

The photosensitive resist composition preferably contains any one or more of an organic solvent, a basic compound, a dissolution control agent, and a surfactant.

Such a photosensitive resist composition can be suitably used for the patterning process of the present invention since, for example, the dissolution rate of the base resin into the developer is enhanced in the exposed part by a catalytic reaction thereof, thereby leading to a highly sensitive positive resist composition.

The high energy beam is preferably a KrF excimer laser having a wavelength of 248 nm, an ArF excimer laser having a wavelength of 193 nm, an electron beam, or a soft X-ray having a wavelength of 3 to 15 nm.

When such a high energy beam is used, a finer pattern can be formed in the resist film.

As mentioned above, the developer of the present invention can reduce swell of the resist film in the developer. Thus, the patterning process using the developer of the present invention can prevent the occurrence of pattern collapse and bridge defect after development, and can provide a resist pattern with small edge roughness.

DETAILED DESCRIPTION OF THE PREFERRED EMBODIMENTS

Hereinafter, embodiments of the present invention will be described, but the present invention is not limited thereto.

As mentioned above, it has been desired to develop a developer and a patterning process that can prevent the occurrence of pattern collapse and bridge defect after development, and can provide a resist pattern with small edge roughness.

The present inventor has earnestly investigated to accomplish the above objects, and consequently found that a developer that contains a compound having two ammonium hydroxide groups per molecule and a patterning process using the same can prevent the occurrence of pattern collapse and bridge defect after development by reducing swell of the resist film in the developer, thereby brought the present invention to completion.

That is, the present invention is a developer for a photosensitive resist composition, comprising a compound represented by the general formula (1)

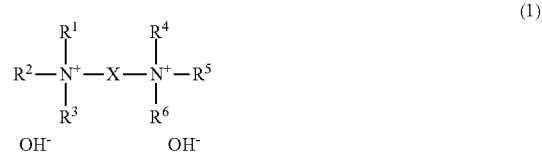

(1)

wherein $R^1$ to $R^6$ represent a linear, branched, or cyclic alkyl group having 1 to 4 carbon atoms; and X represents a linear or branched alkylene group having 6 to 16 carbon atoms and optionally having an ester group.

Illustrative examples of the compound having two ammonium hydroxide groups per molecule represented by the general formula (1) include the following compounds.

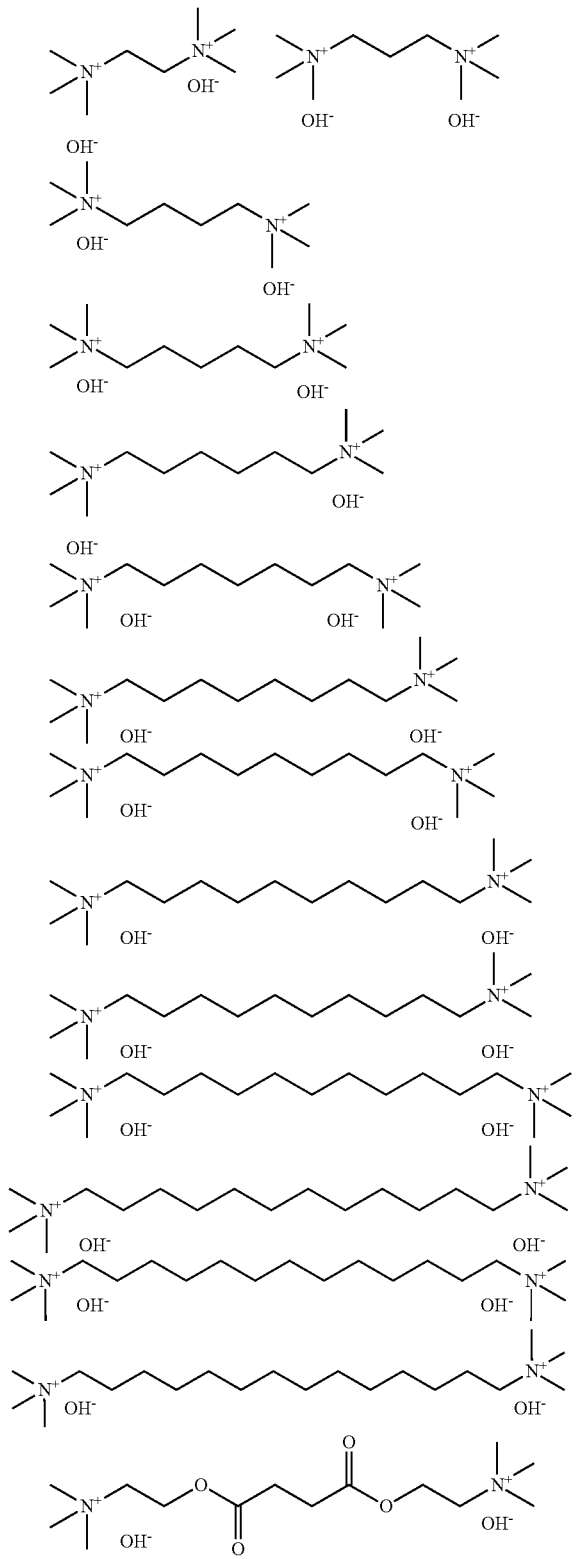

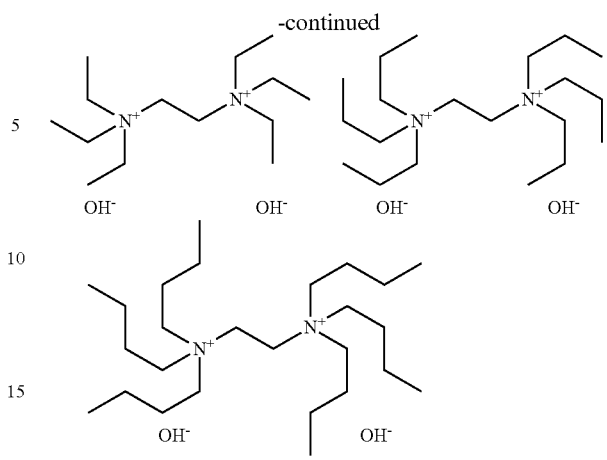

-continued

Among them, hexamethonium hydroxide, decamethonium hydroxide, and succinylcholine hydroxide are most preferably used.

In general, as the developer of alkaline water, tetramethylammonium hydroxide (TMAH) is used. Although potassium hydroxide had been used before, it has shifted to hydroxyl salts of quaternary ammonium since it turned out that alkali metal adversely affects device operation. Examples of the quaternary ammonium salt include, besides TMAH mentioned above, tetraethylammonium hydroxide, tetrapropylammonium hydroxide, tetrabutylammonium hydroxide, tetrapentylammonium hydroxide, tributylmethylammonium hydroxide, trimethylhydroxyethylammonium hydroxide (hereinafter, referred to as choline), tetraethanolammonium hydroxide, and methyltriethanolammonium hydroxide.

The developer of an aqueous TMAH solution is widely used, but it has the problem that pattern collapse is caused due to swell when this solution is applied to a polymethacrylate based resist which generates carboxylic acid after deprotection. Accordingly, tetrabutylammonium hydroxide (TBAH), which has longer alkyl chain, has been investigated. When the alkyl group is longer, the molecular weight becomes larger, and the developer less permeates into the resist film. Thus, swell is reduced, and consequently pattern collapse is improved. However, in a line pattern formation with a pattern size of 20 nm or less, pattern collapse cannot be sufficiently prevented even when the TBAH developer is used.

The inventive developer containing the compound represented by the general formula (1) can suppress pattern collapse and bridge defect by reducing swell of the resist film in the developer, compared with the case using tetraalkylammonium hydroxide as mentioned above.

The compound represented by the general formula (1) is preferably contained in an amount of 0.1 to 20% by mass, more preferably 0.1 to 10% by mass, much more preferably 0.5 to 8% by mass, particularly preferably 1.0 to 6% by mass, based on a total amount of the developer. As the solvent, water such as ultrapure water and ion-exchanged water can be suitably used.

The developer of the present invention may contain an acetylene alcohol represented by the general formula (AA-1) in addition to the compound having two ammonium hydroxide per molecule represented by the general formula (1),

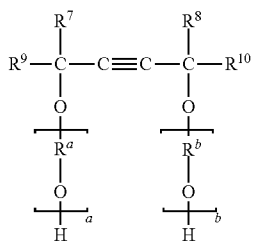

(AA-1)

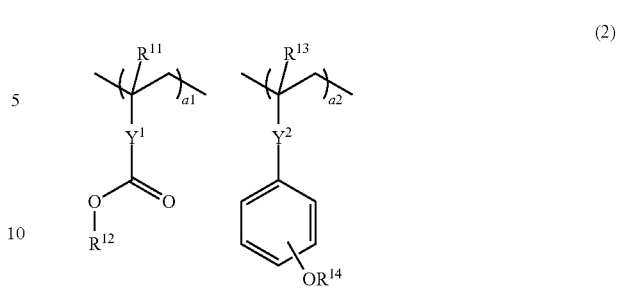

wherein $R^7$ to $R^{10}$ each represent an identical or different alkyl group having 1 to 20 carbon atoms; $R^a$ and $R^b$ each represent an identical or different alkylene group having 1 to 10 carbon atoms; and "a" and "b" are each an integer satisfying $0 \leq a+b \leq 60$.

The acetylene alcohol may be a commercial product. Examples of the commercial product include Surfynol 104 series, 400 series, available from Nisshin Chemical Industry Co., Ltd.

The content of the acetylene alcohol is preferably 0.0001 to 5% by mass, more preferably 0.001 to 3% by mass, much more preferably 0.01 to 1% by mass, based on a total amount of the developer. The acetylene alcohol has both of defoaming effect and surfactant effect. When microbubbles exist in the developer, development defects may be caused since a part where the bubble contacts with the resist surface is not developed. Thus, for preventing microbubbles, a defoaming agent is preferably added. Also, water is hard to be applied onto the resist surface because of high surface tension thereof, so that it is preferable to reduce the surface tension to facilitate the application onto the resist surface. The addition of a surfactant is effective for this, however, common surfactants easily make bubbles while the surface tension is reduced. The acetylene alcohol can reduce the surface tension with suppressing bubbles.

As mentioned above, the developer of the present invention can reduce swell of the resist film during development. Accordingly, when a photosensitive resist composition is developed with the developer of the present invention, the occurrence of pattern collapse and bridge defect after development can be prevented, and a resist pattern with small edge roughness can be obtained.

Further, the present invention provides a patterning process comprising the steps of: applying a photosensitive resist composition onto a substrate; performing exposure to a high energy beam after heat treatment; performing development by using the developer of the present invention. Hereinafter, the patterning process of the present invention will be described.

As the photosensitive resist composition used in the patterning process of the present invention, there may be mentioned a chemically amplified positive resist composition an alkali dissolution rate of which is increased by acid, in particular, a chemically amplified positive resist composition a base resin of which is a polymer compound that contains a repeating unit having an acid-labile group and a repeating unit having an hydroxyl group and/or a lactone ring as an adhesive group.

As the base resin of the chemically amplified positive resist composition, a polymer compound that contains repeating unit a1 and/or a2 in which a hydrogen atom of a carboxyl group or a phenolic hydroxyl group is substituted with an acid-labile group as represented by the general formula (2) is preferably used.

wherein $R^{11}$ and $R^{13}$ independently represent a hydrogen atom or a methyl group; $R^{12}$ and $R^{14}$ represent an acid-labile group; $Y^1$ represents a single bond or a divalent linking group having 1 to 12 carbon atoms and any one or more of an ester group, a lactone ring, a phenylene group, and a naphthylene group; $Y^2$ represents a single bond, an ester group, or an amide group; $0 \leq a1 \leq 0.9$; and $0 < a1+a2 < 1.0$. $Y^1$ may be a phenylene group or a naphthylene group itself.

Among the repeating units contained in the polymer compound in the present invention, the repeating unit a1 having an acid-labile group, shown in the general formula (2) is obtained by substituting a hydrogen atom of a carboxyl group, particularly a hydroxyl group of (meth)acrylate, with an acid-labile group. Illustrative examples of the monomer to give this repeating unit include the following compounds.

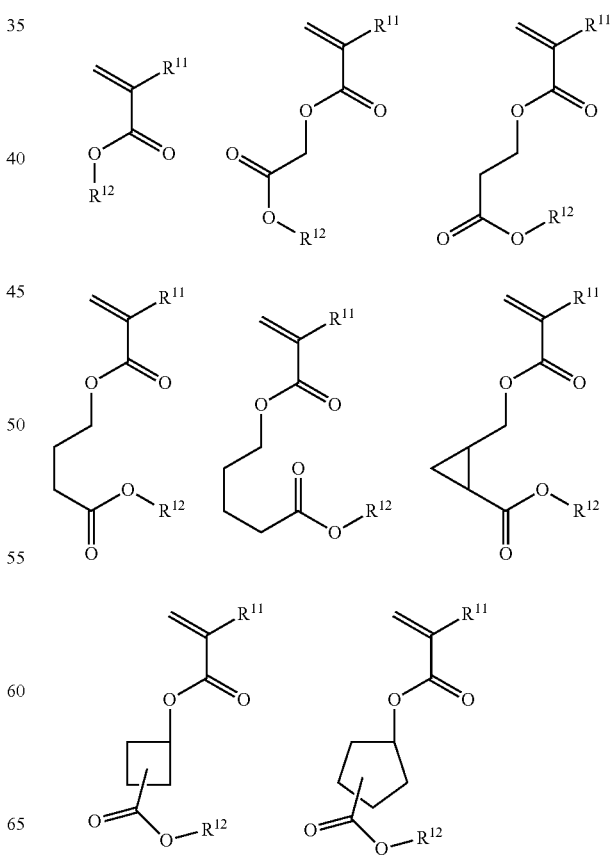

11
-continued
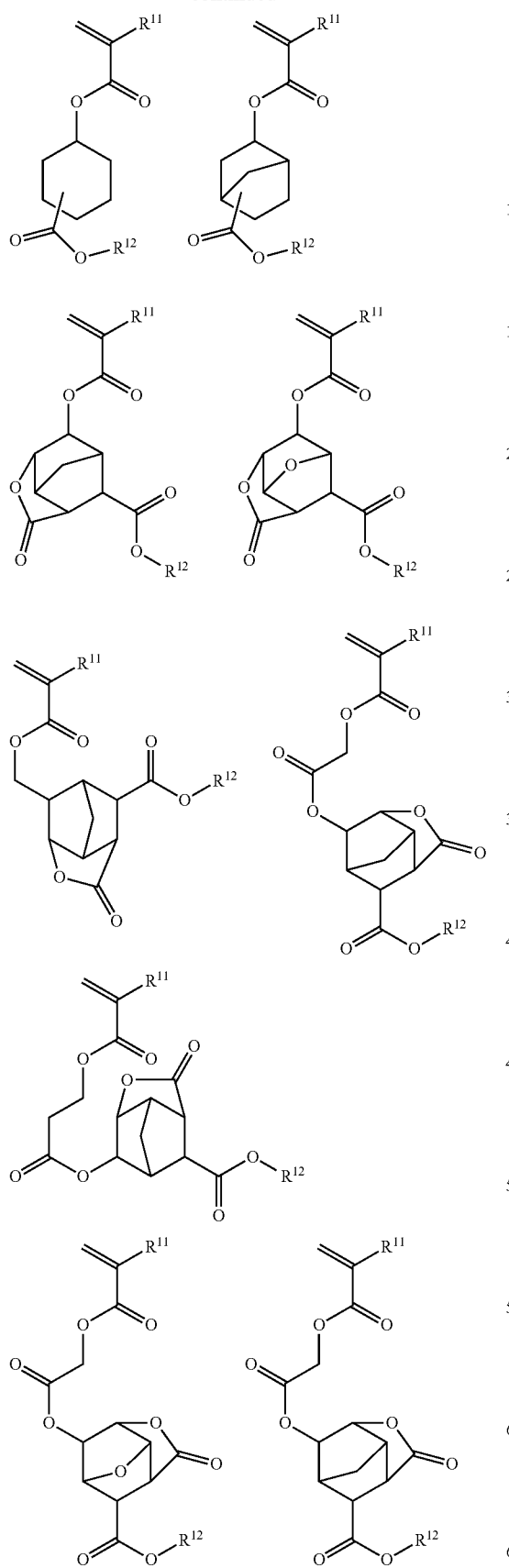
12
-continued
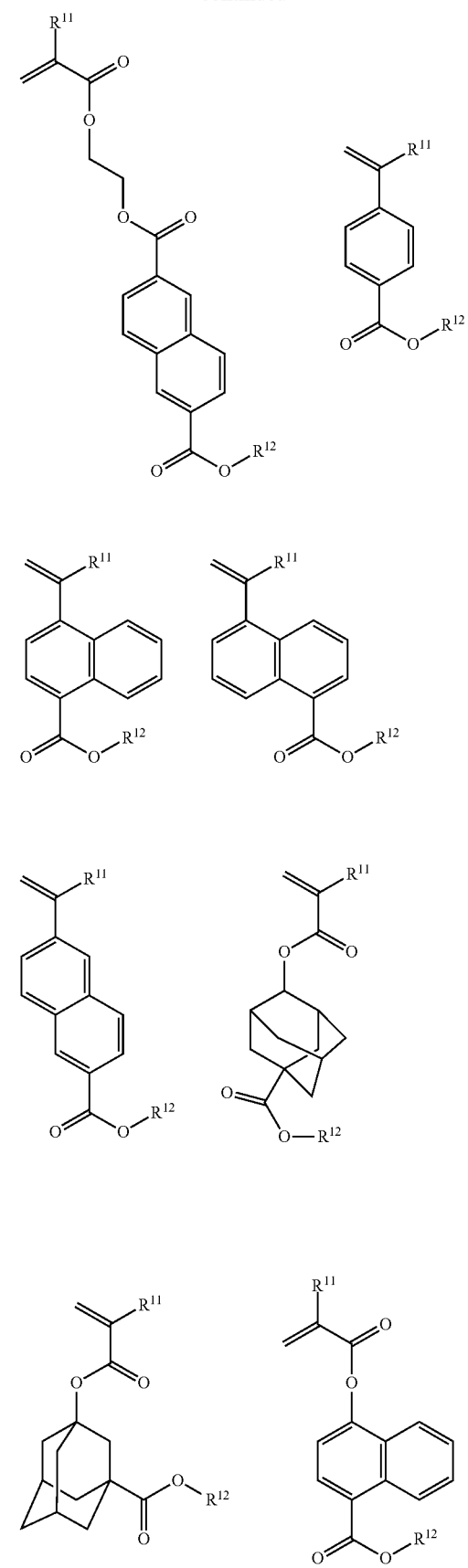

-continued

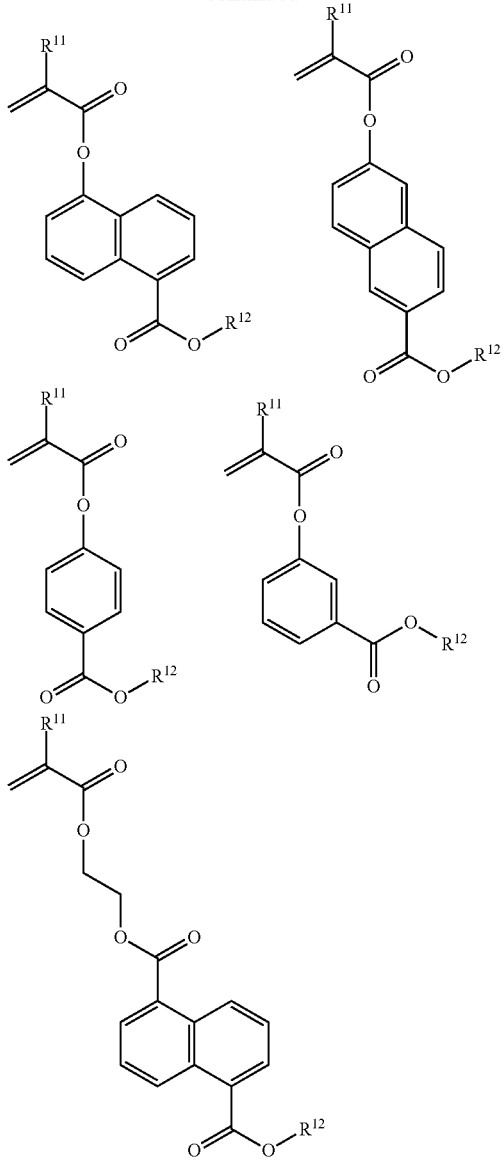

wherein R[11] represents a hydrogen atom or a methyl group; and R[12] represents an acid-labile group.

The repeating unit a2 having an acid-labile group, shown in the general formula (2) is obtained by substituting a hydrogen atom of a phenolic hydroxyl group, preferably a hydroxyl group of hydroxystyrene or hydroxyphenyl(meth)acrylate, with an acid-labile group. Illustrative examples of the monomer to give this repeating unit include the following compounds.

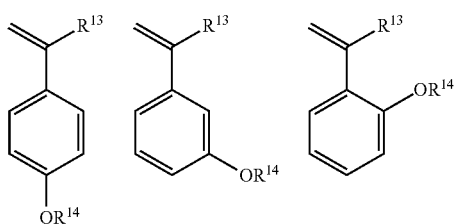

-continued

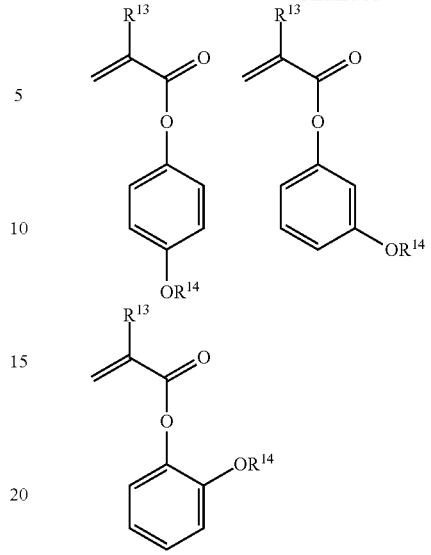

wherein R[13] represents a hydrogen atom or a methyl group; and R[14] represents an acid-labile group.

The acid-labile groups represented by R[12] and R[14] are variously selected, and may be the same or different from each other. In particular, there may be mentioned the following groups represented by the general formulae (A-1) to (A-3).

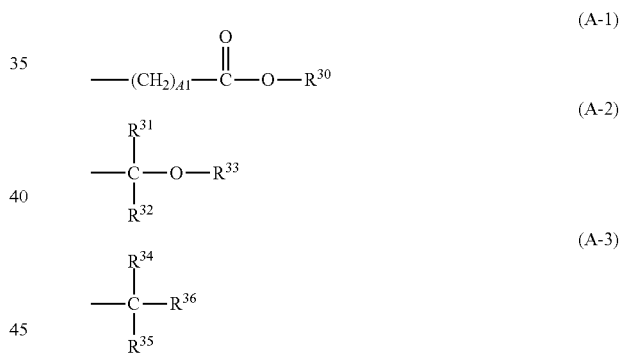

In the formula (A-1), R[30] represents a tertiary alkyl group having 4 to 20, preferably 4 to 15 carbon atoms, wherein each alkyl group represents a trialkylsilyl group having 1 to 6 carbon atoms, an oxoalkyl group having 4 to 20 carbon atoms, or a group represented by the formula (A-3). Illustrative examples of the tertiary alkyl group include a tert-butyl group, a tert-amyl group, a 1,1-diethylpropyl group, a 1-ethylcyclopentyl group, a 1-butylcyclopentyl group, a 1-ethylcyclohexyl group, a 1-butylcyclohexyl group, a 1-ethyl-2-cyclopentenyl group, a 1-ethyl-2-cyclohexenyl group, and a 2-methyl-2-adamantyl group; illustrative examples of the trialkylsilyl group include a trimethylsilyl group, a triethylsilyl group, and a dimethyl-tert-butylsilyl group; and illustrative examples of the oxoalkyl group include a 3-oxocyclohexyl group, a 4-methyl-2-oxooxane-4-yl group, and a 5-methyl-2-oxooxolane-5-yl group. A[1] is an integer of 0 to 6.

Illustrative examples of the acid-labile group of the formula (A-1) include a tert-butoxycarbonyl group, a tert-butoxycarbonylmethyl group, a tert-amyloxycarbonyl group, a tert-amyloxycarbonylmethyl group, a 1,1-diethyl-propyloxycarbonyl group, a 1,1-diethylpropyloxycarbonyl-methyl group, a 1-ethylcyclopentyloxycarbonyl group, a 1-ethylcyclopentyloxycarbonylmethyl group, a 1-ethyl-2-cyclopentenyloxycarbonyl group, a 1-ethyl-2-cyclopentenyloxycarbonylmethyl group, a 1-ethoxyethoxycarbonylmethyl group, a 2-tetrahydropyranyloxycarbonylmethyl group, and a 2-tetrahydrofuranyloxycarbonylmethyl group.

In addition, substituents represented by the formulae (A-1)-1 to (A-1)-10 may be mentioned.

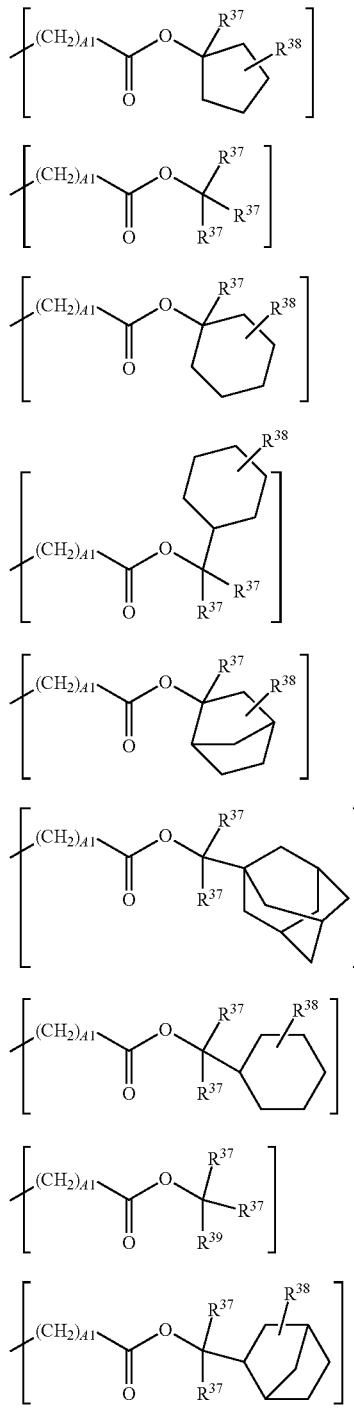

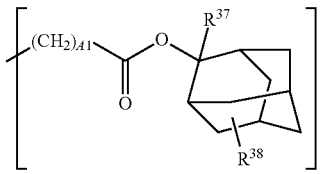

In the formula, each $R^{37}$ may be the same or different, and represent a linear, branched, or cyclic alkyl group having 1 to 10 carbon atoms, or an aryl group having 6 to 20 carbon atoms; $R^{38}$ represents a hydrogen atom, or a linear, branched, or cyclic alkyl group having 1 to 10 carbon atoms; each $R^{39}$ may be the same or different, and represents a linear, branched, or cyclic alkyl group having 2 to 10 carbon atoms, or an aryl group having 6 to 20 carbon atoms; and $A^1$ has the same meaning as above.

In the formula (A-2), $R^{31}$ and $R^{32}$ represent a hydrogen atom or a linear, branched, or cyclic alkyl group having 1 to 18, preferably 1 to 10 carbon atoms. Illustrative example thereof include a methyl group, an ethyl group, a propyl group, an isopropyl group, a n-butyl group, a sec-butyl group, a tert-butyl group, a cyclopentyl group, a cyclohexyl group, a 2-ethylhexyl group, and a n-octyl group. $R^{33}$ represents a monovalent hydrocarbon group having 1 to 18, preferably 1 to 10 carbon atoms, and optionally containing a heteroatom such as an oxygen atom. For example, there may be mentioned a linear, branched, or cyclic alkyl group, and a group in which a part of hydrogen atoms in the alkyl group is substituted with a hydroxyl group, an alkoxy group, an oxo group, an amino group, an alkylamino group, or the like. Illustrative examples of $R^{33}$ include the following substituted alkyl groups.

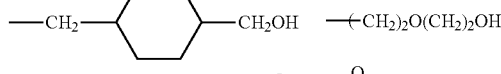
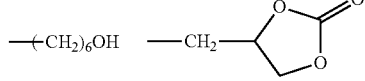

$R^{31}$ and $R^{32}$, $R^{31}$ and $R^{33}$, and $R^{32}$ and $R^{33}$ may be bonded to form a ring together with the carbon atoms to which these groups are bonded; and when the ring is formed, each of $R^{31}$, $R^{32}$, and $R^{33}$ that participate in the ring formation represents a linear or branched alkylene group having 1 to 18, preferably 1 to 10 carbon atoms, and the carbon number in the ring is preferably in the range of 3 to 10, particularly 4 to 10.

Among the acid-labile group represented by the formula (A-2), illustrative examples of the linear or branched one include groups of the following formulae (A-2)-1 to (A-2)-69.

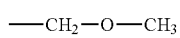 (A-2)-1

 (A-2)-2

 (A-2)-3

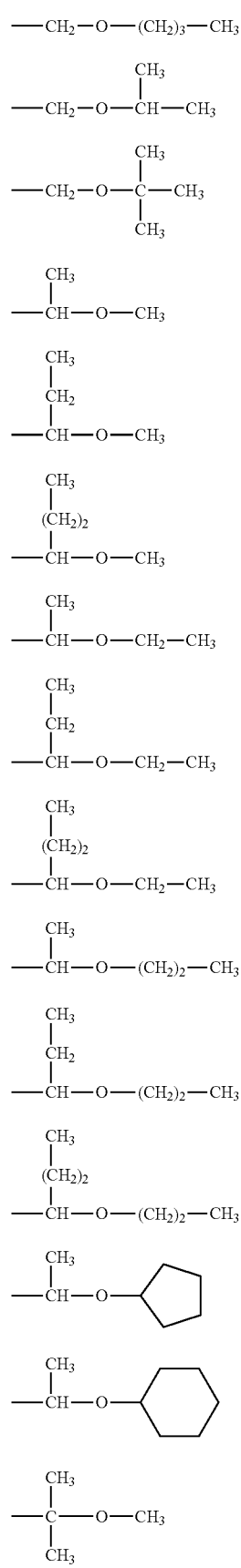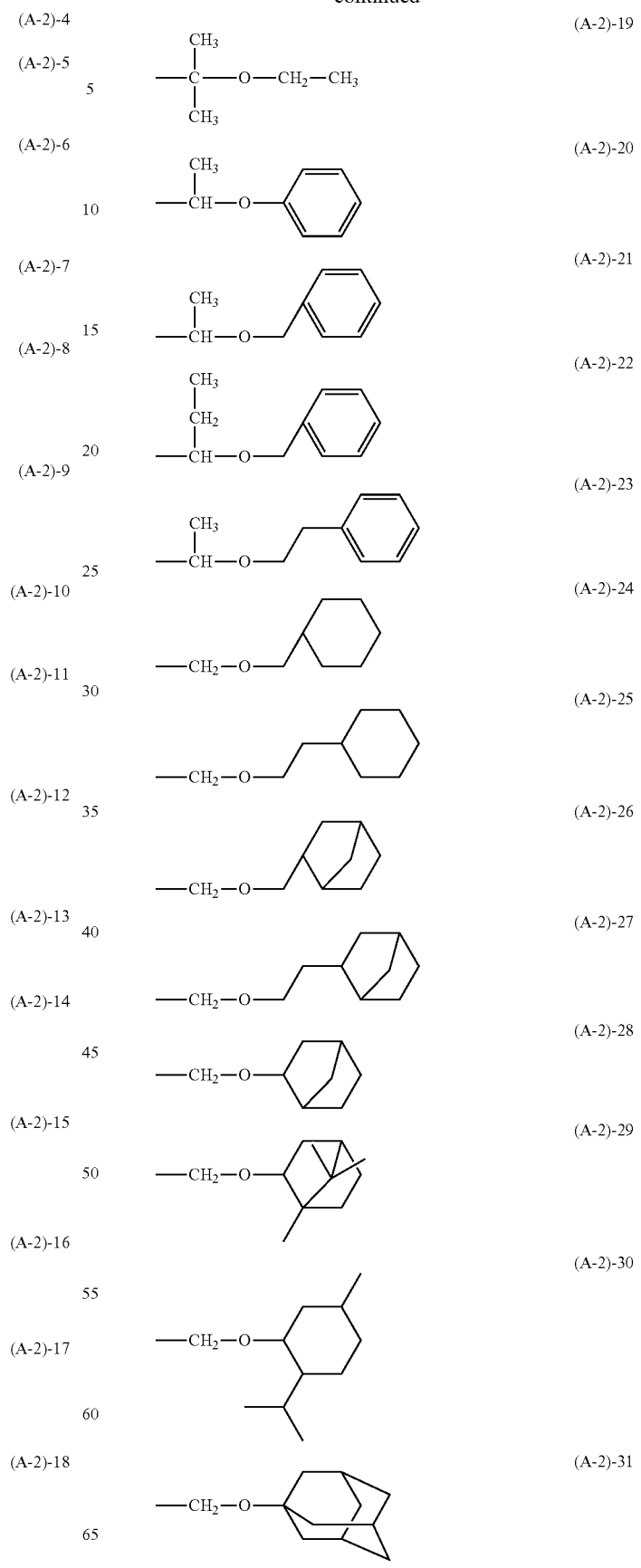

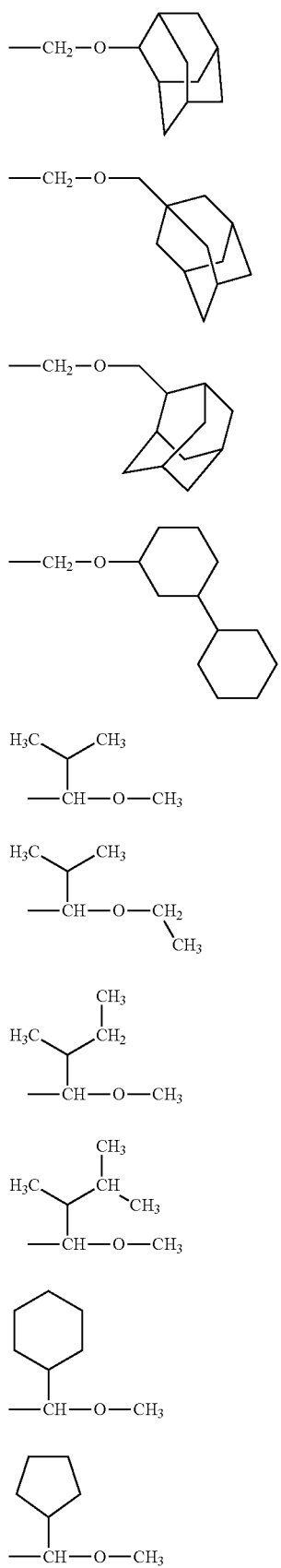

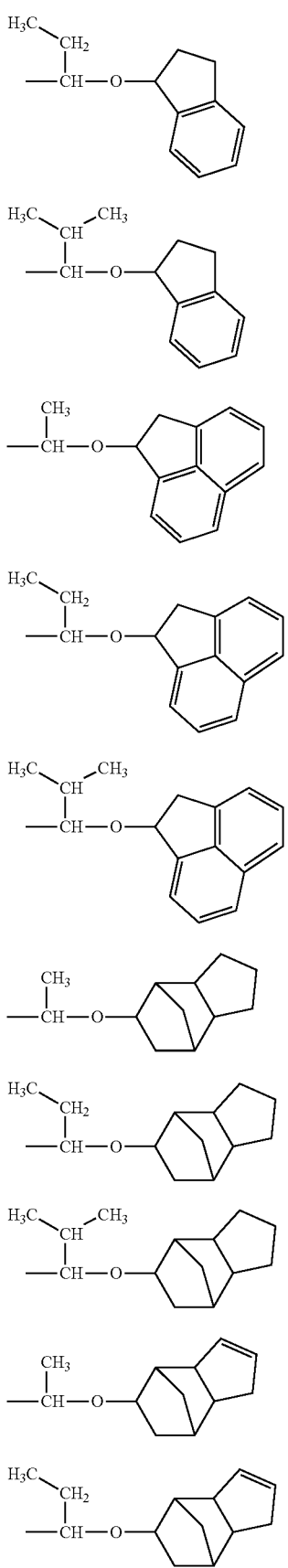
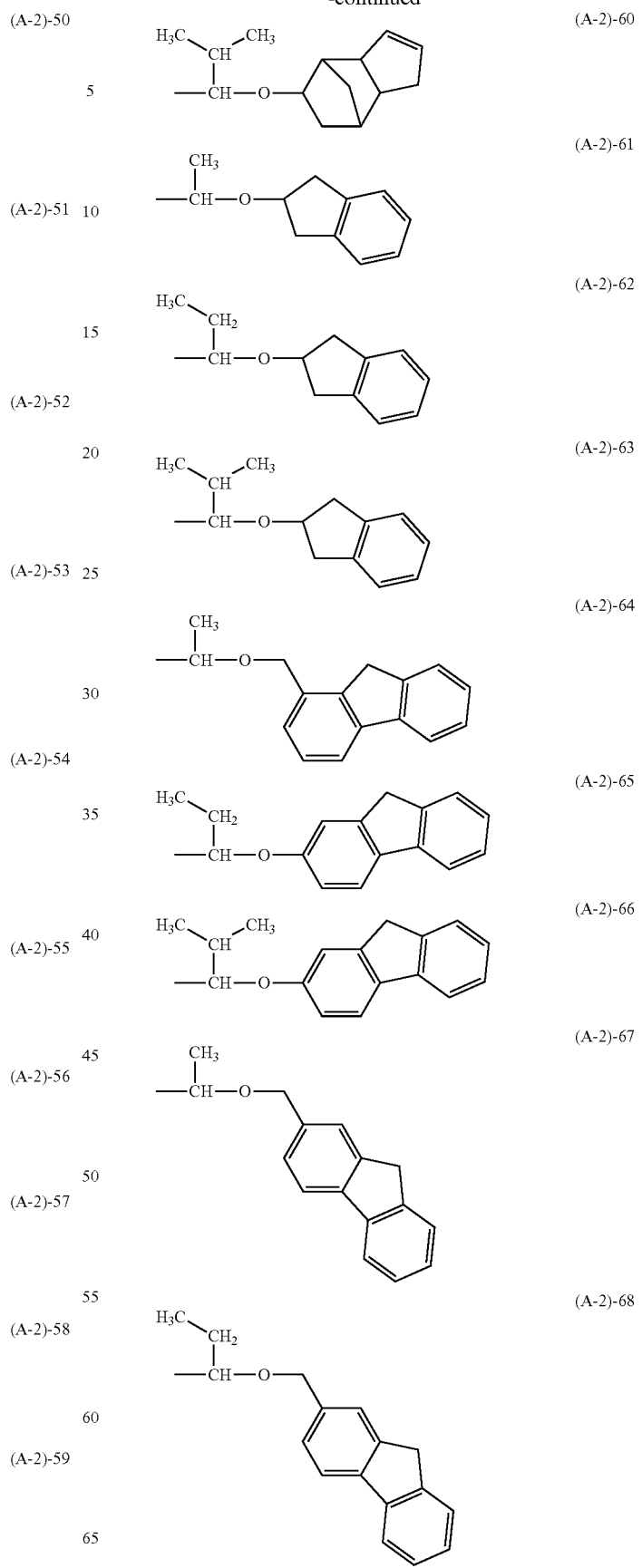

-continued

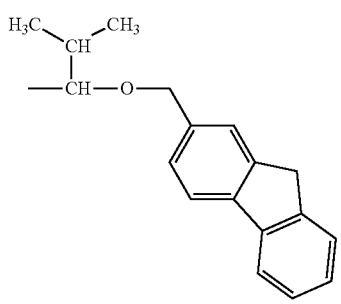
(A-2)-69

Among the acid-labile group represented by the formula (A-2), illustrative examples of the cyclic one include a tetrahydrofuran-2-yl group, a 2-methyltetrahydrofuran-2-yl group, a tetrahydropyran-2-yl group, and a 2-methyltetrahydropyran-2-yl group.

Further, two parts bonding to an acid-labile group in the repeating unit constituting the base resin may be linked together through an acid-labile group represented by the formula (A-2a) or (A-2b) to form intermolecular or intramolecular crosslinking.

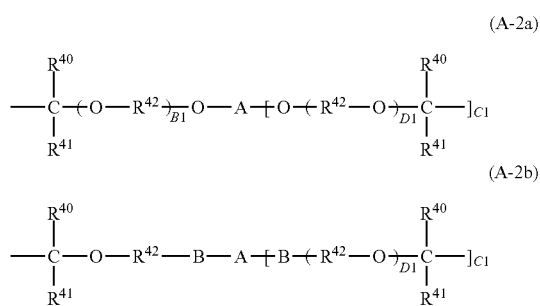
(A-2a)
(A-2b)

In these formulae, $R^{40}$ and $R^{41}$ represent a hydrogen atom or a linear, branched, or cyclic alkyl group having 1 to 8 carbon atoms. Alternatively, $R^{40}$ and $R^{41}$ may be bonded to form a ring together with the carbon atoms to which these groups are bonded; and when the ring is formed, $R^{40}$ and $R^{41}$ represent a linear or branched alkylene group having 1 to 8 carbon atoms. $R^{42}$ represents a linear, branched, or cyclic alkylene group having 1 to 10 carbon atoms; B1 and D1 represent 0 or an integer of 1 to 10, preferably 0 or an integer of 1 to 5; and C1 represents an integer of 1 to 7. "A" represents an aliphatic or alicyclic saturated hydrocarbon group, an aromatic hydrocarbon group, or a heterocyclic group having 1 to 50 carbon atoms with a valency of (C1+1); and in these group, a heteroatom may be contained, or a part of the hydrogen atoms bonded to the carbon atom may be substituted with a hydroxyl group, a carboxyl group, a carbonyl group, or a halogen atom such as a fluorine atom. "B" represents —CO—O—, —NHCO—O—, or —NHCONH—.

In this case, "A" is preferably a linear, branched, or cyclic alkylene group, alkyltriyl group, alkyltetrayl group having 2 to 4 valency and 1 to 20 carbon atoms, or an arylene group having 6 to 30 carbon atoms; and in these group, a heteroatom may be contained, or a part of the hydrogen atoms bonded to the carbon atom may be substituted with a hydroxyl group, a carboxyl group, an acyl group, or a halogen atom. C1 preferably represents an integer of 1 to 3.

Illustrative examples of the crosslinking acetal group represented by the general formulae (A-2a) and (A-2b) include groups of the following formulae (A-2a)-1 to 8.

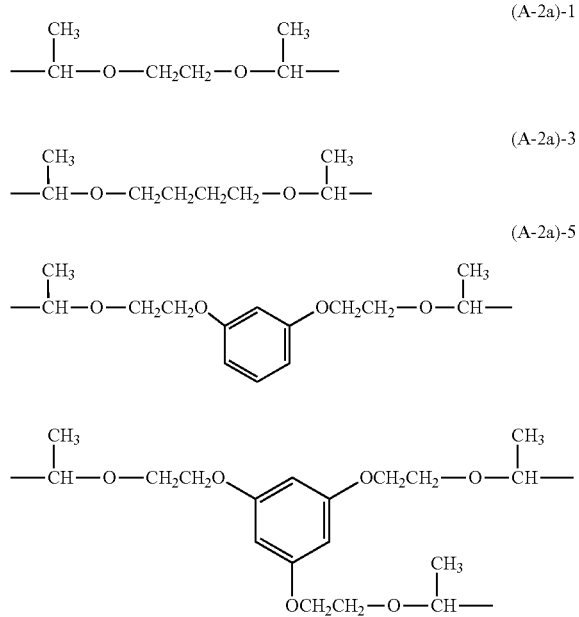

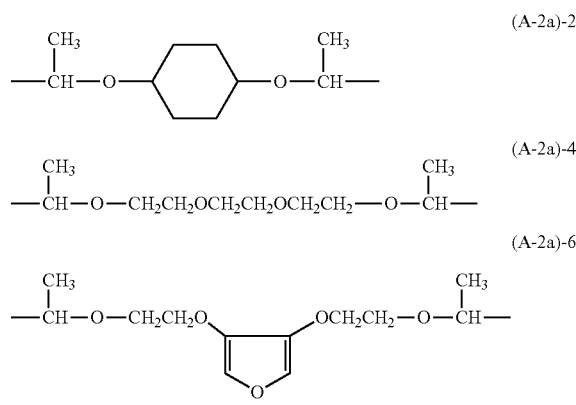

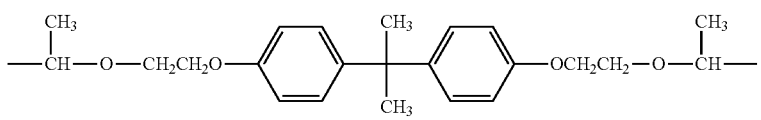

(A-2a)-8

Next, in the formula (A-3), $R^{34}$, $R^{35}$, and $R^{36}$ represent a monovalent hydrocarbon group such as a linear, branched, or cyclic alkyl group having 1 to 20 carbon atoms, a linear, branched, or cyclic alkenyl group having 2 to 20 carbon atoms, and an aryl group having 6 to 20 carbon atoms, and these groups may contain a heteroatom such as an oxygen atom, a sulfur atom, a nitrogen atom, and a fluorine atom. $R^{34}$ and $R^{35}$, $R^{34}$ and $R^{36}$, and $R^{35}$ and $R^{36}$ may be bonded to form an aliphatic ring having 3 to 20 carbon atoms together with the carbon atoms to which these groups are bonded.

Illustrative examples of the tertiary alkyl group represented by the formula (A-3) include a tert-butyl group, a triethylcarbyl group, a 1-ethylnorbornyl group, a 1-methylcyclohexyl group, a 1-ethylcyclopentyl group, a 2-(2-methyl)adamantyl group, a 2-(2-ethyl)adamantyl group, and a tert-amyl group.

Other examples of the tertiary alkyl group include the following formulae (A-3)-1 to (A-3)-18.

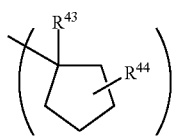

(A-3)-1

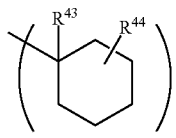

(A-3)-2

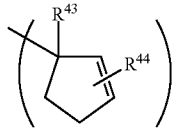

(A-3)-3

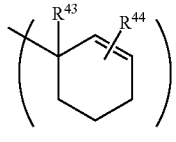

(A-3)-4

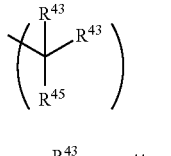

(A-3)-5

(A-3)-6

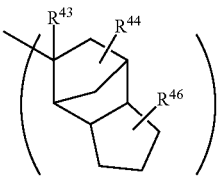

(A-3)-7

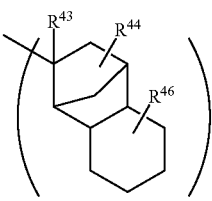

(A-3)-8

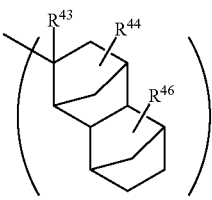

(A-3)-9

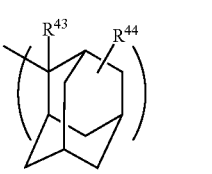

(A-3)-10

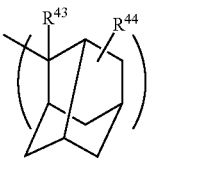

(A-3)-11

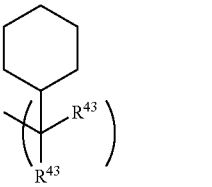

(A-3)-12

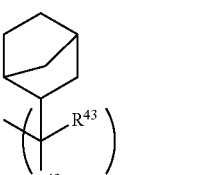

(A-3)-13

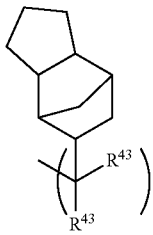

(A-3)-14

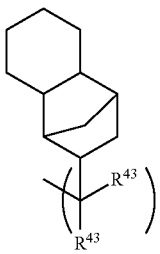

(A-3)-15

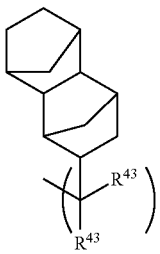

(A-3)-16

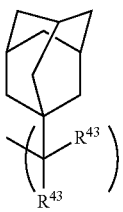

(A-3)-17

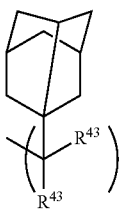

(A-3)-18

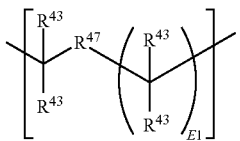

(A-3)-19

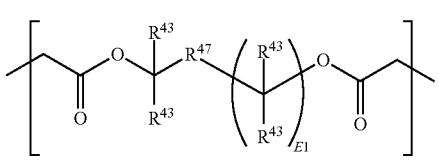

(A-3)-20

In the formulae (A-3)-19 and (A-3)-20, $R^{43}$ has the same meaning as above, and $R^{47}$ represents a linear, branched, or cyclic alkylene group having 1 to 20 carbon atoms, or an arylene group such as a phenylene group, and these group may contain a heteroatom such as an oxygen atom, a sulfur atom, and a nitrogen atom. E1 represents an integer of 1 to 3.

As the acid-labile group represented by the formula (A-3), those represented by the formula (A-3)-21 is particularly preferable. That is, the repeating unit a1 is preferably a repeating unit of (meth)acrylic ester having the exo structure represented by the formula (a1-3-21), which contains the acid-labile group of the formula (A-3)-21.

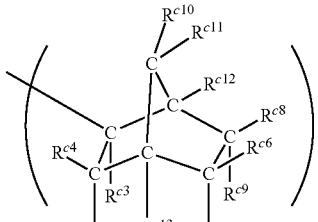

(A-3)-21

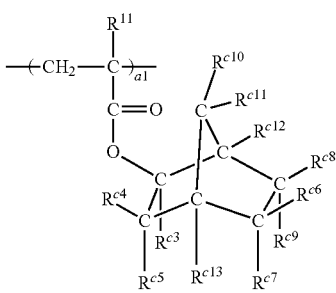

(a1-3-21)

In the formulae (A-3)-1 to (A-3)-18, each $R^{43}$ may be the same or different, and represent a linear, branched, or cyclic alkyl group having 1 to 8 carbon atoms, or an aryl group having 6 to 20 carbon atoms, such as a phenyl group. $R^{44}$ and $R^{46}$ represent a hydrogen atom or a linear, branched, or cyclic alkyl group having 1 to 20 carbon atoms. $R^{45}$ represents an aryl group having 6 to 20 carbon atoms such as a phenyl group.

Further, two parts bonding to an acid-labile group in the repeating unit constituting the base resin may be linked together through a two or more valent acid-labile group including $R^{47}$, which is an alkylene group or an arylene group, as represented by the formulae (A-3)-19 and (A-3)-20 to form intermolecular or intramolecular crosslinking.

wherein $R^{11}$ and a1 have the same meanings as above; $R^{c3}$ represents a linear, branched, or cyclic alkyl group having 1 to 8 carbon atoms, or an optionally substituted aryl group having 6 to 20 carbon atoms; $R^{c4}$ to $R^{c9}$, $R^{c12}$ and $R^{c13}$ independently represent a hydrogen atom or a monovalent hydrocarbon group having 1 to 15 carbon atoms and optionally containing a heteroatom; $R^{c10}$ and $R^{c11}$ represent a hydrogen atom or a monovalent hydrocarbon group having 1 to 15 carbon atoms and optionally containing a heteroatom; $R^{c4}$ and $R^{c5}$, $R^{c6}$ and $R^{c8}$, $R^{c6}$ and $R^{c9}$, $R^{c7}$ and $R^{c9}$, $R^{c7}$ and $R^{c13}$, $R^{c8}$ and $R^{c12}$, $R^{c10}$ and $R^{c11}$, or $R^{c11}$ and $R^{c12}$ may be bonded with each other to form a ring, and in this case, the groups that participate in the ring formation represent a divalent hydrocarbon group having 1 to 15 carbon atoms and optionally containing a heteroatom. Furthermore, $R^{c4}$ and $R^{c13}$, $R^{c10}$ and $R^{c13}$ or $R^{c6}$ and $R^{c8}$ may be directly bonded to form a double bond between the groups bonded to the adjacent carbons. Note that, this formula also represents an enantiomer thereof.

Examples of an ester monomer to give the repeating unit having the exo structure represented by the formula (a1-3-21) is described in Japanese Patent Laid-Open Publication No. 2000-327633. Illustrative examples thereof are shown below, though not limited to them.

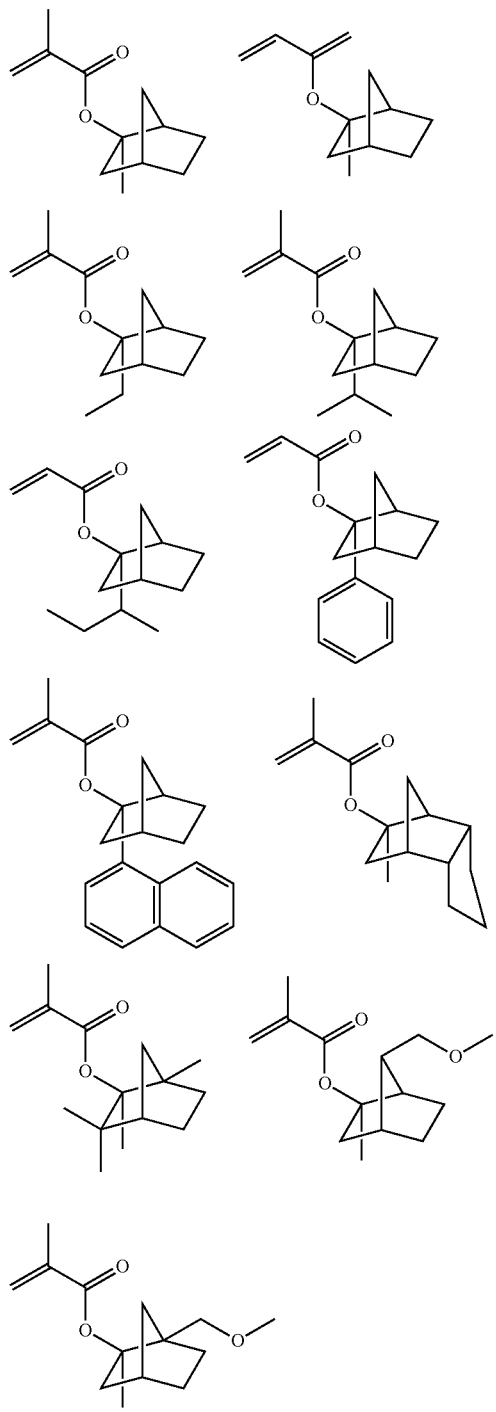

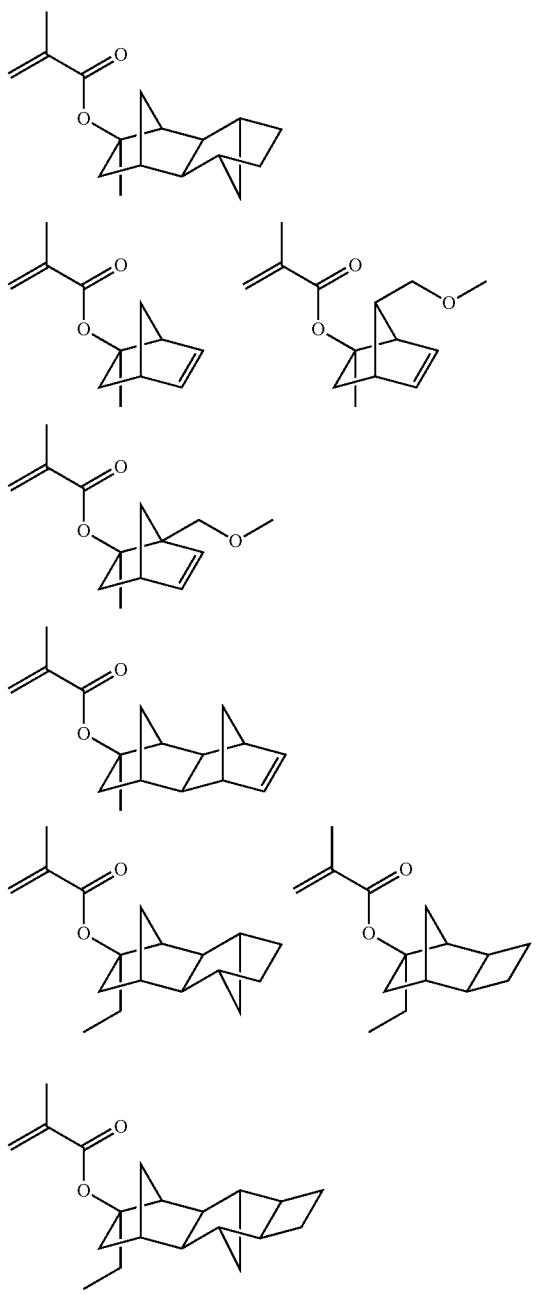

As the acid-labile group represented by the formula (A-3), those represented by the formula (A-3)-22 is also preferable. That is, a repeating unit of (meth)acrylic ester having a furandiyl group, a tetrahydrofurandiyl group, or an oxanorbornanediyl group as represented by the formula (a1-3-22), which contains the acid-labile group of the formula (A-3)-22, is also preferable as the repeating unit a1.

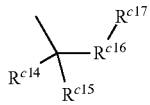

(A-3)-22

-continued

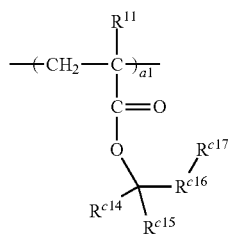

(a1-3-22)

wherein $R^{11}$ and a1 have the same meanings as above; $R^{c14}$ and $R^{c15}$ independently represent a linear, branched, or cyclic monovalent hydrocarbon group having 1 to 10 carbon atoms; $R^{c14}$ and $R^{c15}$ may be bonded with each other to form an alicyclic hydrocarbon ring together with the carbon atoms to which these groups are bonded; $R^{c16}$ represents a divalent group selected from a furandiyl group, a tetrahydrofurandiyl group, or an oxanorbornanediyl group; and $R^{c17}$ represents a hydrogen atom or a linear, branched, or cyclic monovalent hydrocarbon group having 1 to 10 carbon atoms and optionally containing a heteroatom.

Illustrative examples of the monomer to give the repeating unit substituted with the acid-labile group having a furandiyl group, a tetrahydrofurandiyl group, or an oxanorbornanediyl group include the following compounds. Incidentally, Ac and Me denote an acetyl group and a methyl group, respectively.

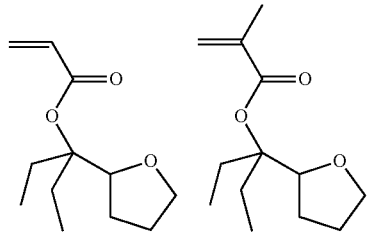

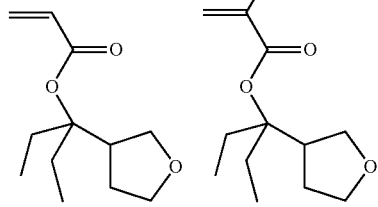

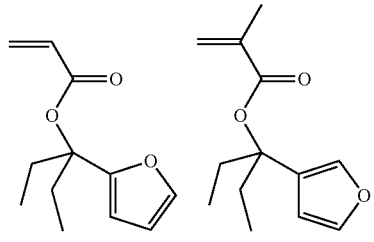

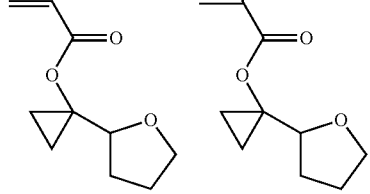

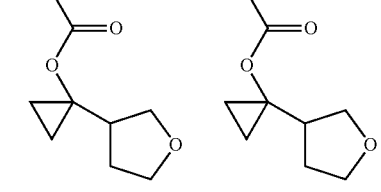

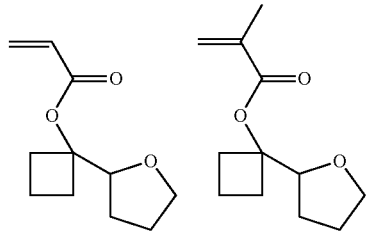

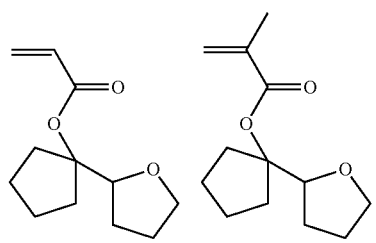

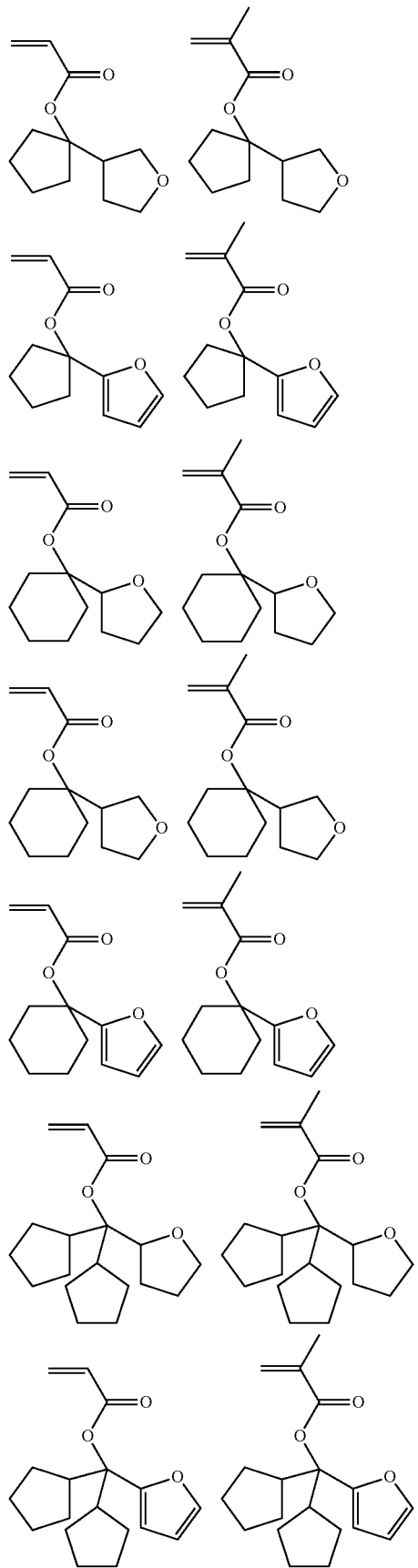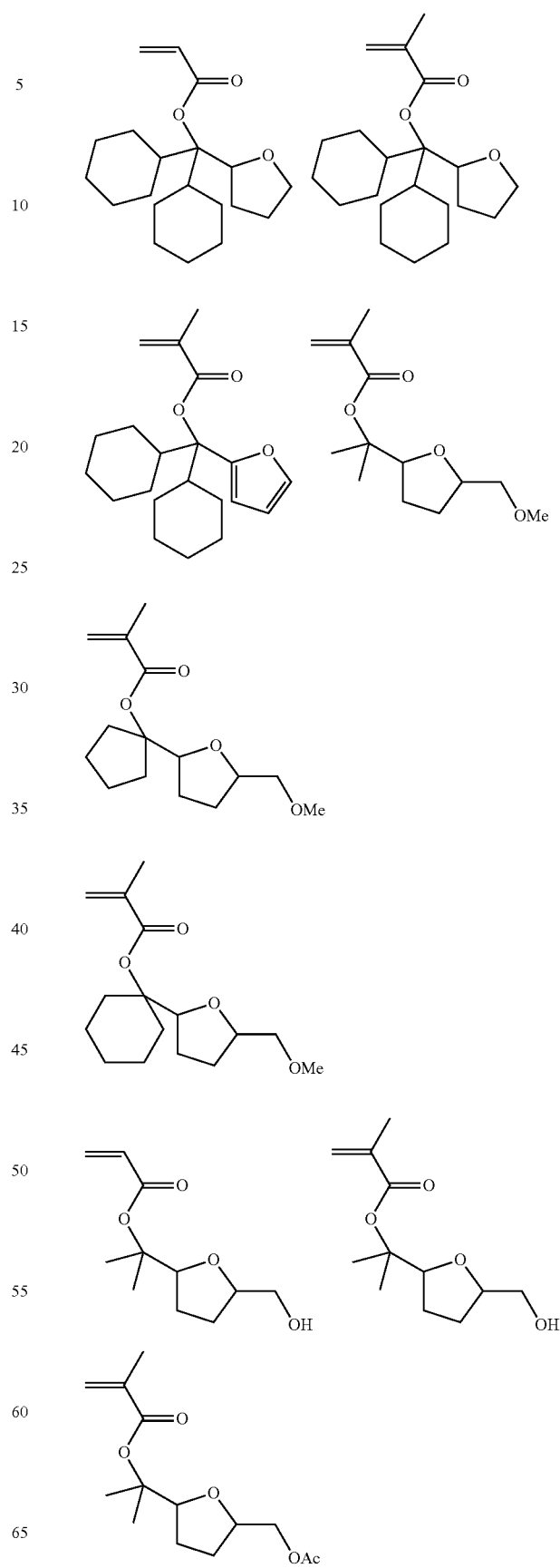

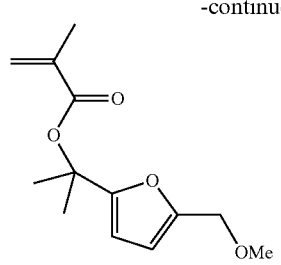
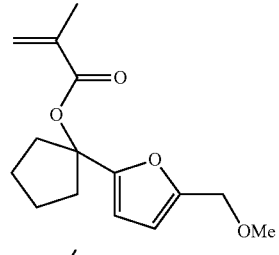
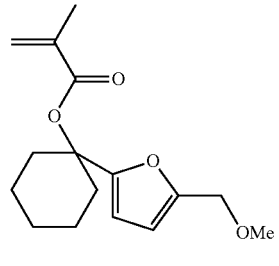
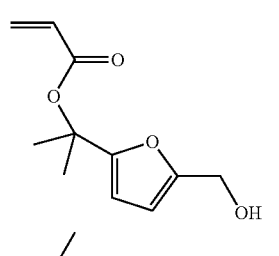
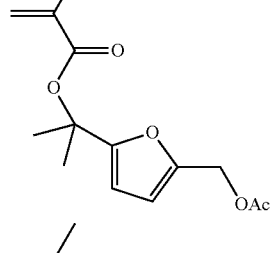
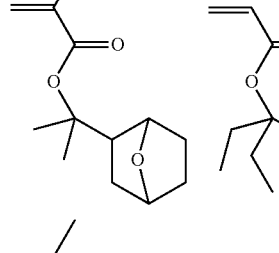
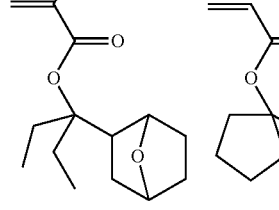
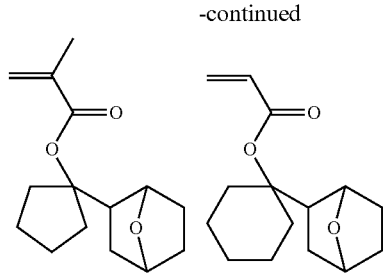
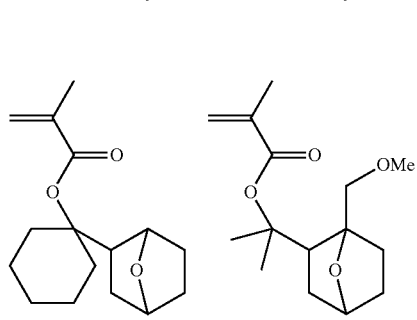
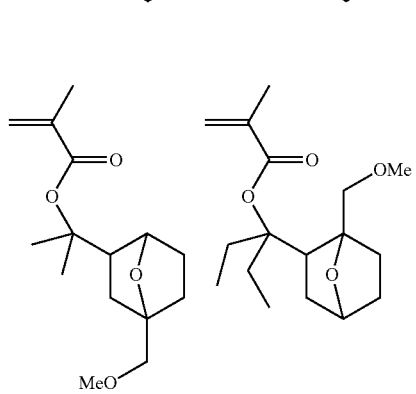
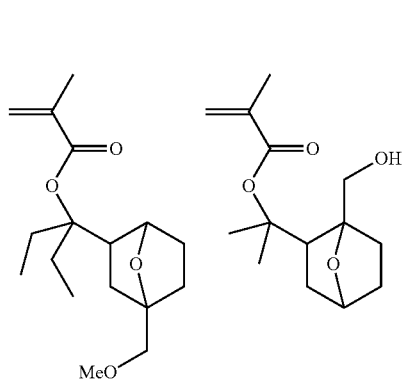
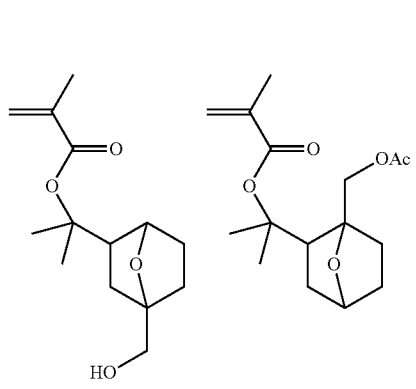

-continued

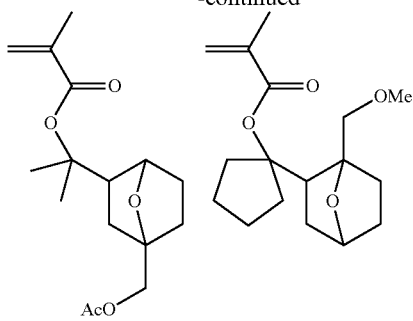
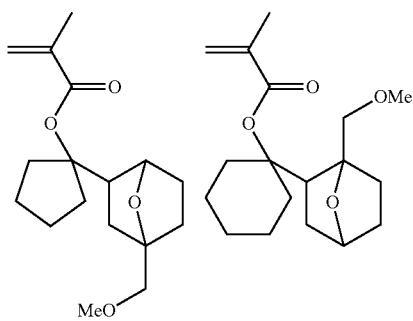
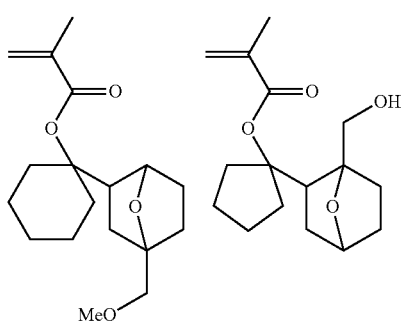
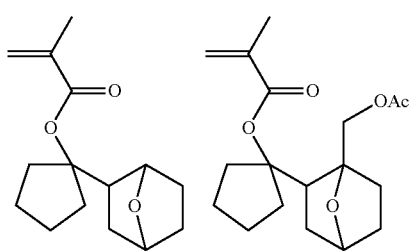
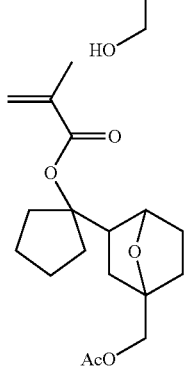

In addition, the acid-labile group $R^{12}$ of the repeating unit a1 may be shown by the general formula (A-23),

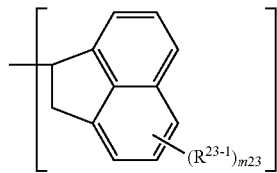

wherein $R^{23-1}$ represents a hydrogen atom, an alkyl group, an alkoxy group, an alkanoyl group, or an alkoxycarbonyl group having 1 to 4 carbon atoms, an aryl group having 6 to 10 carbon atoms, a halogen atom, or a cyano group; and m23 represents an integer of 1 to 4.

Illustrative examples of the monomer to give the repeating unit a1 substituted with the acid-labile group represented by the formula (A-23) include the following compounds.

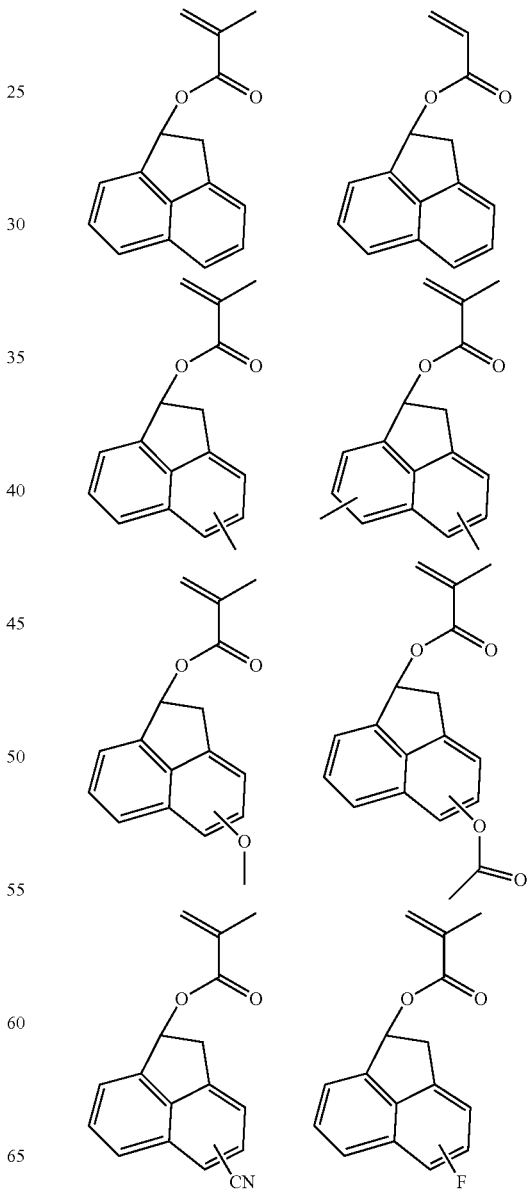

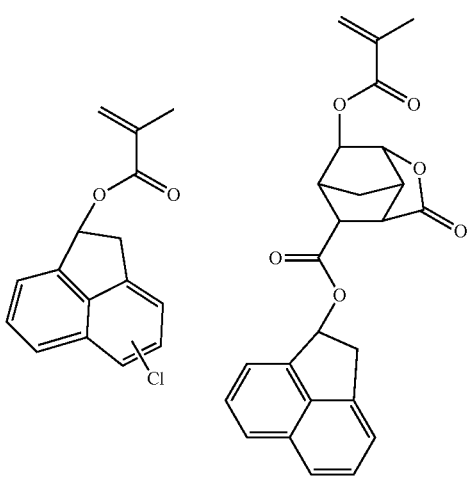
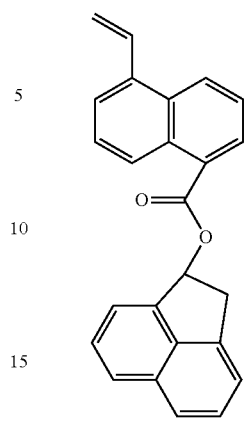
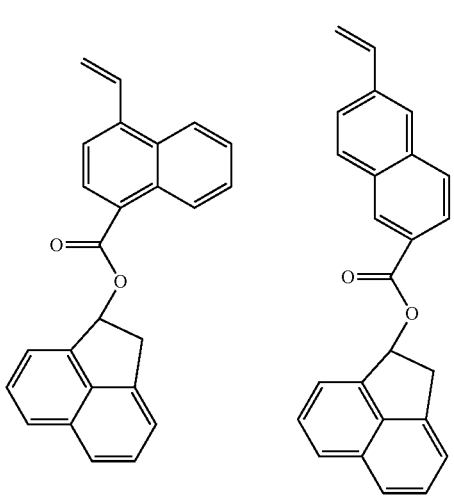

The acid-labile group $R^{12}$ of the repeating unit a1 may be shown by the general formula (A-24),

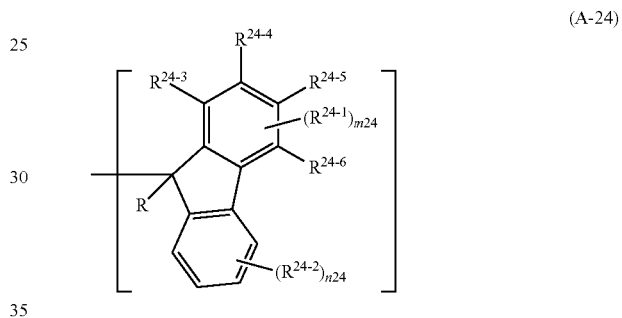

(A-24)

wherein $R^{24-1}$ and $R^{24-2}$ represent a hydrogen atom, an alkyl group, an alkoxy group, an alkanoyl group, or an alkoxycarbonyl group having 1 to 4 carbon atoms, a hydroxyl group, an aryl group having 6 to 10 carbon atoms, a halogen atom, or a cyano group; R represents a hydrogen atom or a linear, branched, or cyclic alkyl group having 1 to 12 carbon atoms and optionally containing an oxygen atom or a sulfur atom, an alkenyl group having 2 to 12 carbon atoms, an alkynyl group having 2 to 12 carbon atoms, an aryl group having 6 to 10 carbon atoms, or a heterocyclic group; $R^{24-3}$, $R^{24-4}$, $R^{24-5}$, and $R^{24-6}$ represent a hydrogen atom; or $R^{24-3}$ and $R^{24-4}$, $R^{24-4}$ and $R^{24-5}$, and $R^{24-5}$ and $R^{24-6}$ may be bonded to form a benzene ring; and m24 and n24 represents an integer of 1 to 4.

Illustrative examples of the monomer to give the repeating unit a1 substituted with the acid-labile group represented by the formula (A-24) include the following compounds.

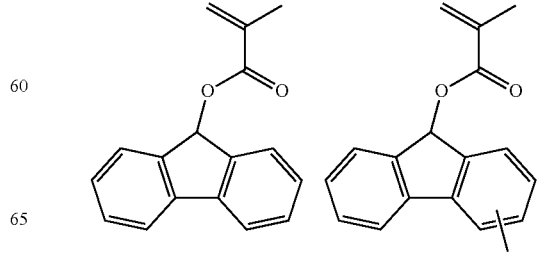

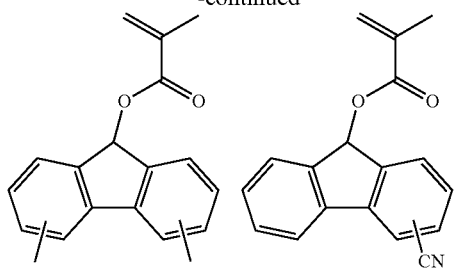
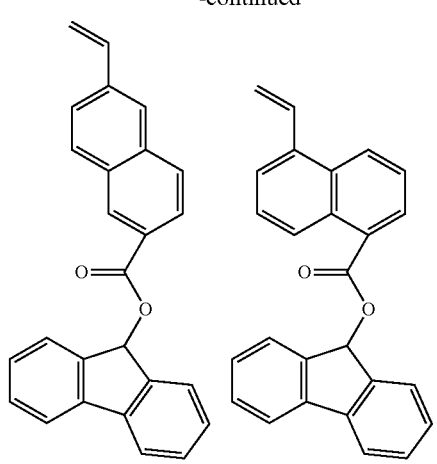
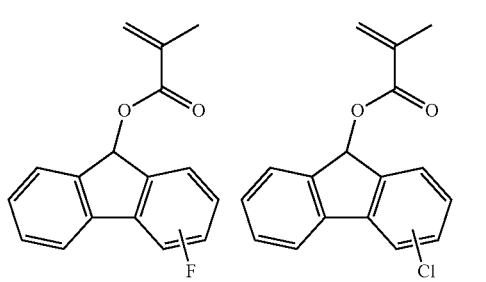
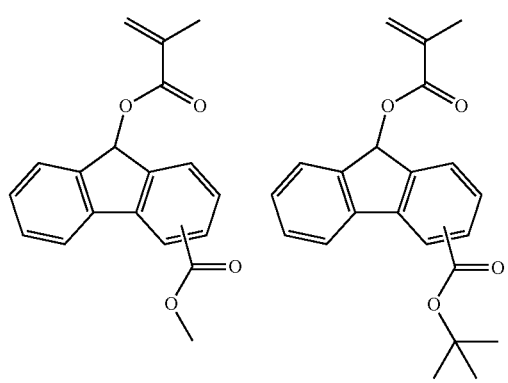
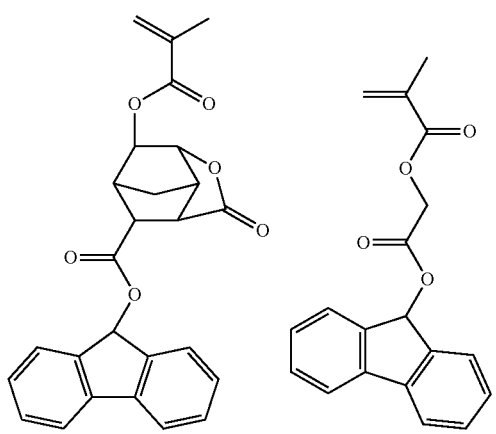
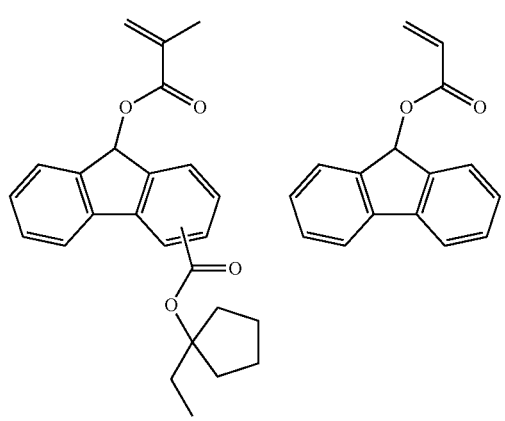
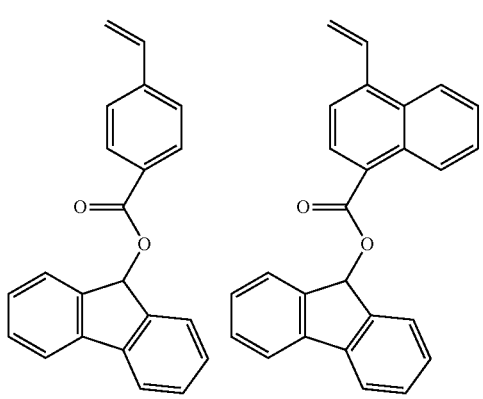
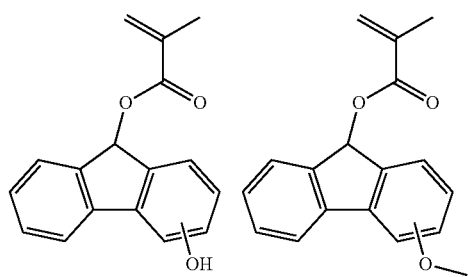

-continued
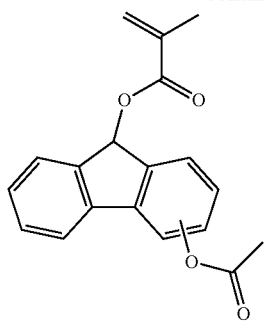
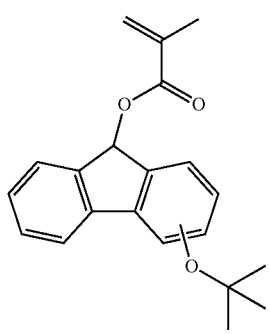
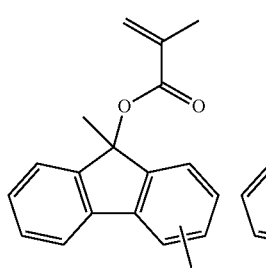
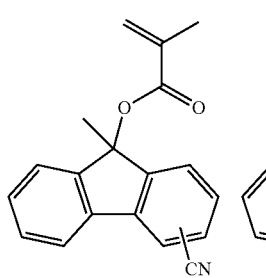
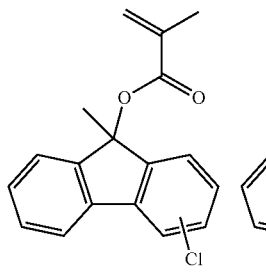
-continued
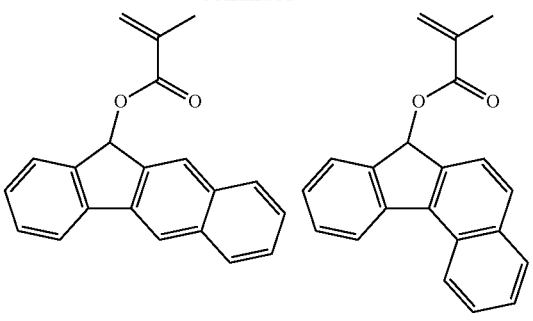
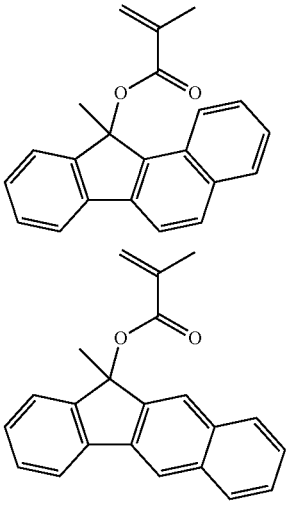
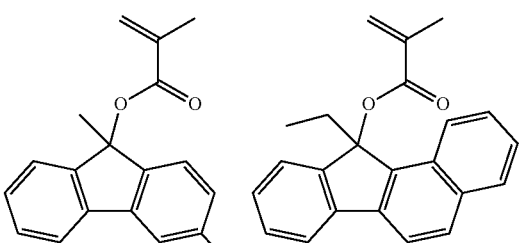
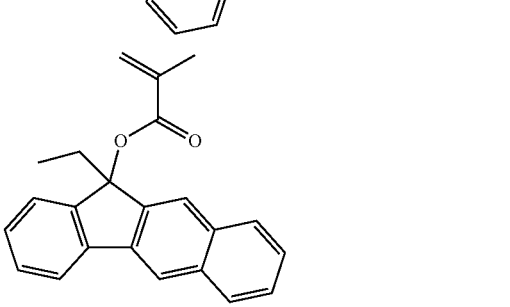
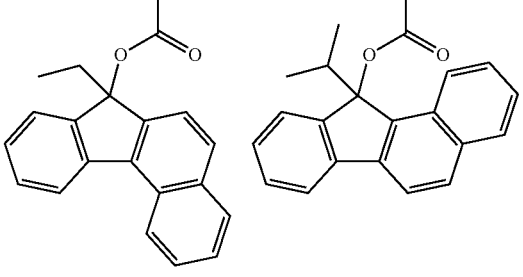

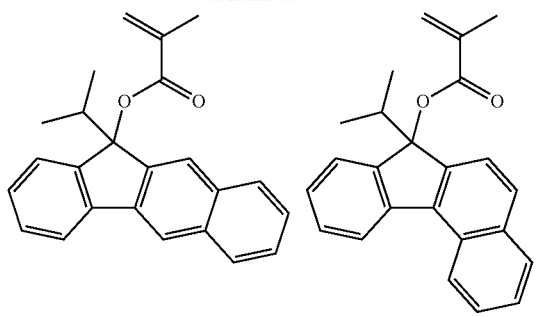
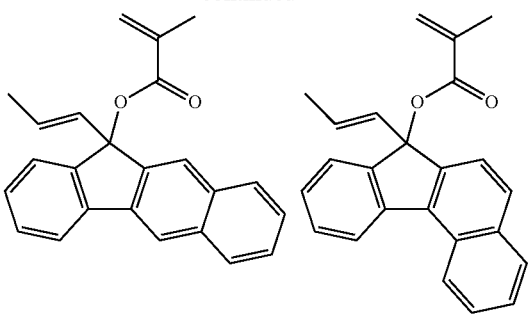
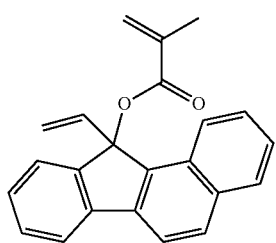
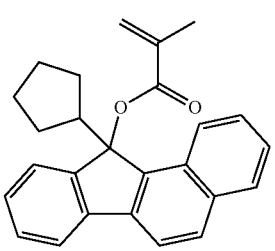
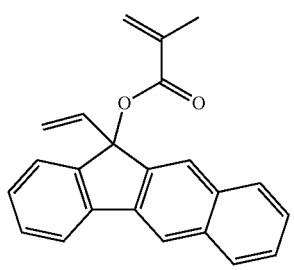
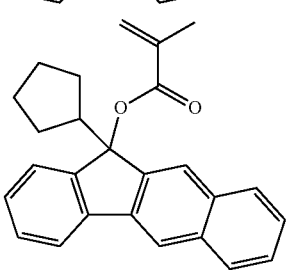
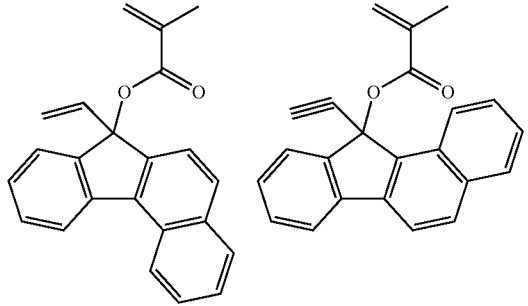
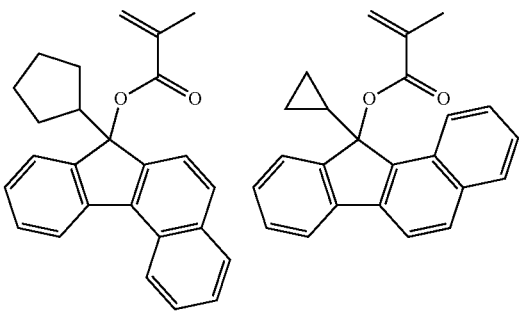
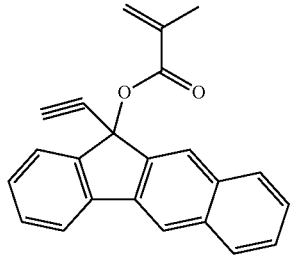
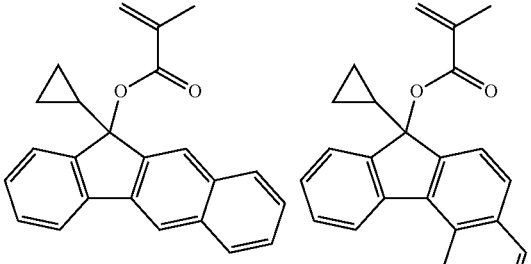
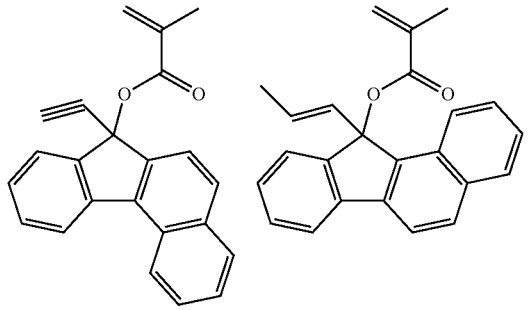
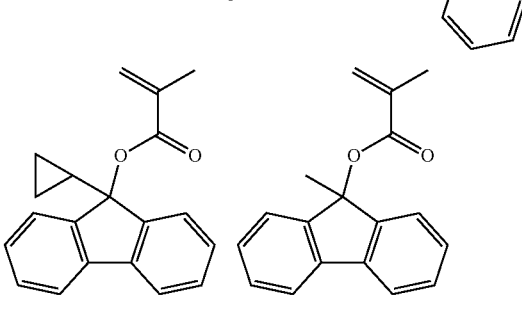

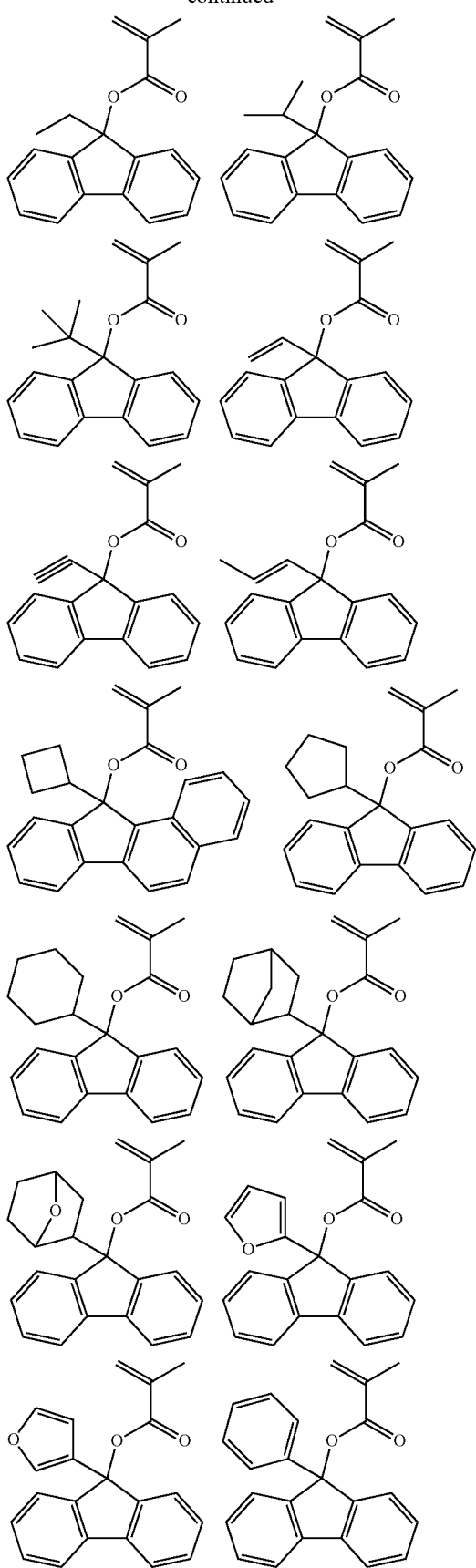
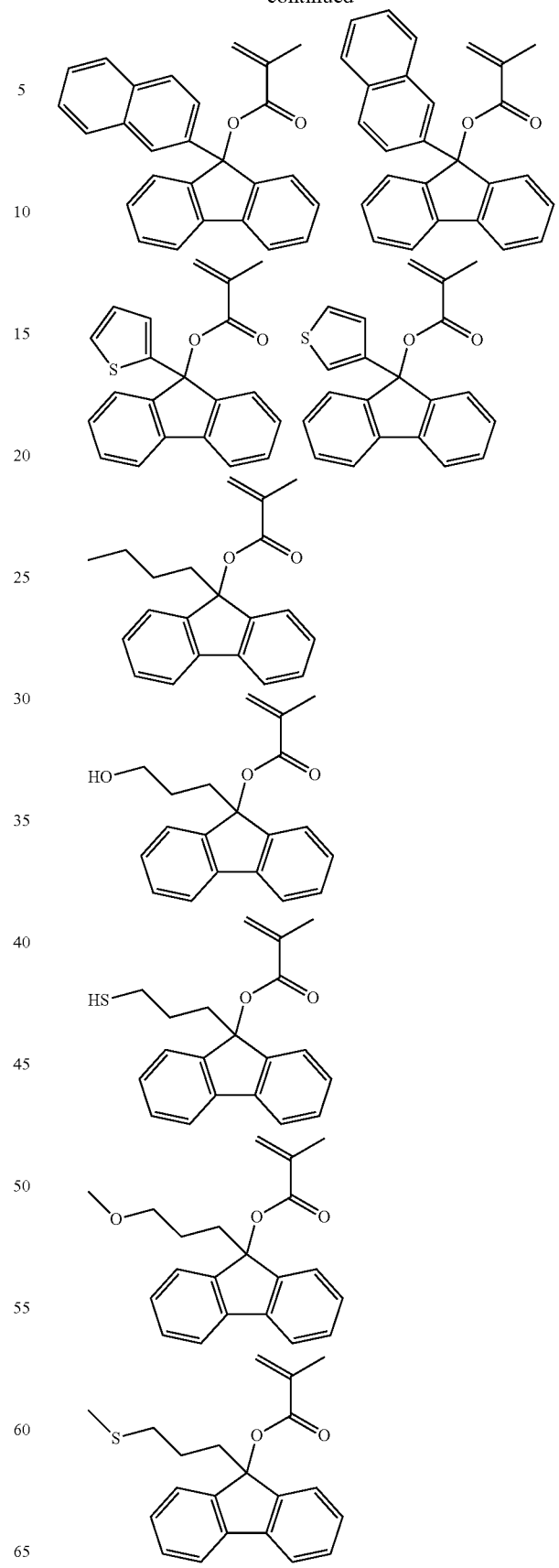

The acid-labile group $R^{12}$ of the repeating unit a1 may be shown by the general formula (A-25),

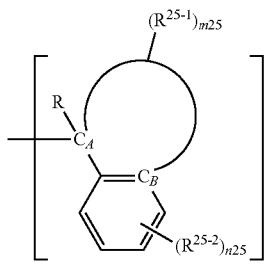

(A-25)

wherein each $R^{25-1}$ may be the same or different and represents a hydrogen atom or a linear, branched, or cyclic alkyl group having 1 to 6 carbon atoms; and when m25 is 2 or more, $R^{25-1}$ may be bonded with each other to form a non-aromatic ring having 2 to 8 carbon atoms; the circle represents a bond between $C_A$ and $C_B$, selected from an ethylene group, a propylene group, a butylene group, and a pentalene group; $R^{25-2}$ represents a hydrogen atom, an alkyl group, an alkoxy group, an alkanoyl group, an alkoxycarbonyl group having 1 to 4 carbon atoms, a hydroxyl group, a nitro group, an aryl group having 6 to 10 carbon atoms, a halogen atom, or a cyano group; R has the same meaning as above; when the circle is an ethylene group or a propylene group, $R^{25-1}$ cannot be a hydrogen atom; and m25 and n25 represent an integer of 1 to 4.

Illustrative examples of the monomer to give the repeating unit a1 substituted with the acid-labile group represented by the formula (A-25) include the following compounds.

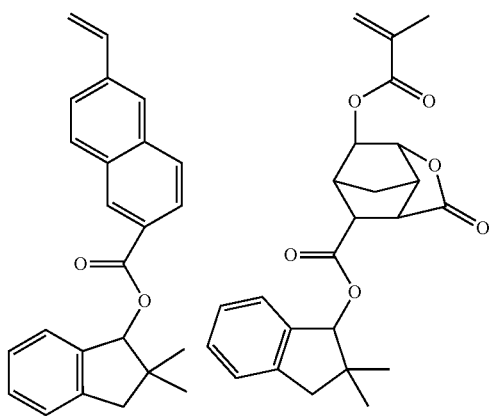

-continued

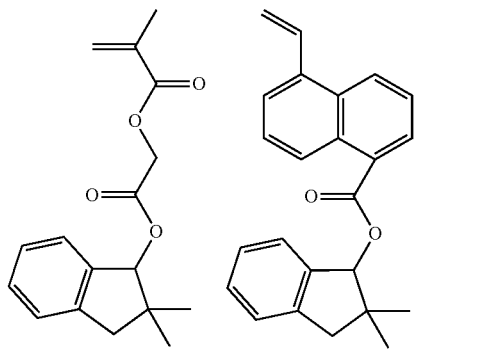

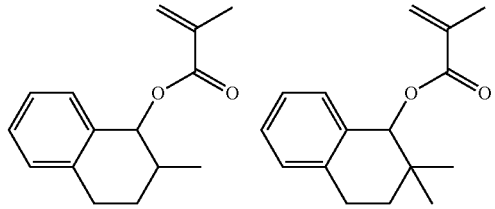

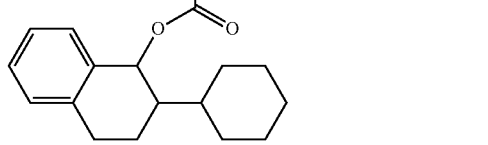

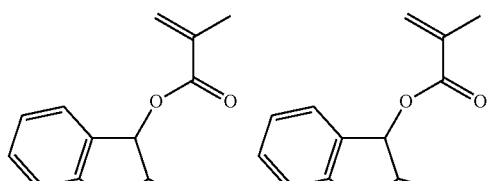

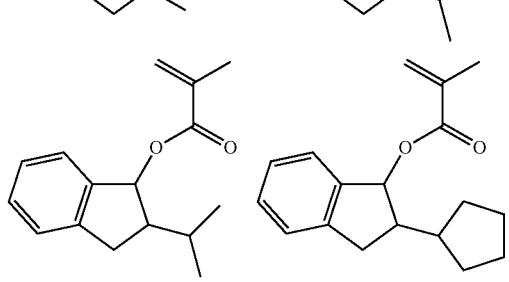

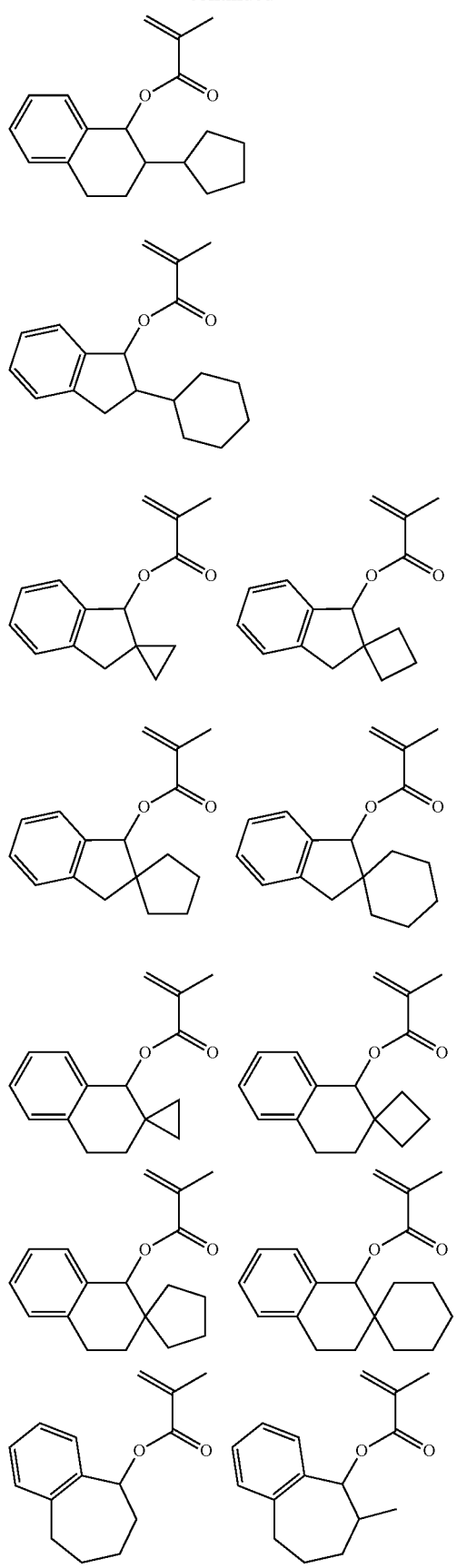
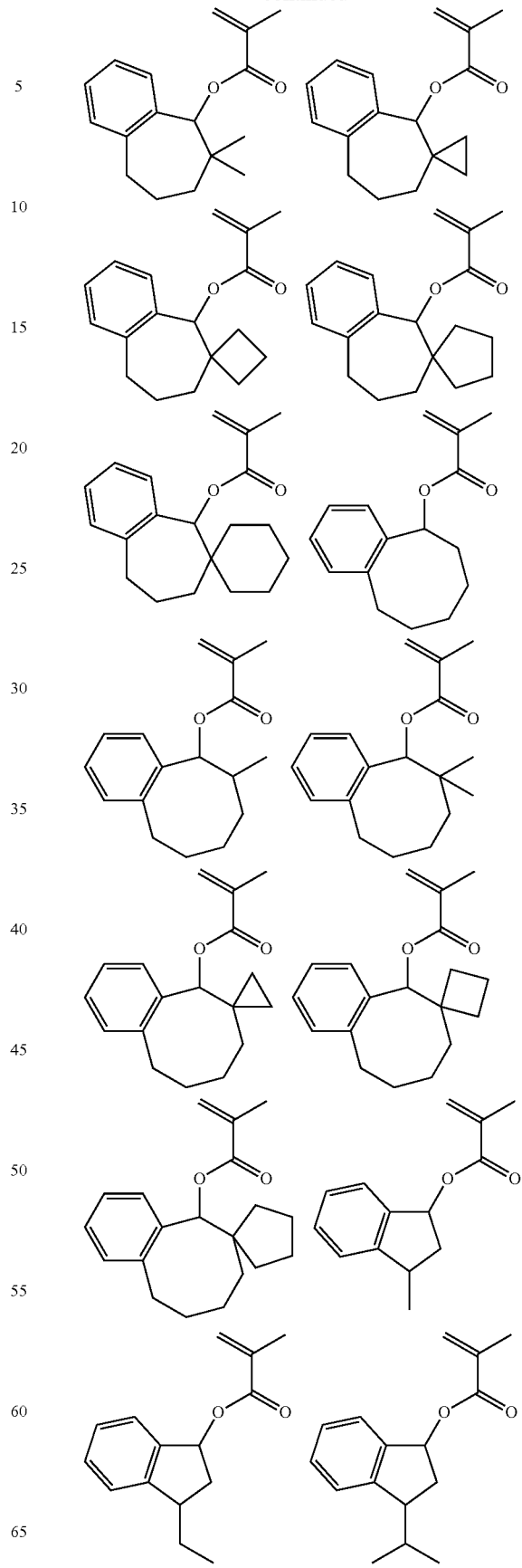

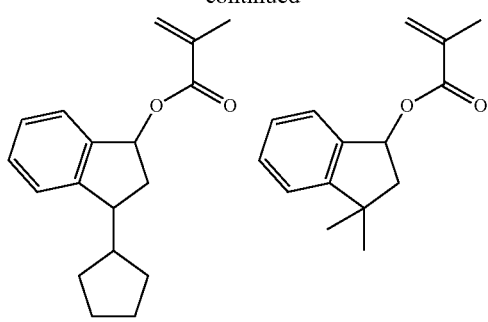
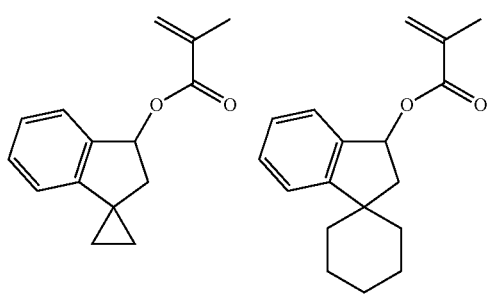
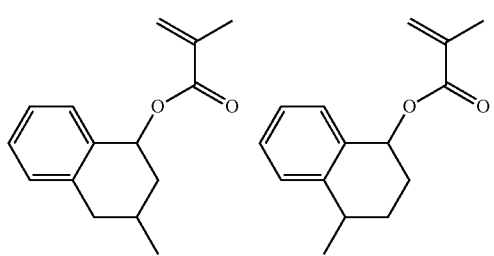
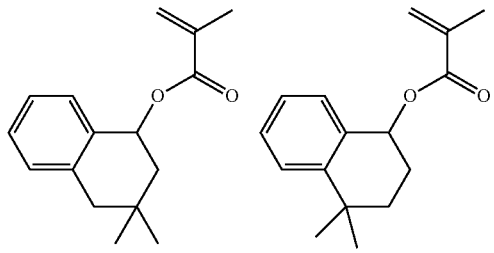
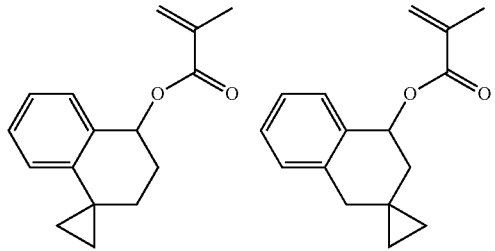
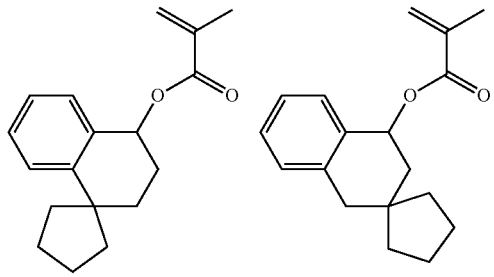
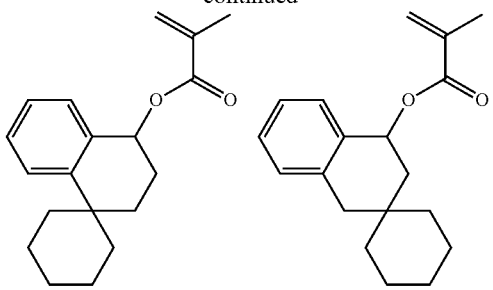
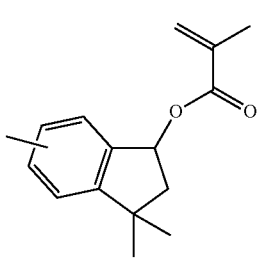
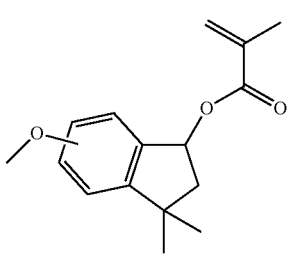
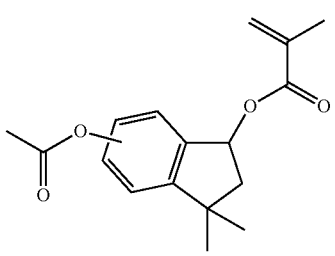
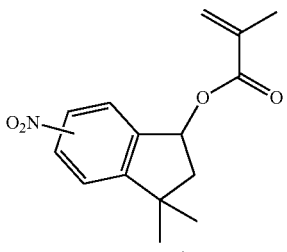
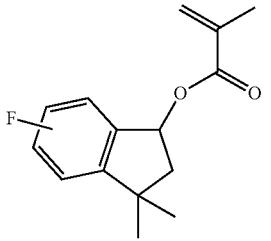

55
-continued
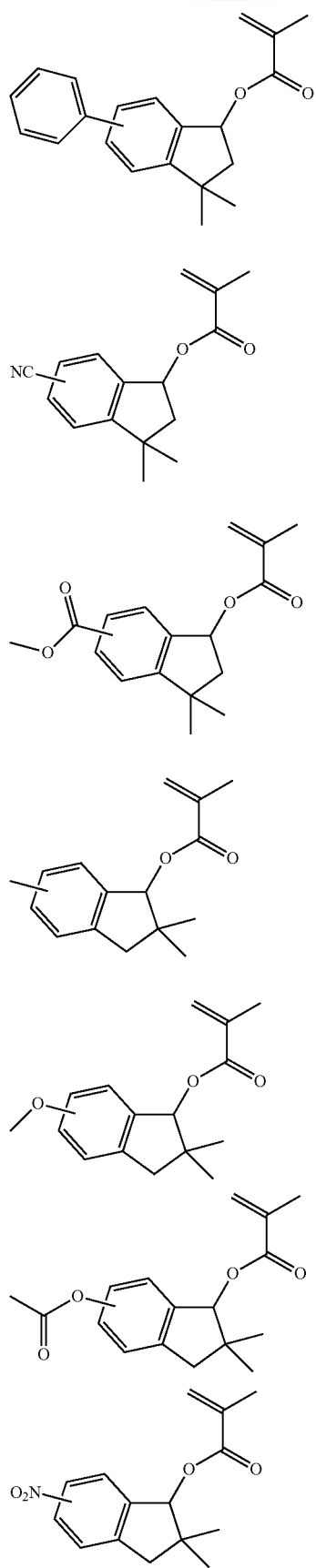
56
-continued
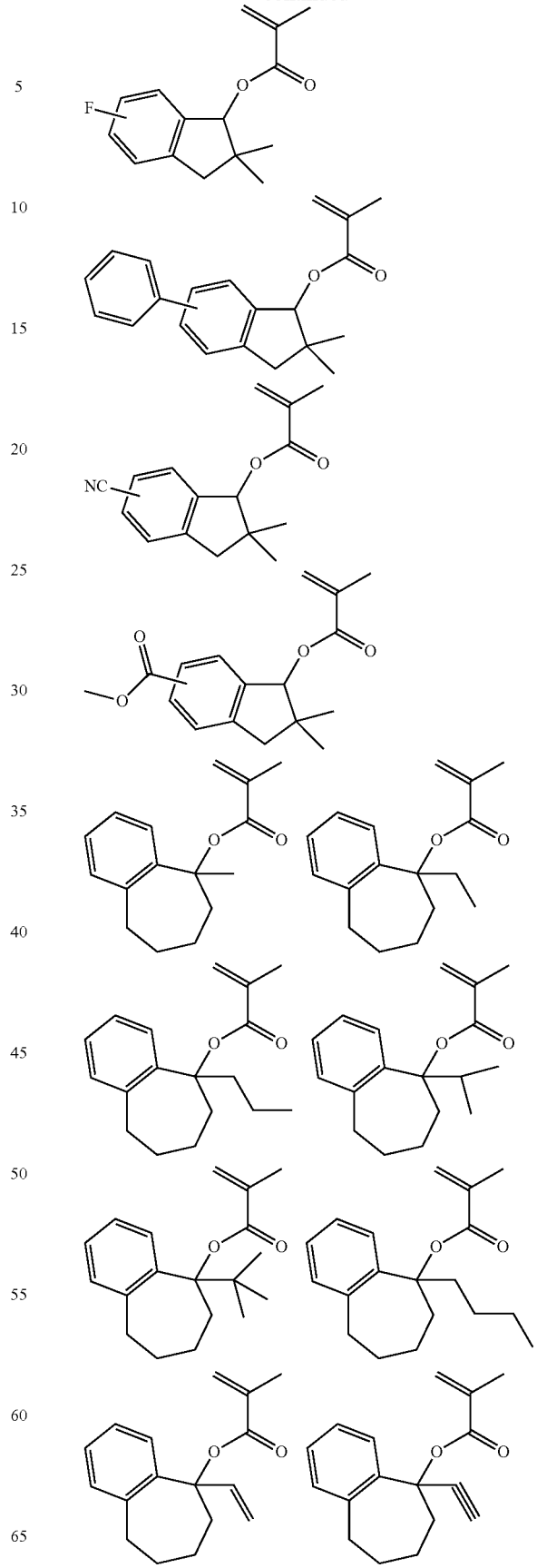

-continued
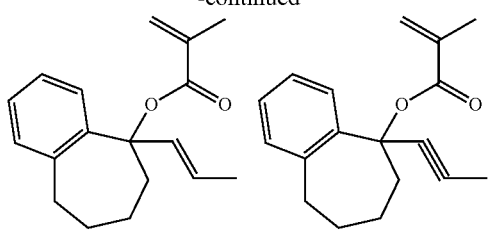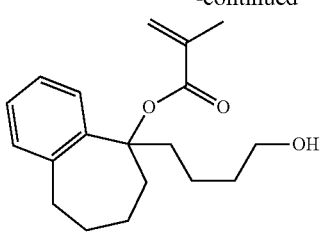
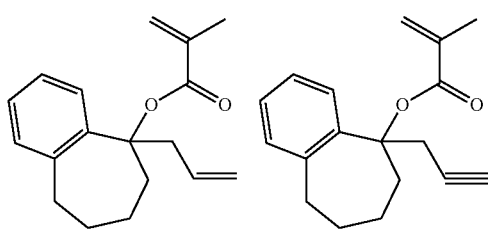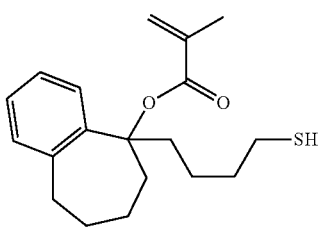
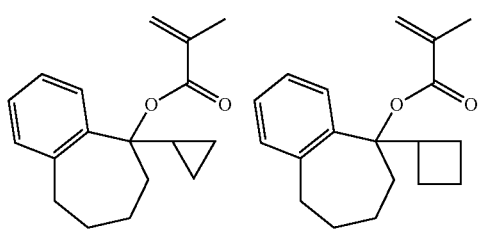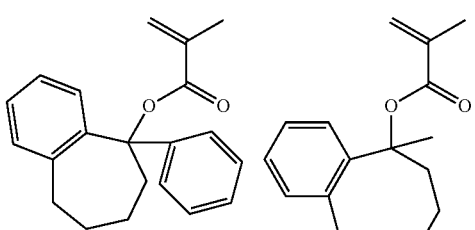
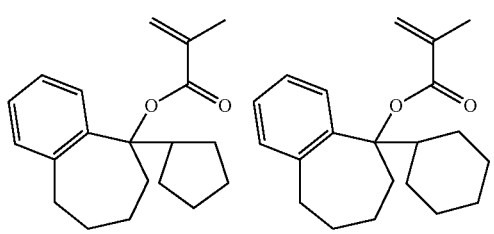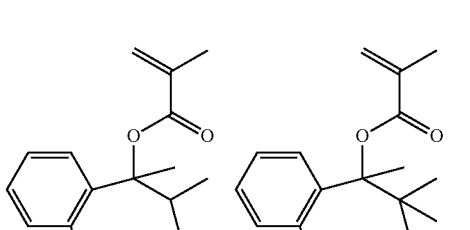
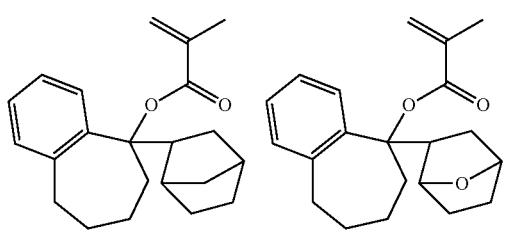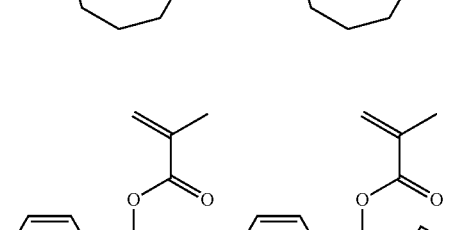
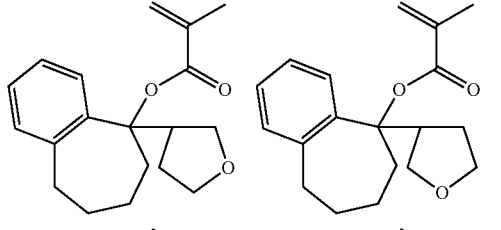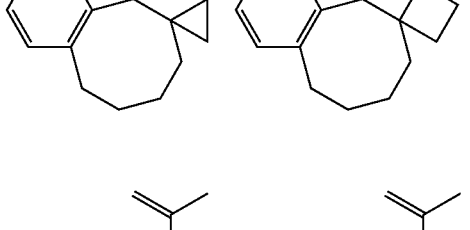
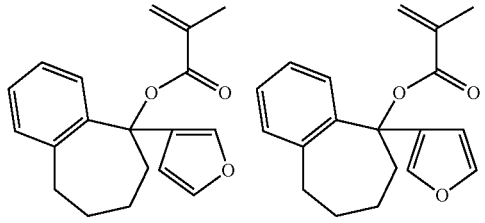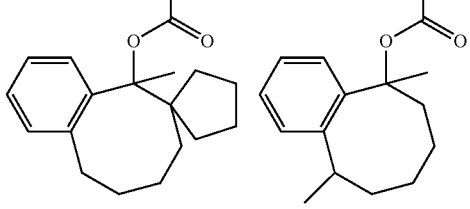

-continued
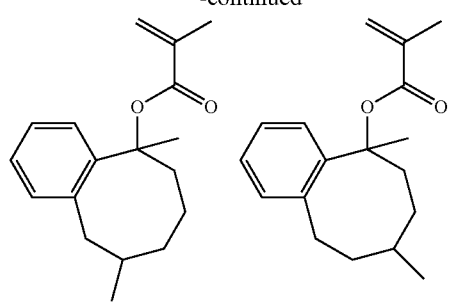
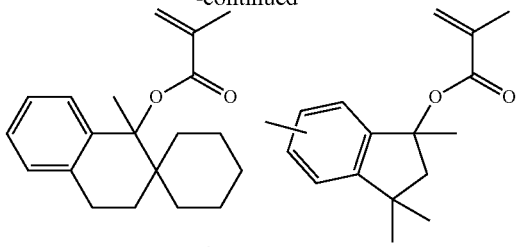
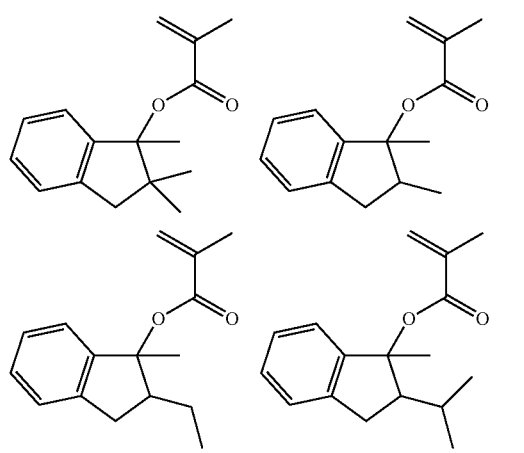
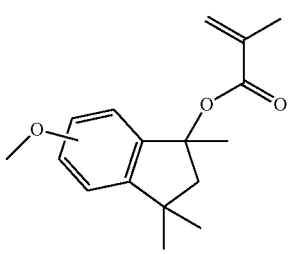
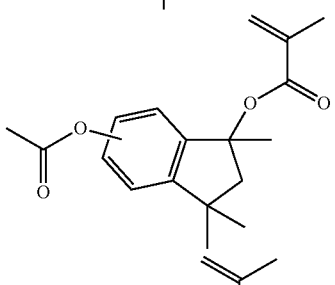
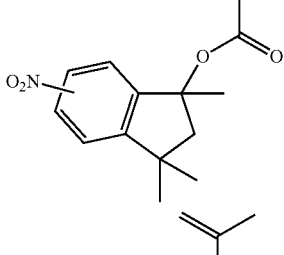
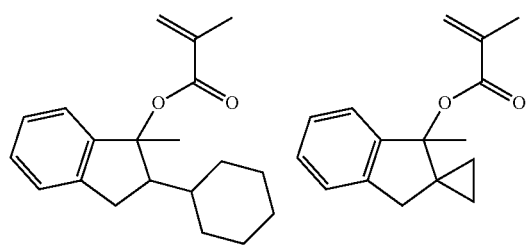
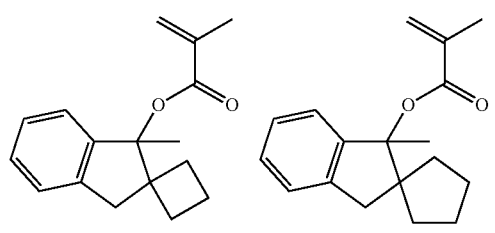
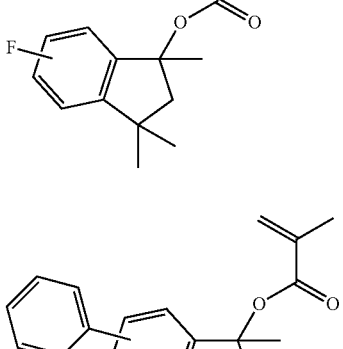
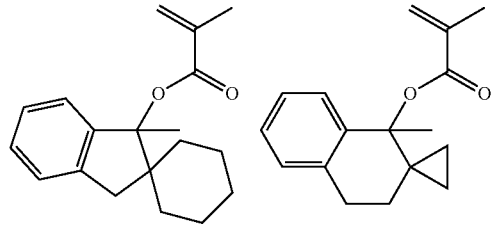
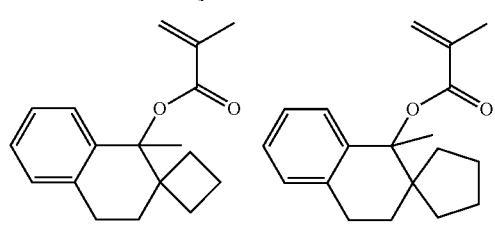
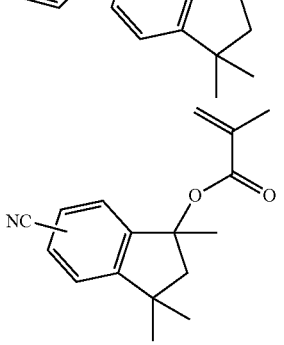

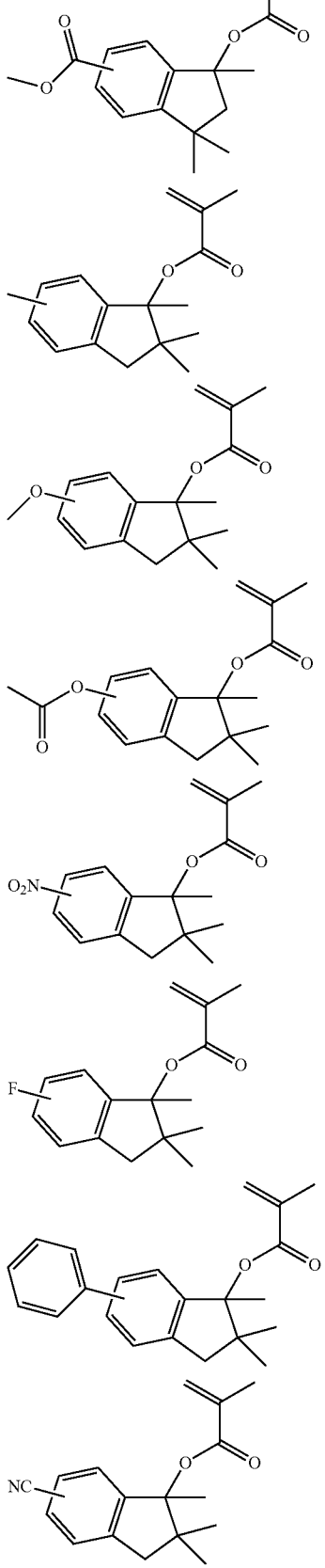

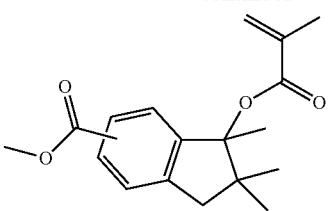

The acid-labile group $R^{12}$ of the repeating unit a1 may be shown by the general formula (A-26),

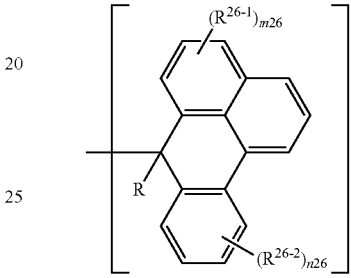

(A-26)

wherein $R^{26-1}$ and $R^{26-2}$ represent a hydrogen atom, an alkyl group, an alkoxy group, an alkanoyl group, or an alkoxycarbonyl group having 1 to 4 carbon atoms, a hydroxyl group, a nitro group, an aryl group having 6 to 10 carbon atoms, a halogen atom, or a cyano group. R has the same meaning as above; and m26 and n26 represent an integer of 1 to 4.

Illustrative examples of the monomer to give the repeating unit a1 substituted with the acid-labile group represented by the formula (A-26) include the following compounds.

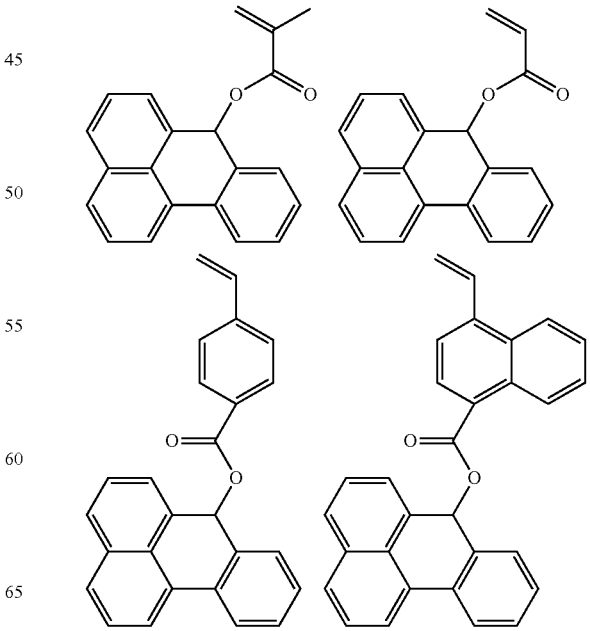

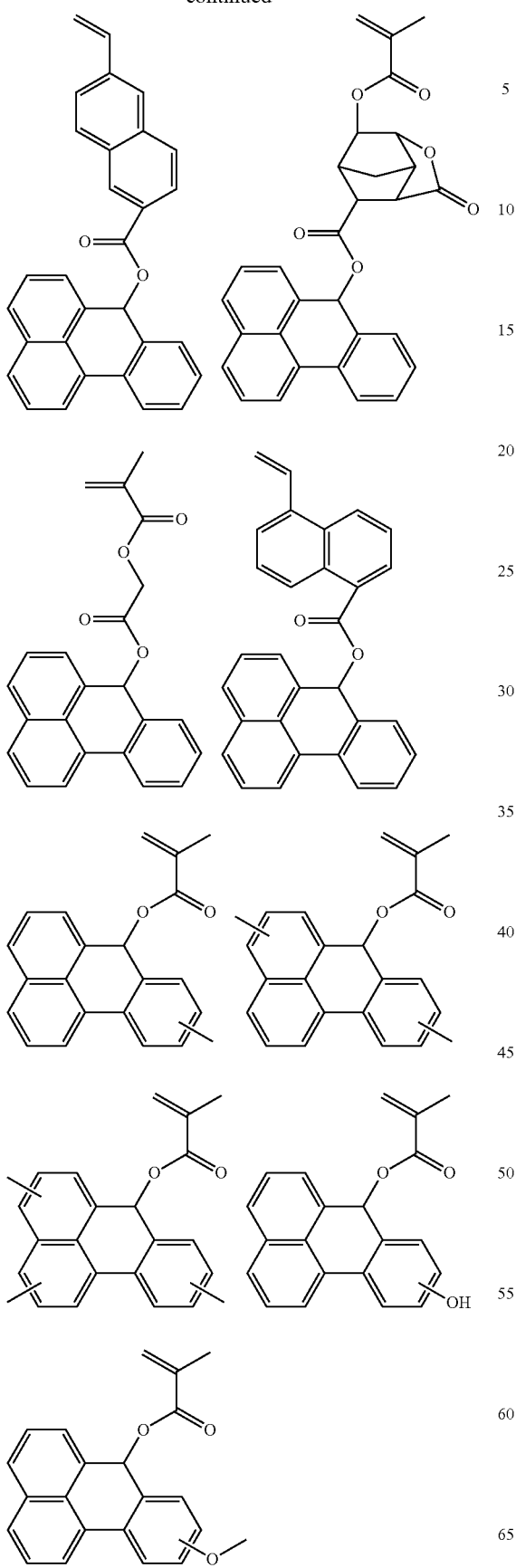
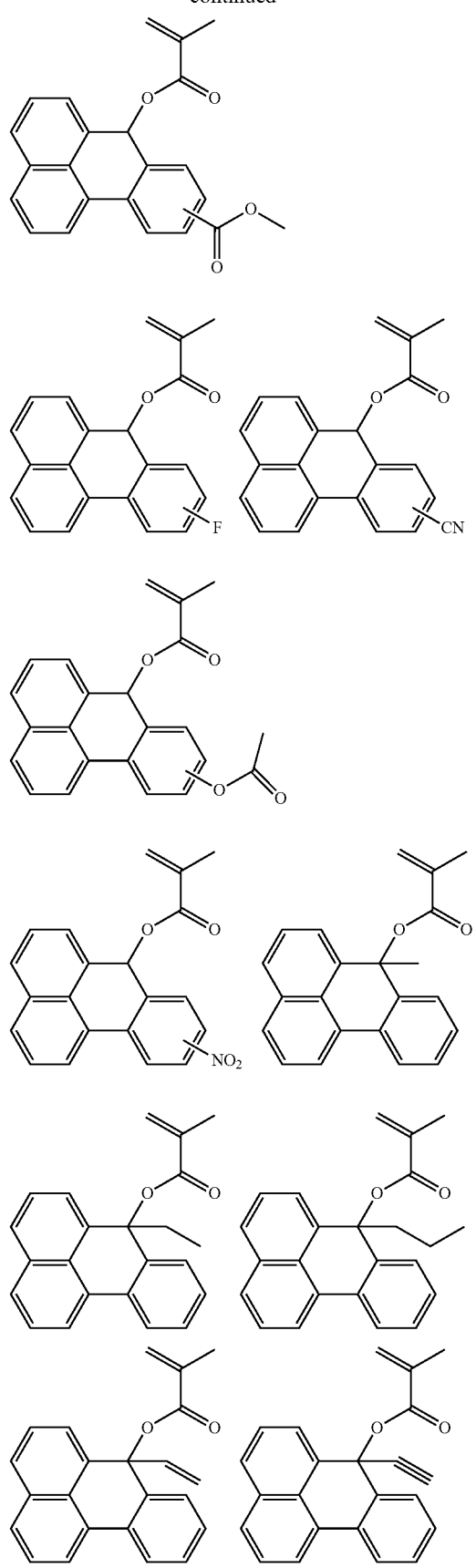

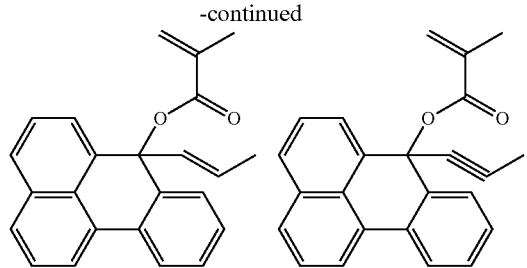
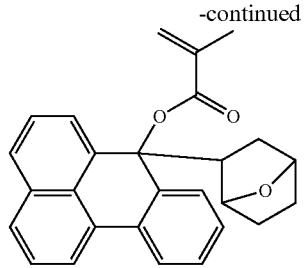
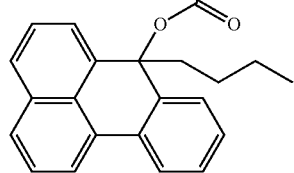
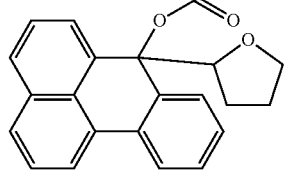
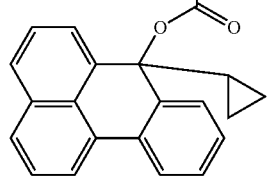
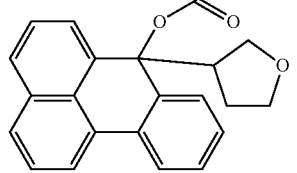
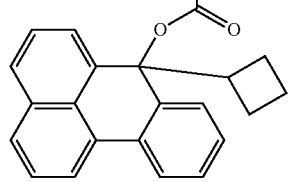
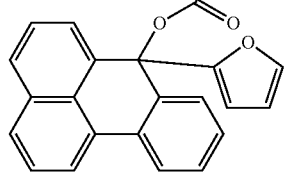
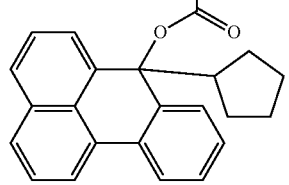
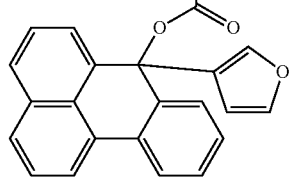
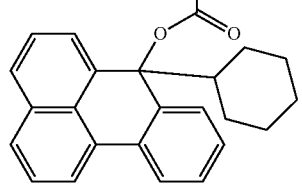
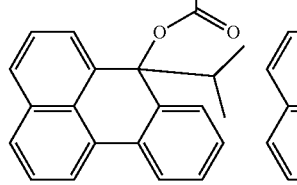
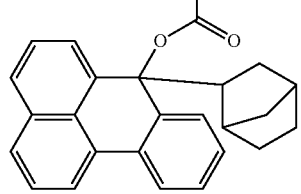
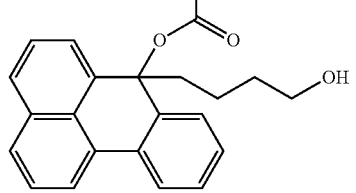

-continued

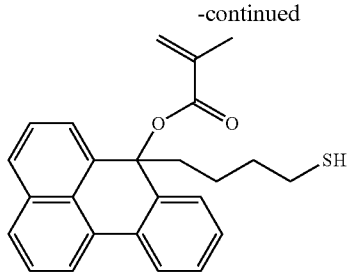
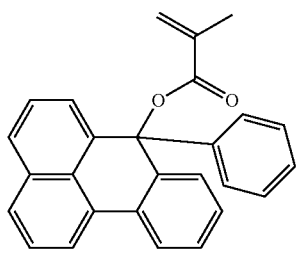
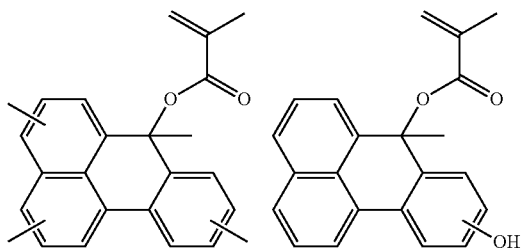
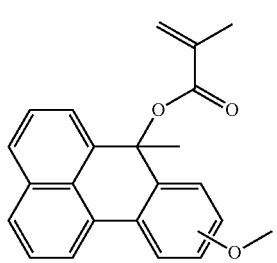
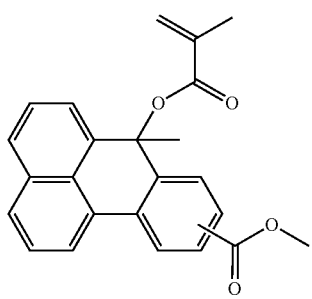
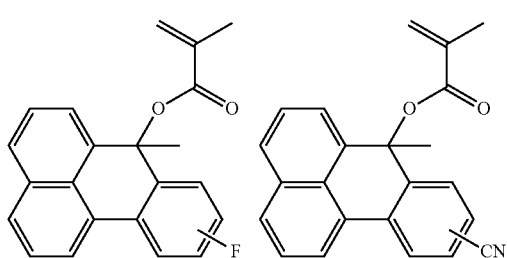

-continued

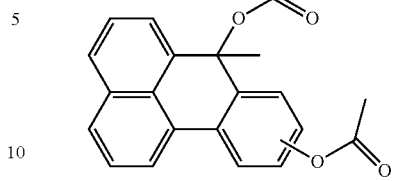
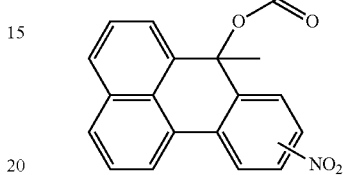

The acid-labile group $R^{12}$ of the repeating unit a1 may be shown by the general formula (A-27),

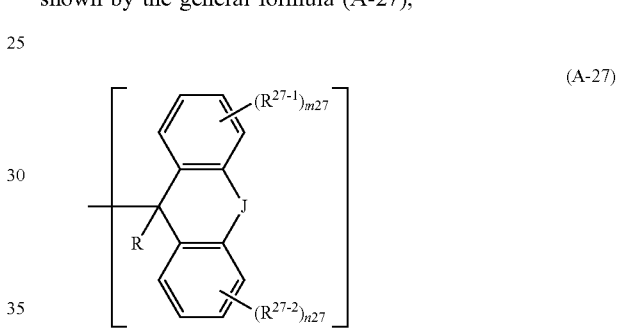

(A-27)

wherein $R^{27-1}$ and $R^{27-2}$ represent a hydrogen atom, an alkyl group, an alkoxy group, an alkanoyl group, an alkoxycarbonyl group having 1 to 4 carbon atoms, a hydroxyl group, an aryl group having 6 to 10 carbon atoms, a halogen atom, or a cyano group; R has the same meaning as above; m27 and n27 represent an integer of 1 to 4; and "J" represents a methylene group, an ethylene group, a vinylene group, or —CH$_2$—S—.

Illustrative examples of the monomer to give the repeating unit a1 substituted with the acid-labile group represented by the formula (A-27) include the following compounds.

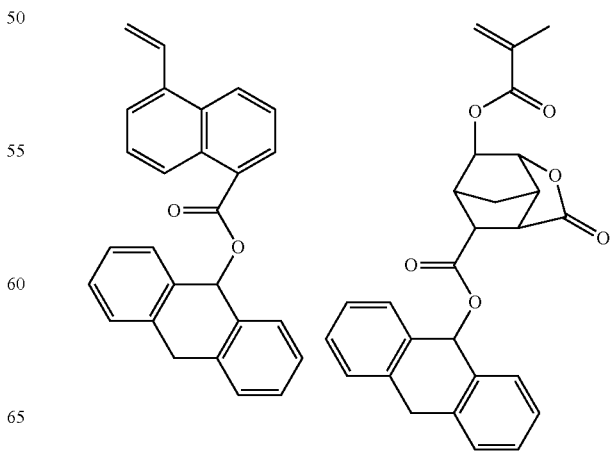

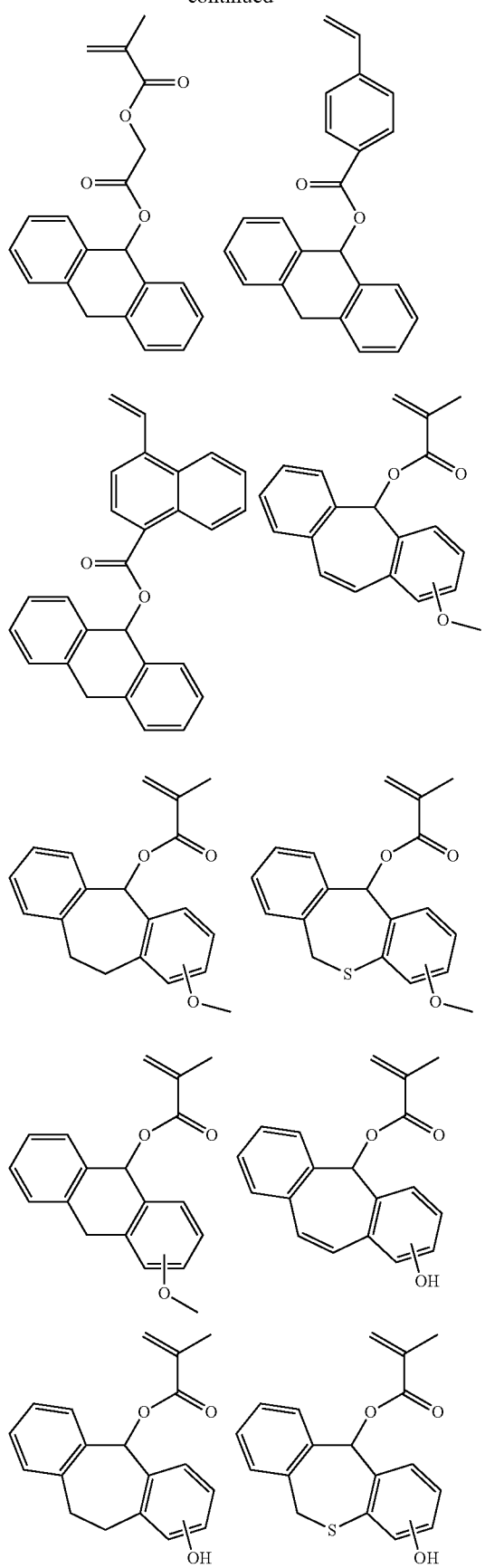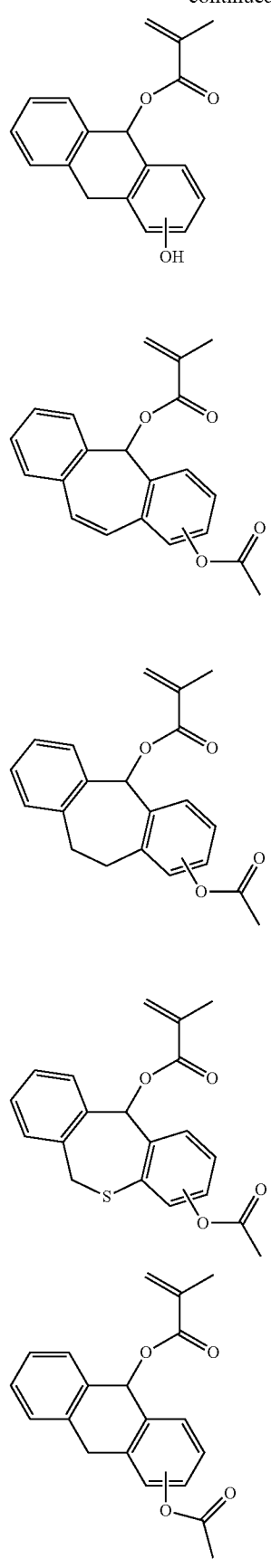

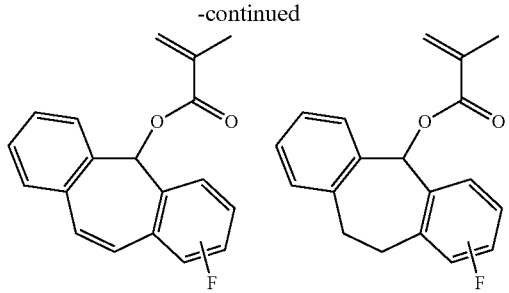
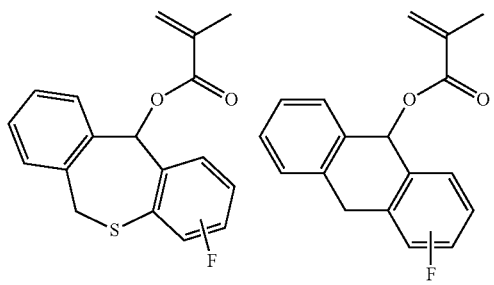
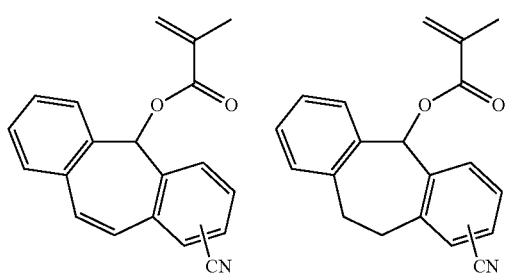
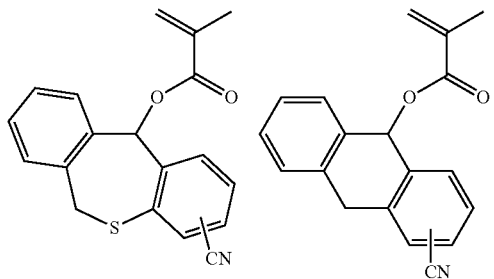
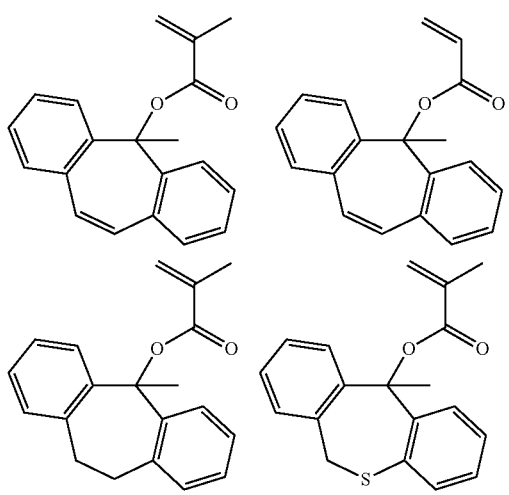
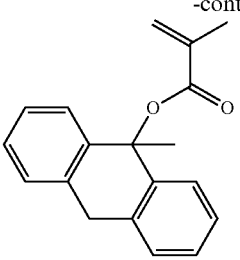
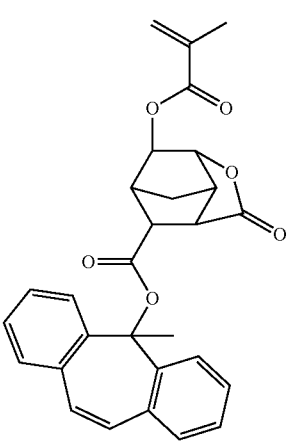
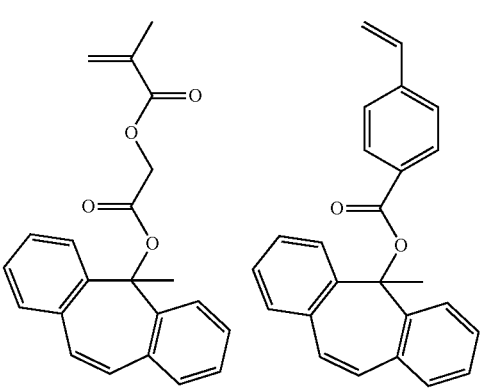
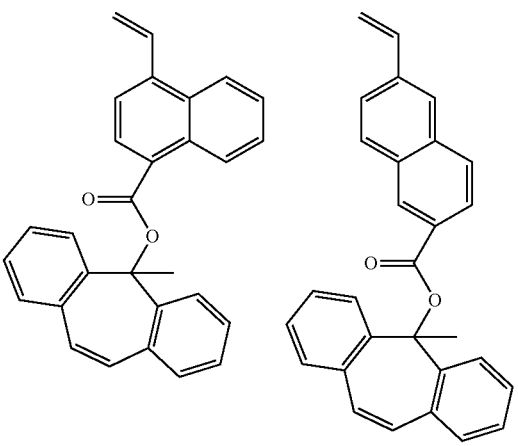

73
-continued
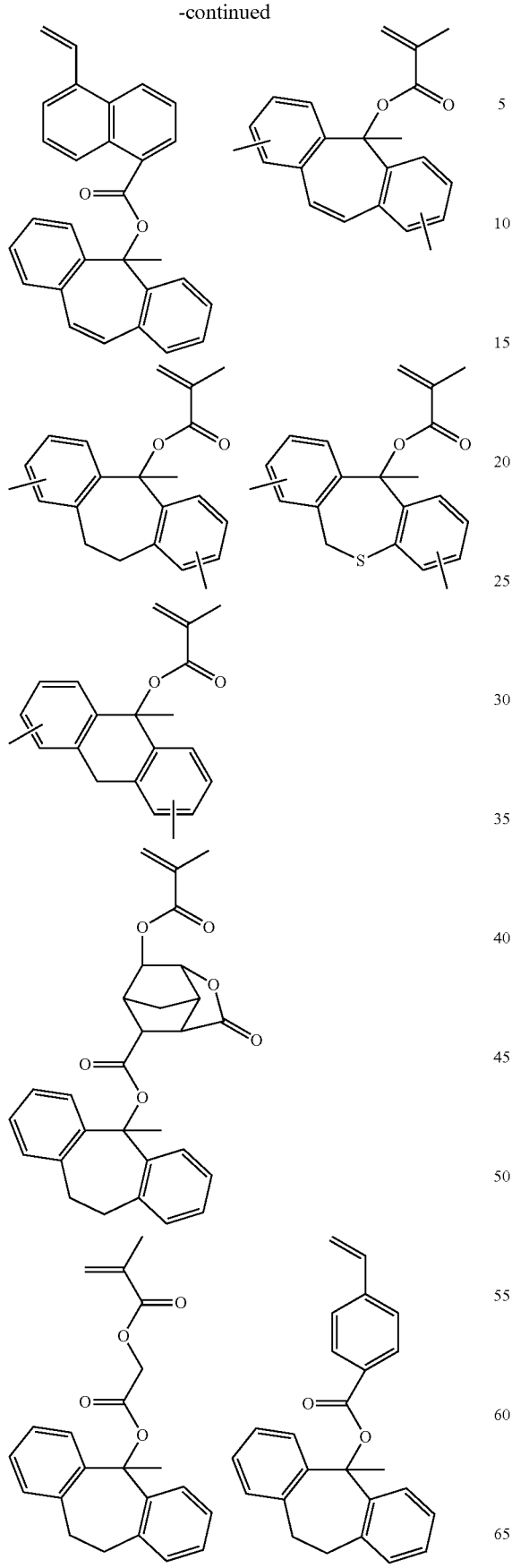
74
-continued
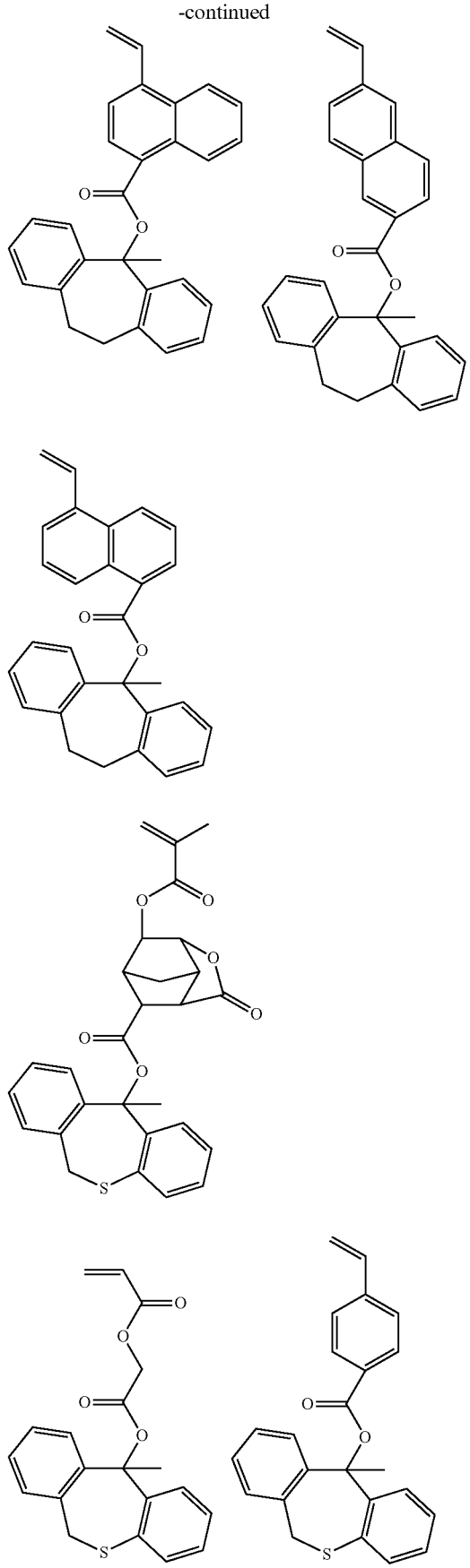

-continued
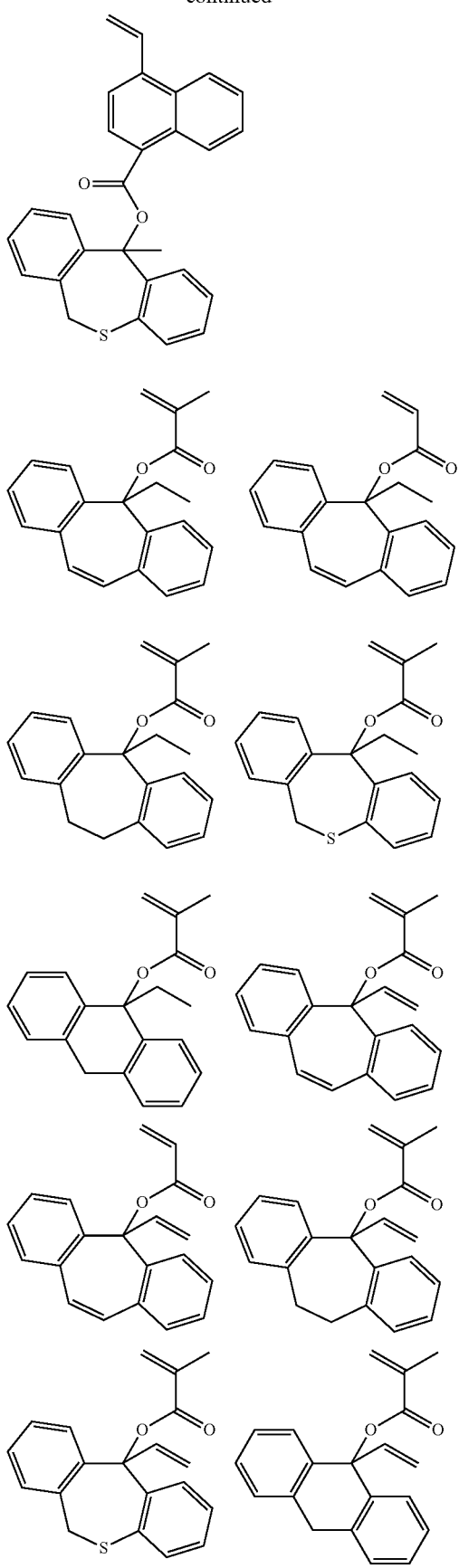
-continued
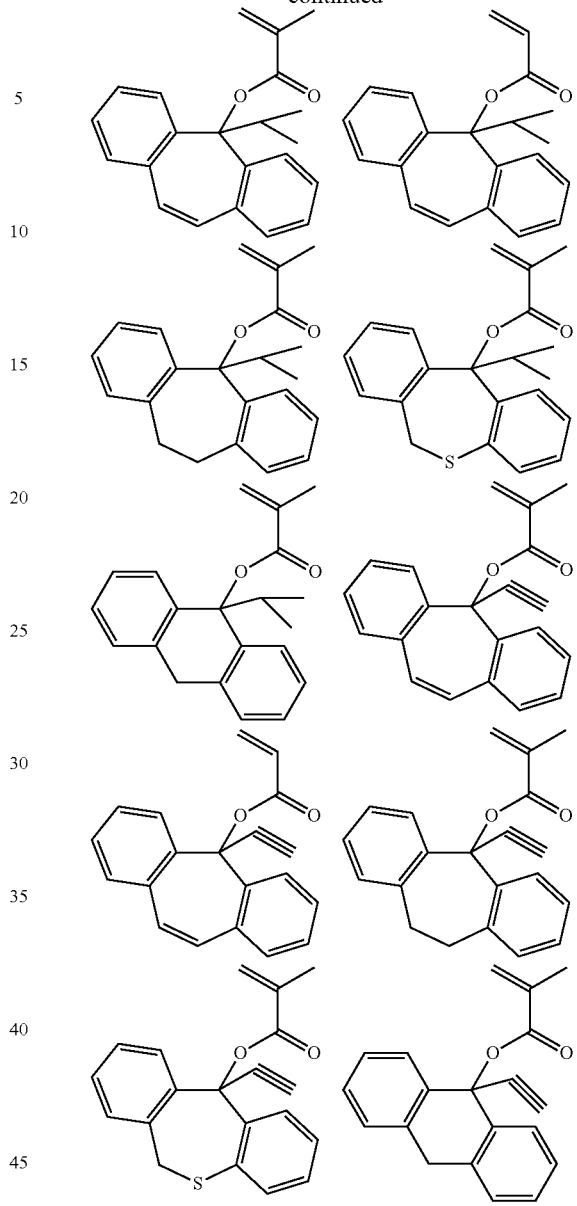
The acid-labile group $R^{12}$ of the repeating unit a1 may be shown by the general formula (A-28),
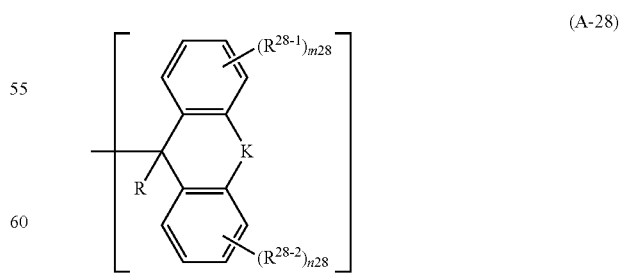
wherein $R^{28-1}$ and $R^{28-2}$ represent a hydrogen atom, an alkyl group, an alkoxy group, an alkanoyl group, or an alkoxycarbonyl group having 1 to 4 carbon atoms, a hydroxyl group, an aryl group having 6 to 10 carbon atoms, a halogen atom, a nitro group, or a cyano group. R has the same meaning as above; m28 and n28 represent an integer of 1 to 4; and K represents a carbonyl group, an ether group, a sulfide group, —S(=O)—, or —S(=O)$_2$—.
Illustrative examples of the monomer to give the repeating unit a1 substituted with the acid-labile group represented by the formula (A-28) include the following compounds.
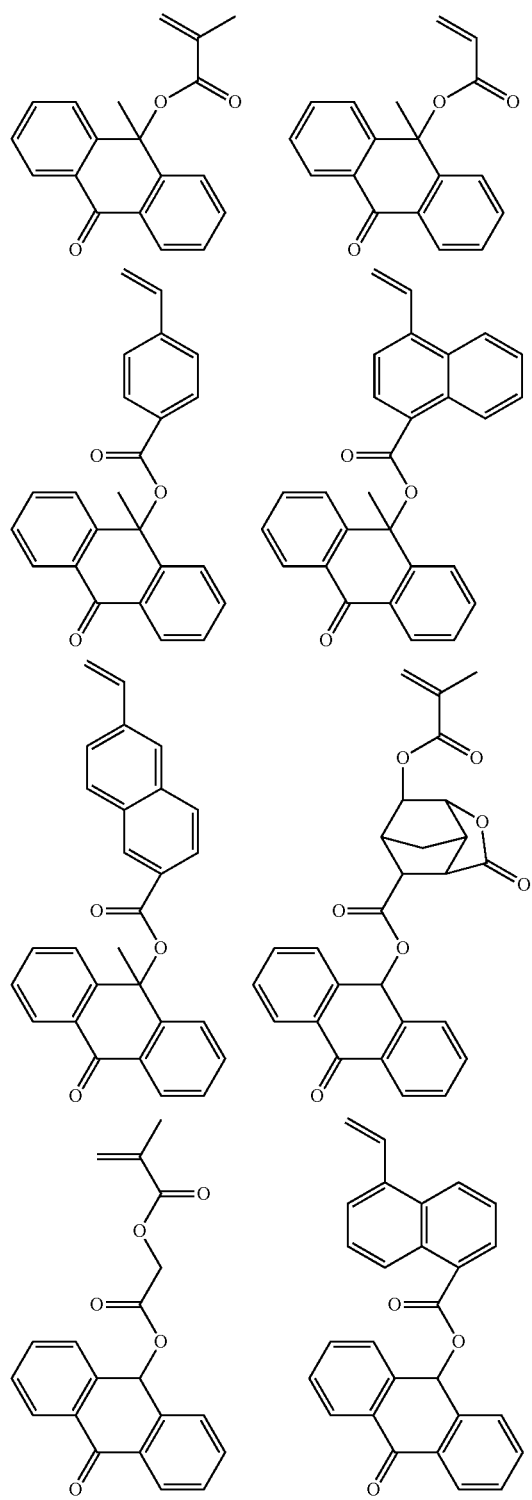
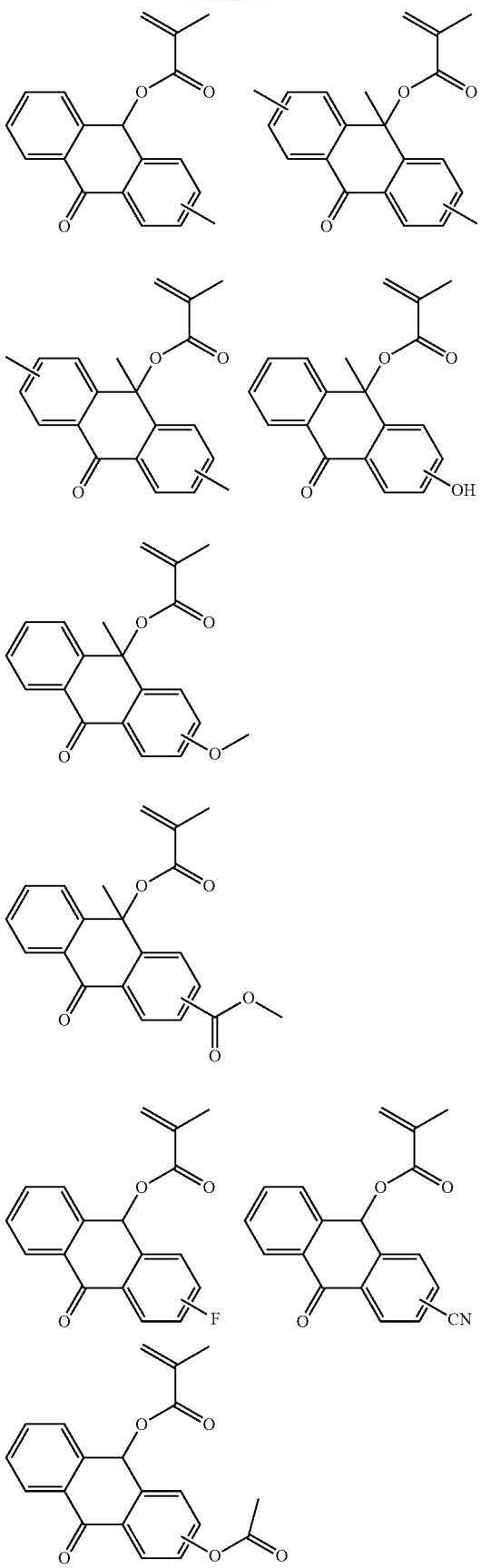

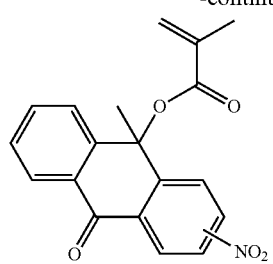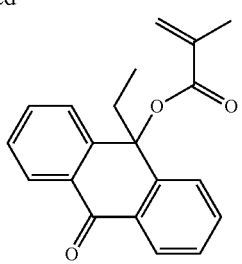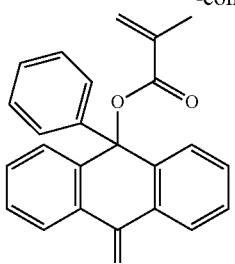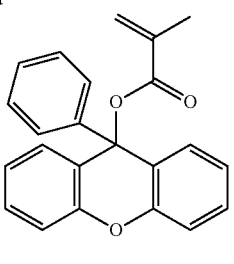
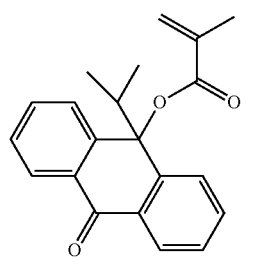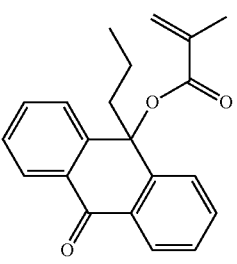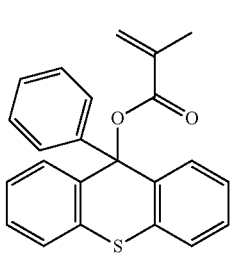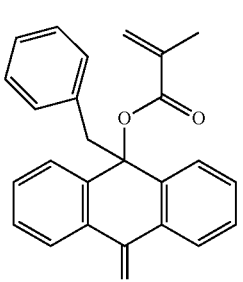
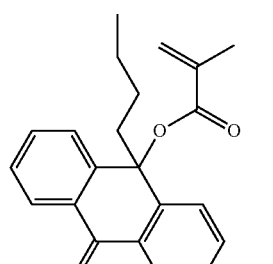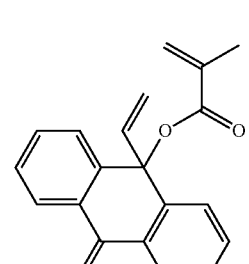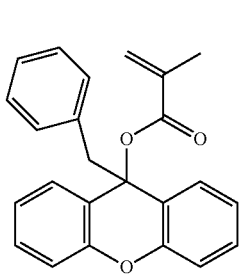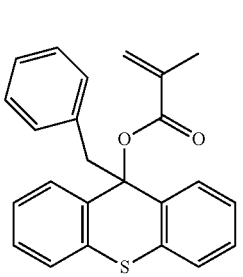
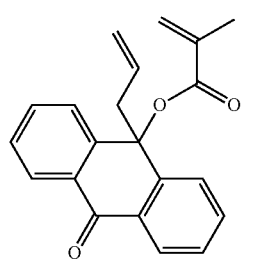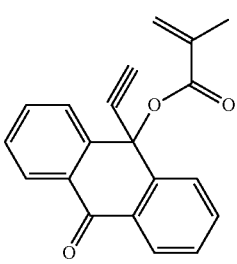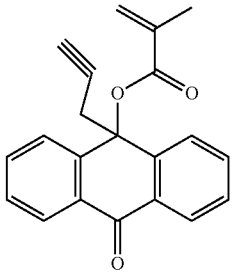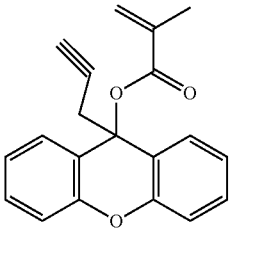
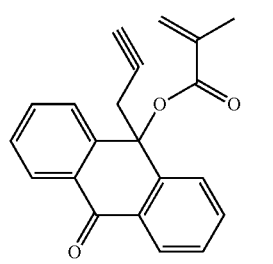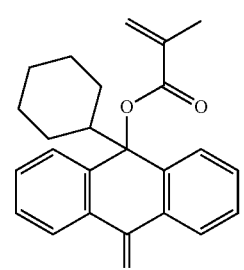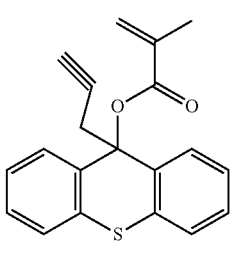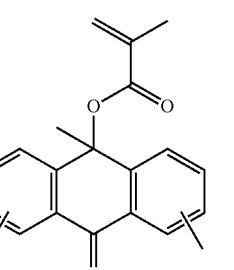
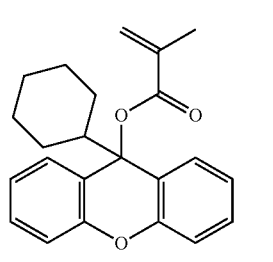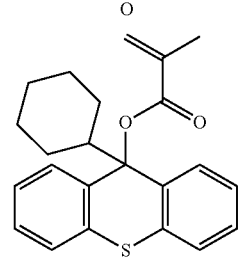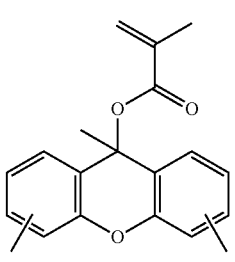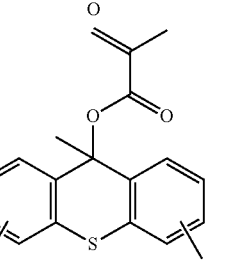

-continued
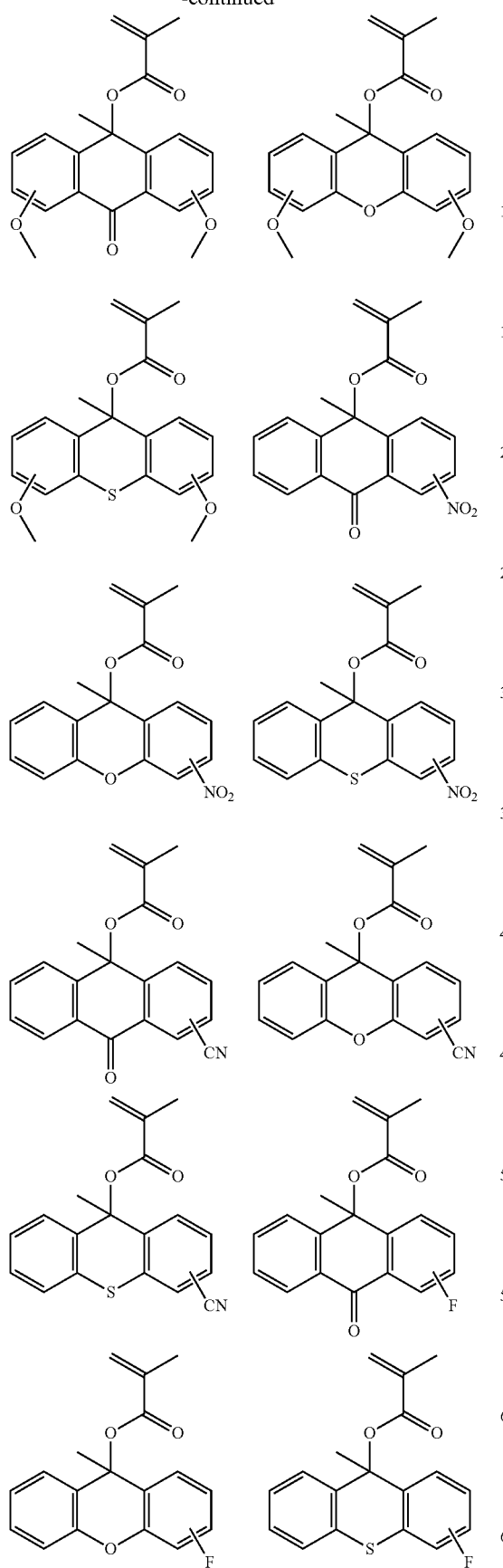
-continued
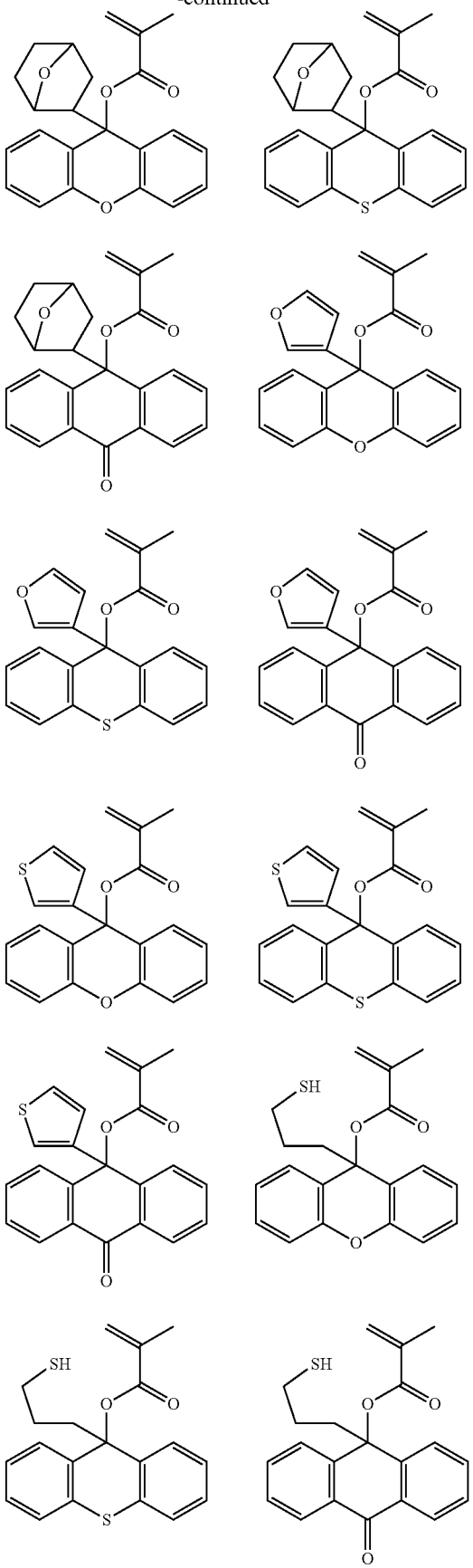

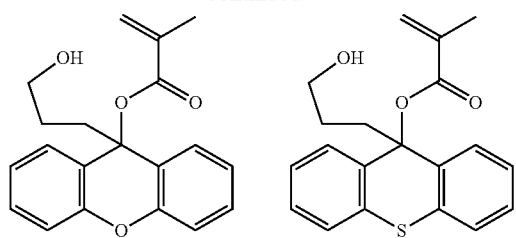
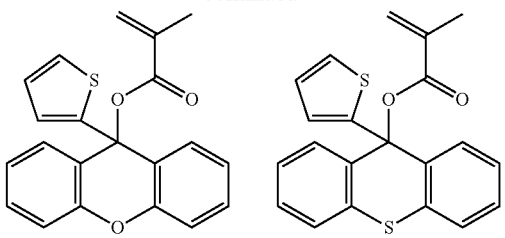
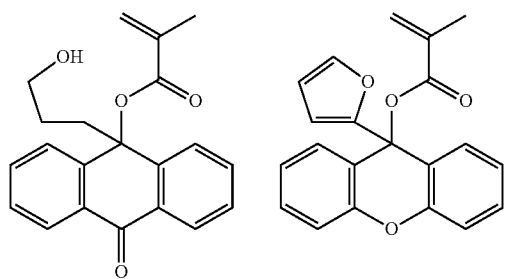
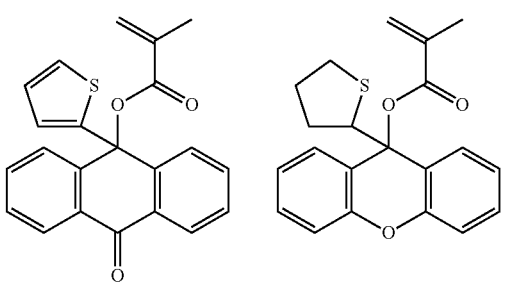
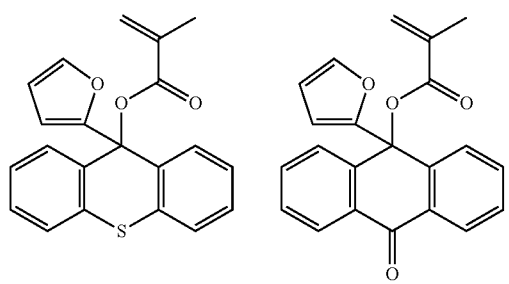
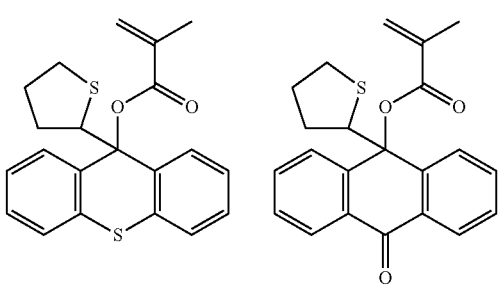
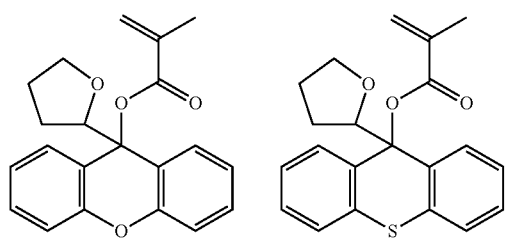
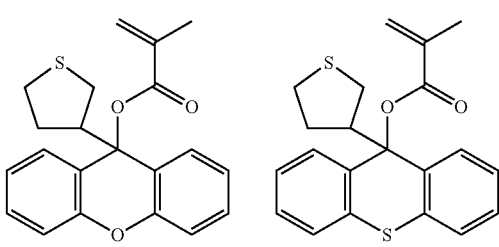
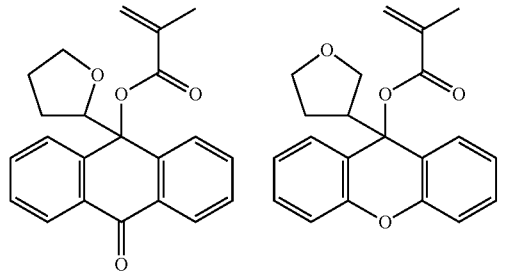
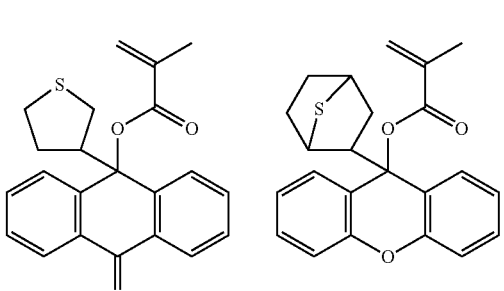
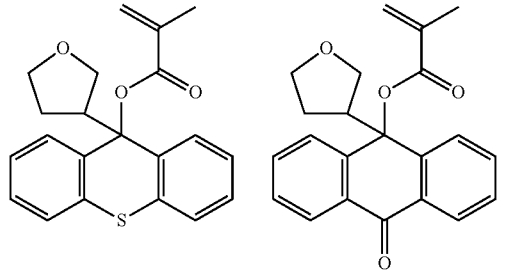
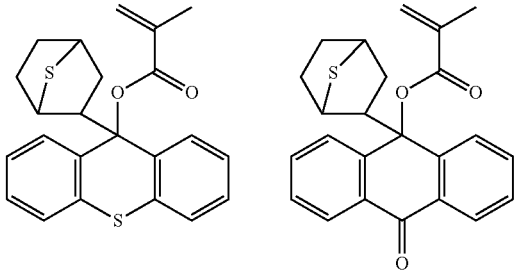

-continued
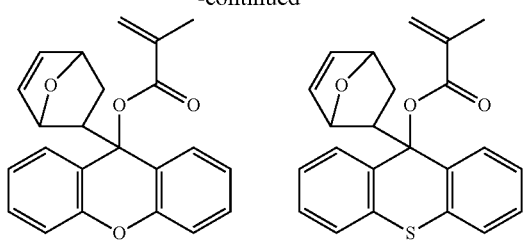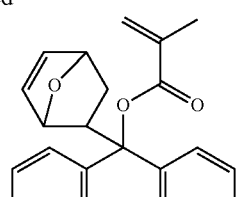
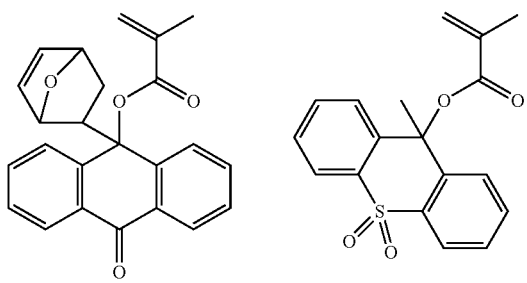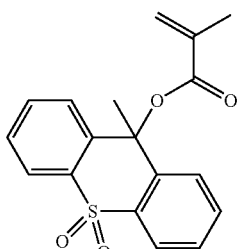
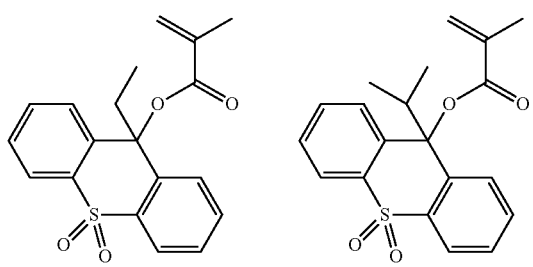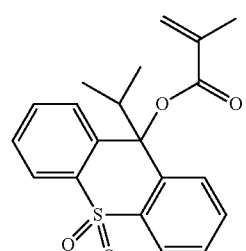
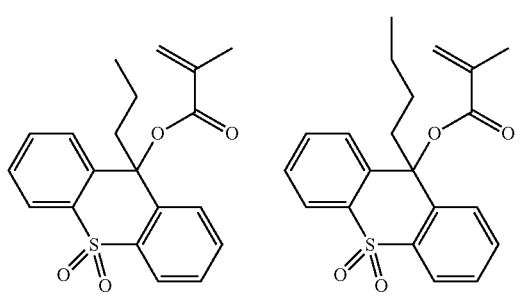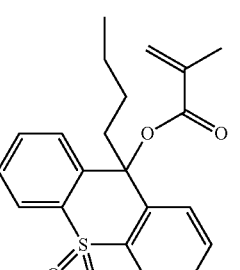
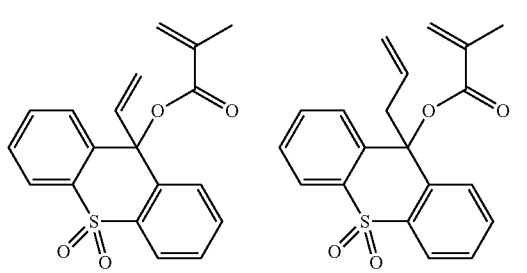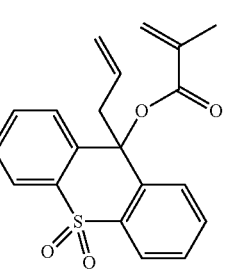
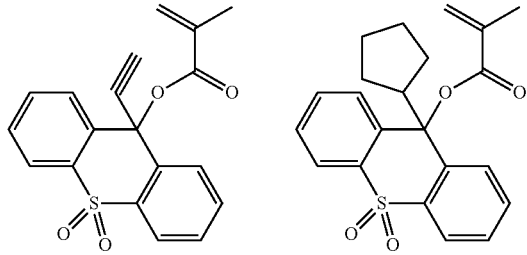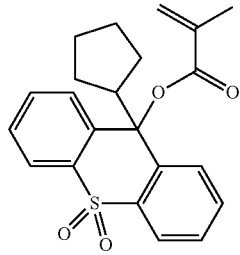
-continued
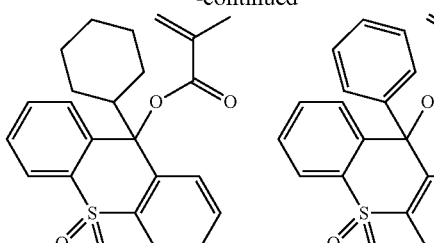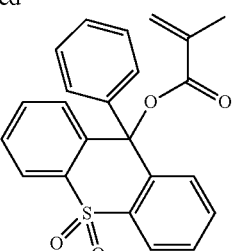
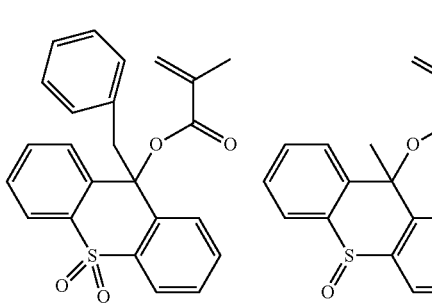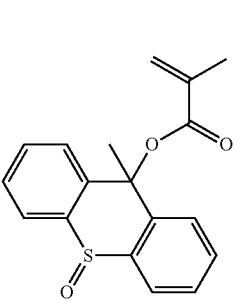
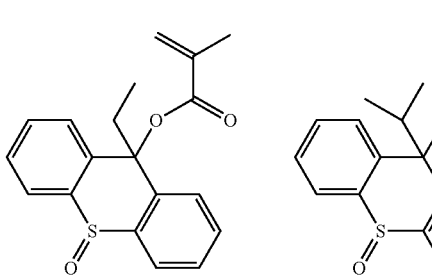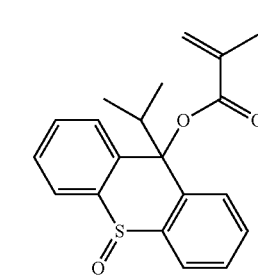
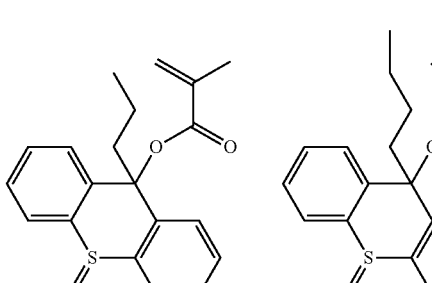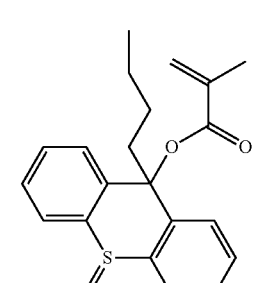
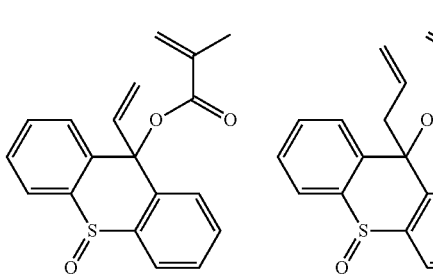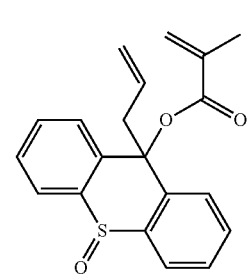
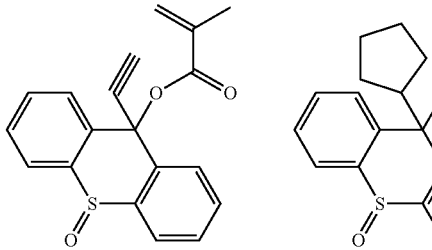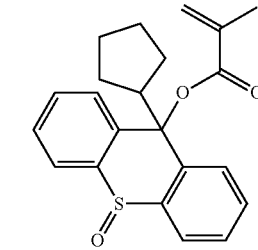

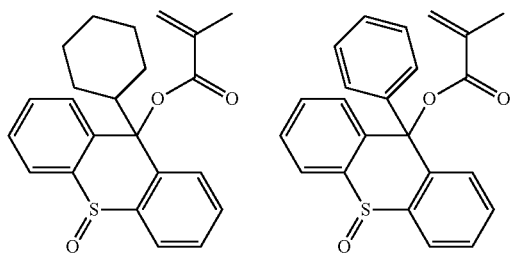

In addition, as the base resin of the photoresist composition used in the patterning process of the present invention, a polymer compound that further contains one or more copolymerized repeating units selected from repeating units b1 to b3 having a sulfonium salt structure represented by the general formula (3) is preferably used. When the base resin is such a polymer compound that has an acid generator bound in the polymer main chain, edge roughness (LWR, Line width roughness) of the pattern after development can be further reduced.

(3)

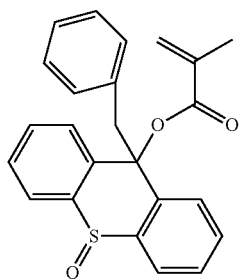

wherein $R^{020}$, $R^{024}$, and $R^{028}$ represent a hydrogen atom or a methyl group; $R^{021}$ represents a single bond, a phenylene group, —O—$R^{033}$—, or —C(=O)—Y—$R^{033}$—, where Y represents an ether group or a NH group, and $R^{033}$ represents a phenylene group or a linear, branched, or cyclic alkylene group or alkenylene group having 1 to 6 carbon atoms and optionally containing a carbonyl group, an ester group, an ether group, or a hydroxyl group; $R^{022}$, $R^{023}$, $R^{025}$, $R^{026}$, $R^{027}$, $R^{029}$, $R^{030}$, and $R^{031}$ may be the same or different and represent a linear, branched, or cyclic alkyl group having 1 to 12 carbon atoms and optionally containing a carbonyl group, an ester group, or an ether group, an aryl group having 6 to 12 carbon atoms, an aralkyl group having 7 to 20 carbon atoms, or a thiophenyl group; $A^1$ represents a single bond, -$A^0$-C(=O)—O—, -$A^0$-O—, or -$A^0$-O—C(=O)—, where $A^0$ represents a linear, branched, or cyclic alkylene group having 1 to 12 carbon atoms and optionally containing a carbonyl group, an ester group, or an ether group; $A^2$ represents a hydrogen atom, a $CF_3$ group, or =O; $Z^1$ represents a single bond, a methylene group, an ethylene group, a phenylene group, a fluorinated phenylene group, —O—$R^{032}$—, or —C(=O)—$Z^2$—$R^{032}$—, where $Z^2$ represents an ether group or a NH group, and $R^{032}$ represents a phenylene group, a fluorinated phenylene group, a phenylene group substituted with a trifluoromethyl group, or a linear, branched, or cyclic alkylene group or alkenylene group having 1 to 6 carbon atoms and optionally containing a carbonyl group, an ester group, an ether group, or a hydroxyl group; $M^-$ represents a non-nucleophilic counter ion; $0 \leq b1 \leq 0.3$; $0 \leq b2 \leq 0.3$; $0 \leq b3 \leq 0.3$; and $0 < b1+b2+b3 \leq 0.3$.

Illustrative examples of the monomer to give the repeating unit b1 having a sulfonium salt structure shown in the general formula (3) include the following compounds.

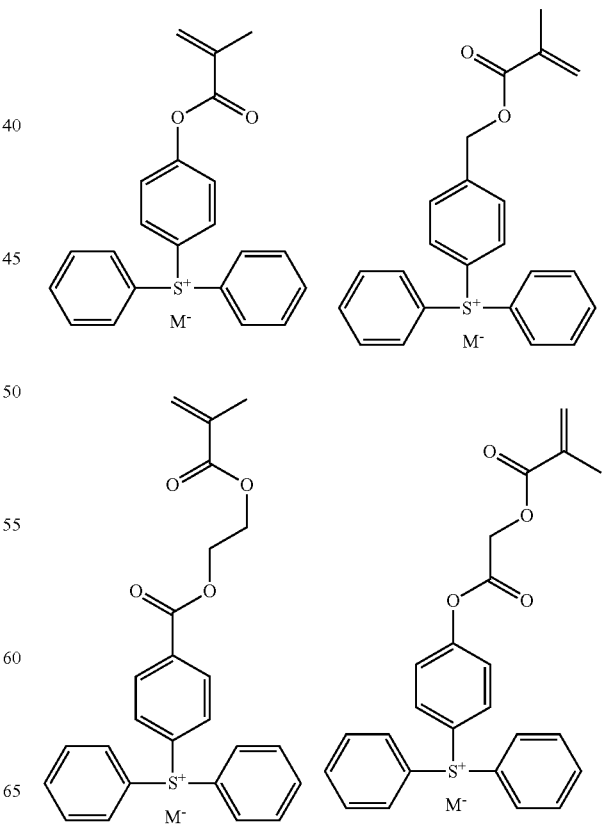

-continued
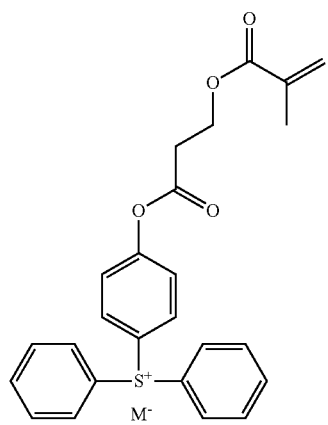
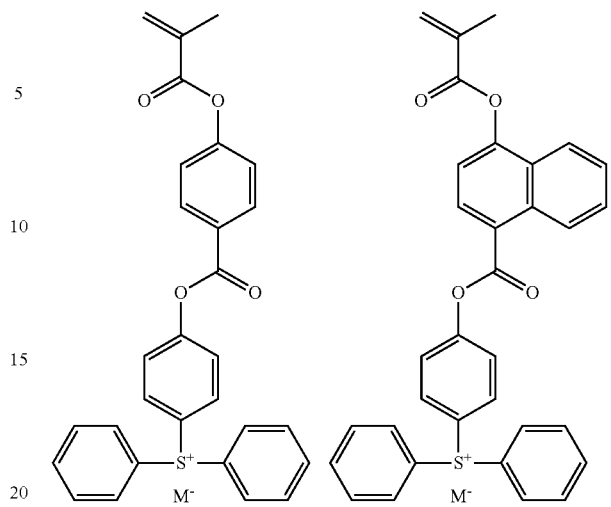
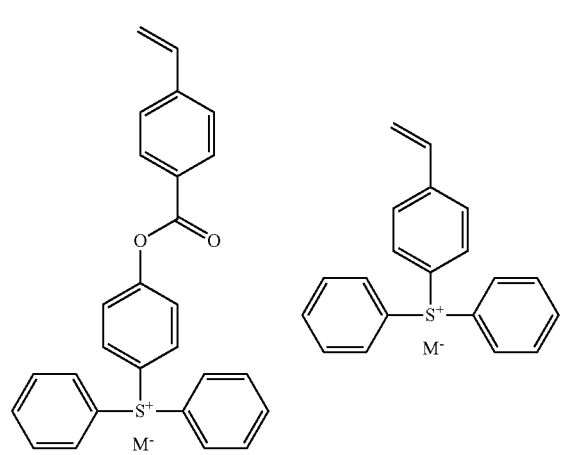
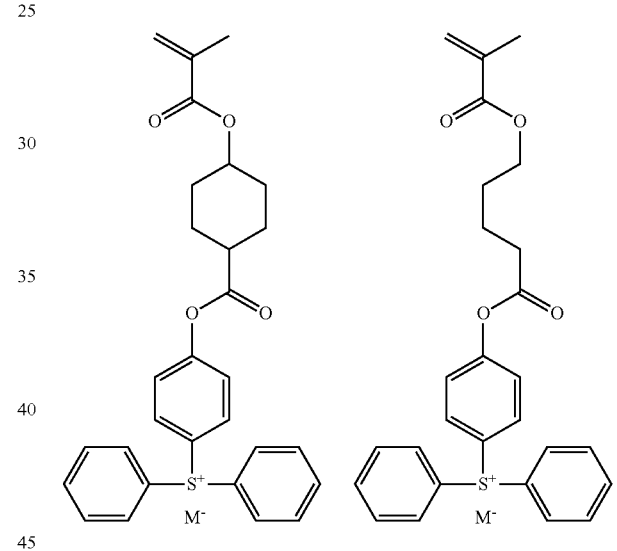
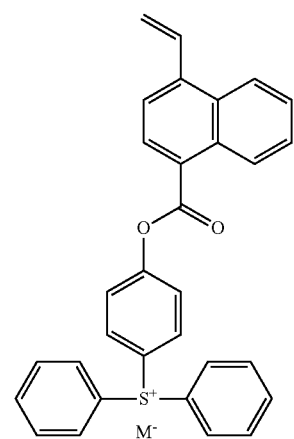
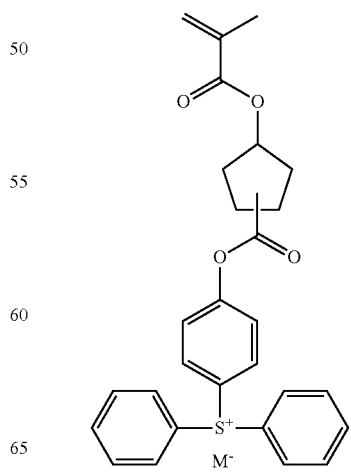

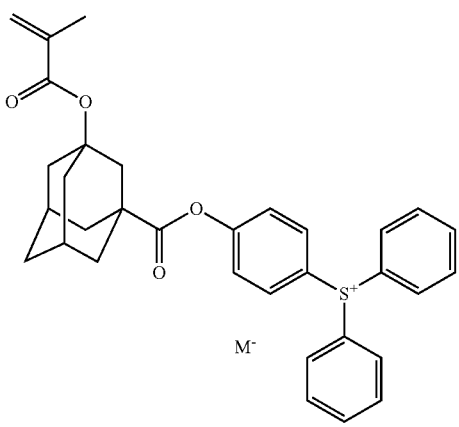

wherein M⁻ represents a non-nucleophilic counter ion.

Examples of the non-nucleophilic counter ion M⁻ include halide ions such as a chloride ion and a bromide ion; fluoroalkylsulfonates such as triflate, 1,1,1-trifluoroethanesulfonate, and nonafluorobutanesulfonate; arylsulfonates such as tosylate, benzenesulfonate, 4-fluorobenzenesulfonate, and 1,2,3,4,5-pentafluorobenzenesulfonate; alkylsulfonates such as mesylate and butanesulfonate; imides such as bis(trifluoromethylsulfonyl)imide, bis(perfluoroethylsulfonyl)imide, and bis(perfluorobutylsulfonyl)imide; and methide acids such as tris(trifluoromethylsulfonyl)methide and tris(perfluoroethylsulfonyl)methide.

In addition, as examples of M⁻, there may be mentioned a sulfonate whose α-position is fluoro-substituted, shown by the general formula (K-1) and a sulfonate whose α-position and β-position are fluoro-substituted, shown by the general formula (K-2).

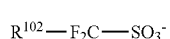
(K-1)

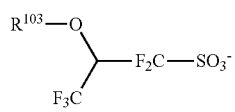
(K-2)

In the general formula (K-1), $R^{102}$ represents a hydrogen atom, or a linear, branched, or cyclic alkyl group having 1 to 20 carbon atoms, an alkenyl group having 2 to 20 carbon atoms, or an aryl group having 6 to 20 carbon atoms, and these groups may optionally contain an ether group, an ester group, a carbonyl group, a lactone ring, or a fluorine atom. In the general formula (K-2), $R^{103}$ represents a hydrogen atom, or a linear, branched, or cyclic alkyl group, an acyl group having 1 to 30 carbon atoms, an alkenyl group having 2 to 20 carbon atoms, an aryl group or an aryloxy group having 6 to 20 carbon atoms, and these groups may optionally contain an ether group, an ester group, a carbonyl group, or a lactone ring.

Illustrative examples of the monomer to give the repeating unit b2 having a sulfonium salt structure shown in the general formula (3) include the following compounds.

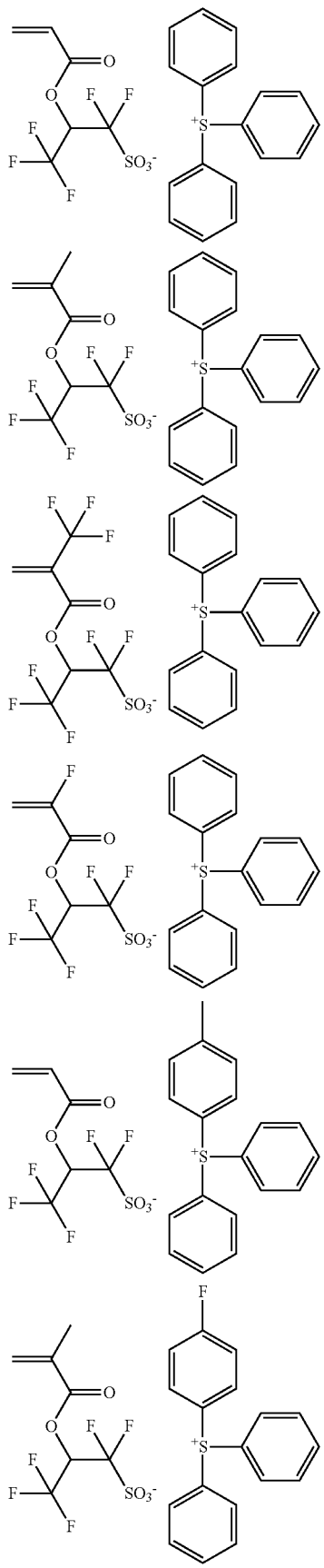

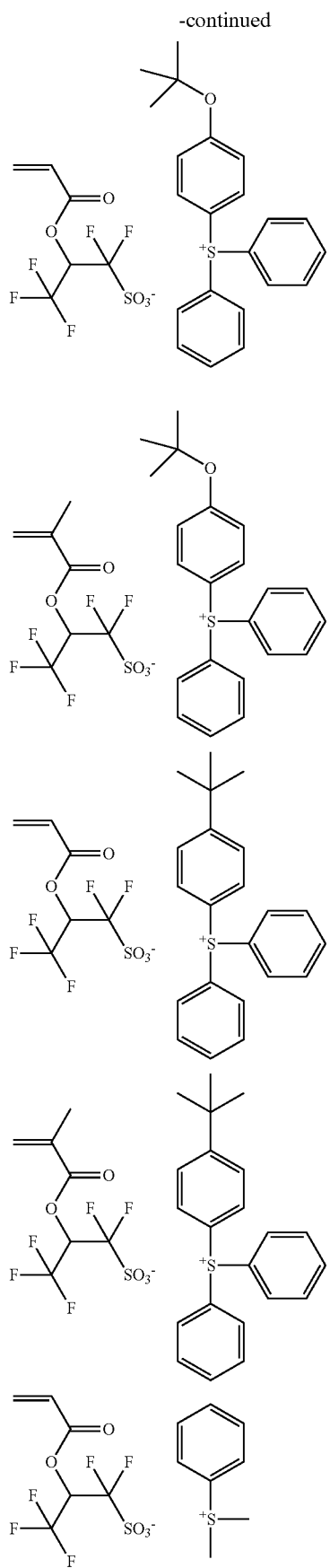
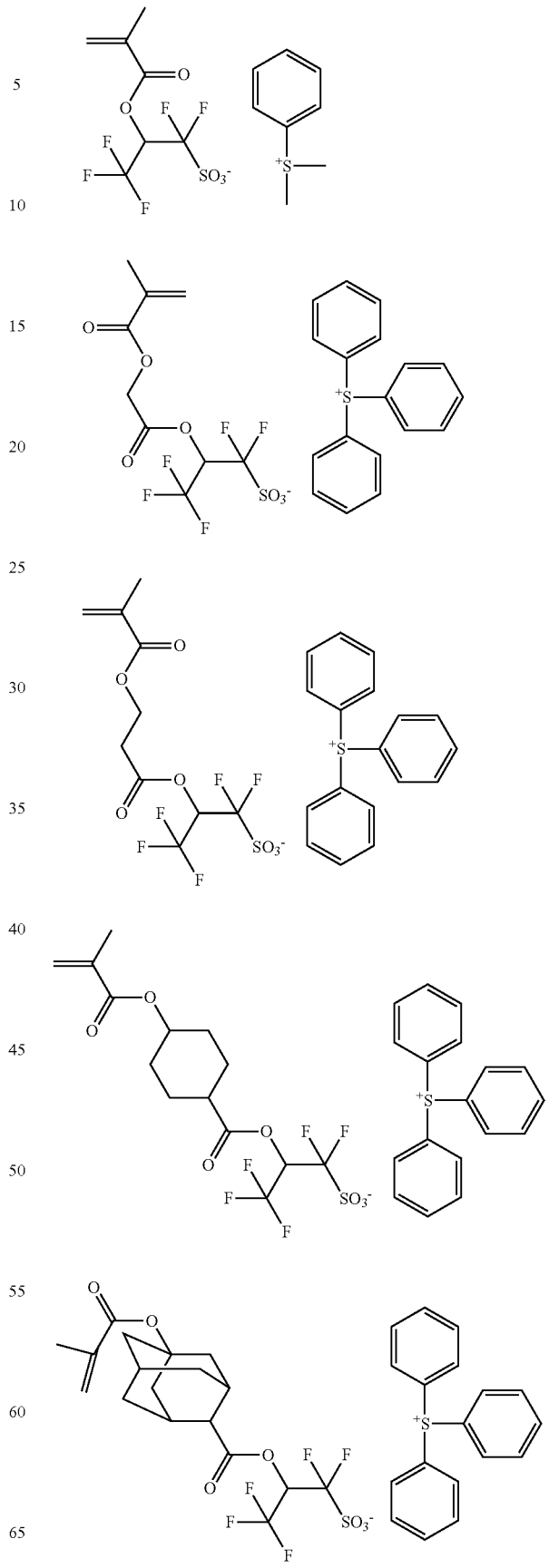

95
-continued
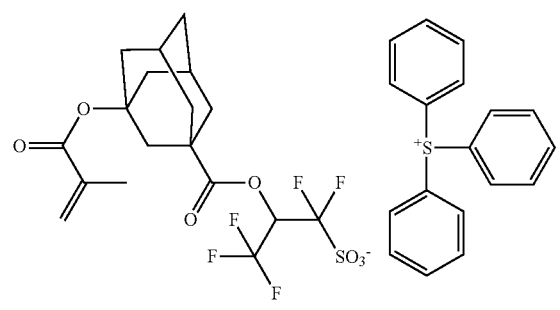
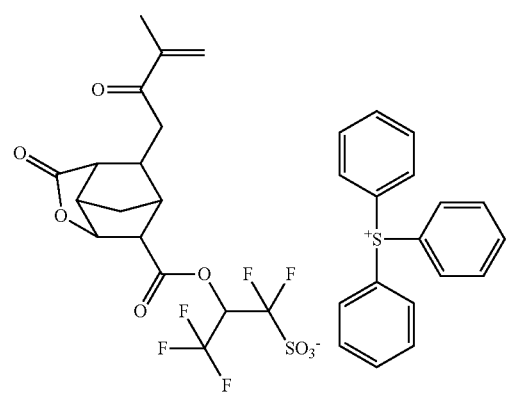
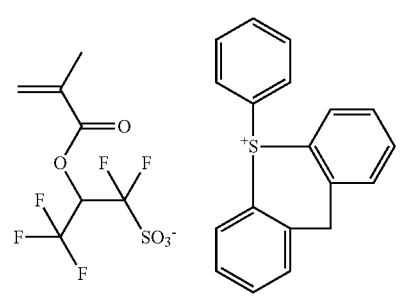
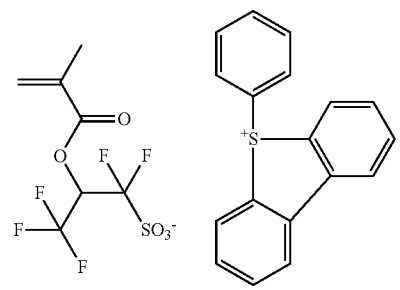
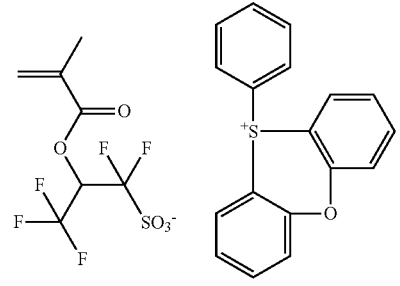
96
-continued
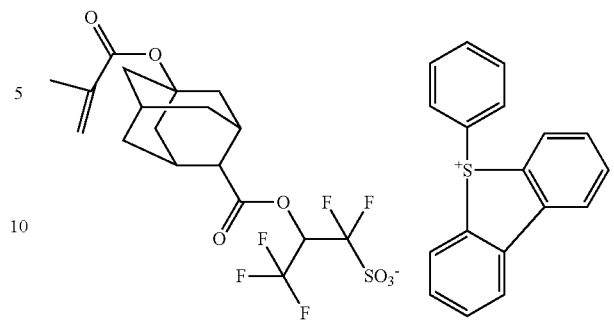
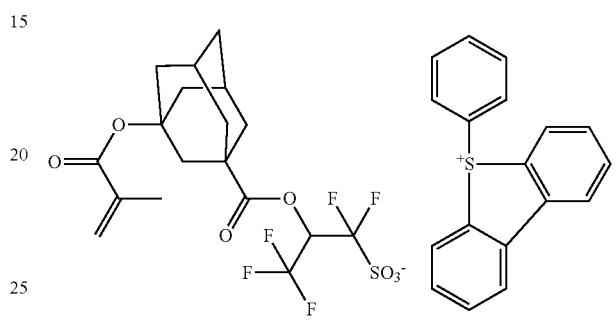
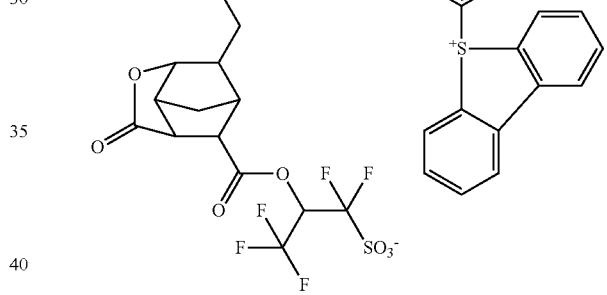
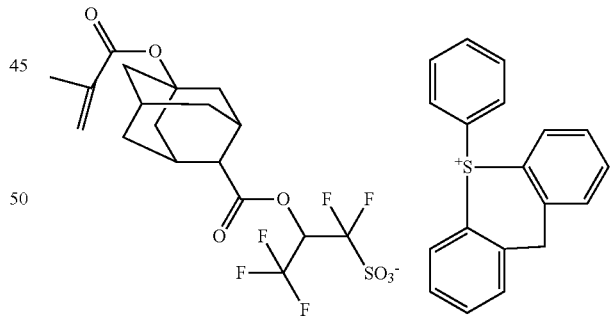
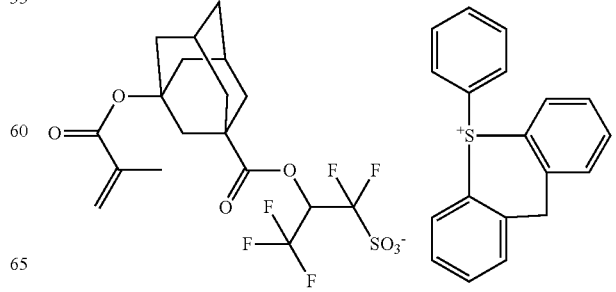

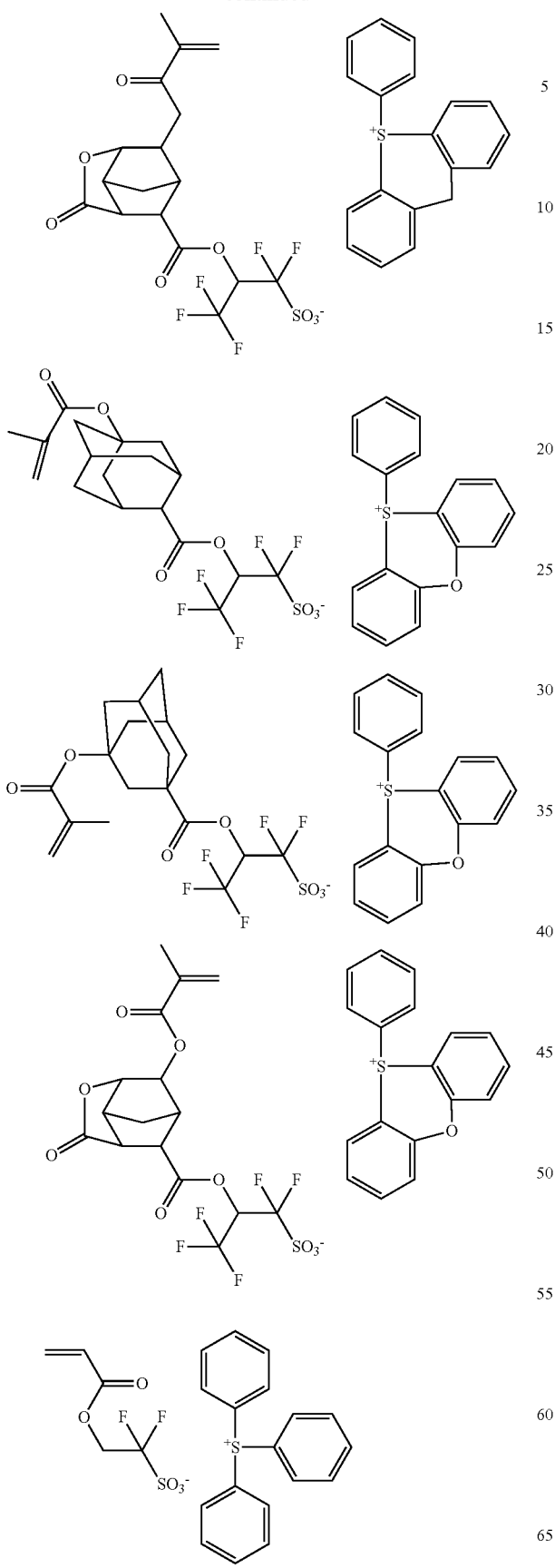
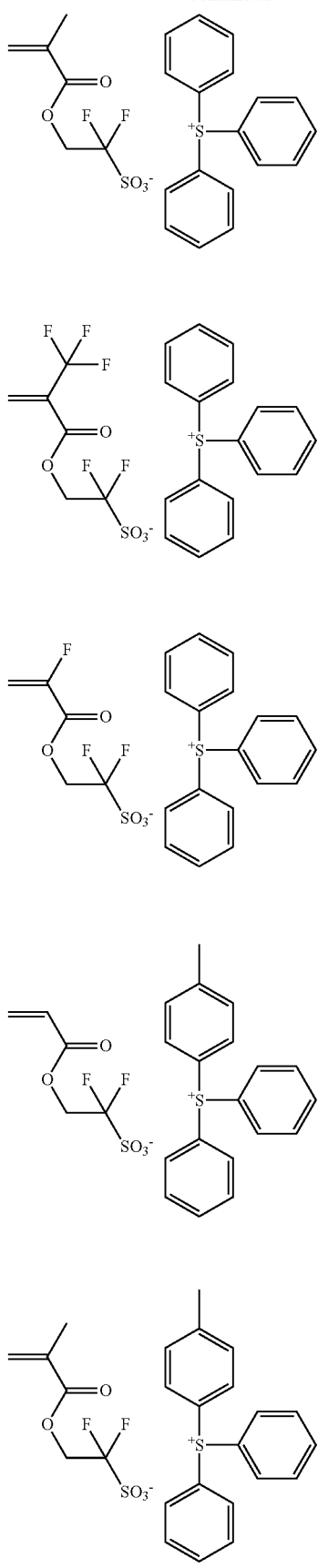

99
-continued
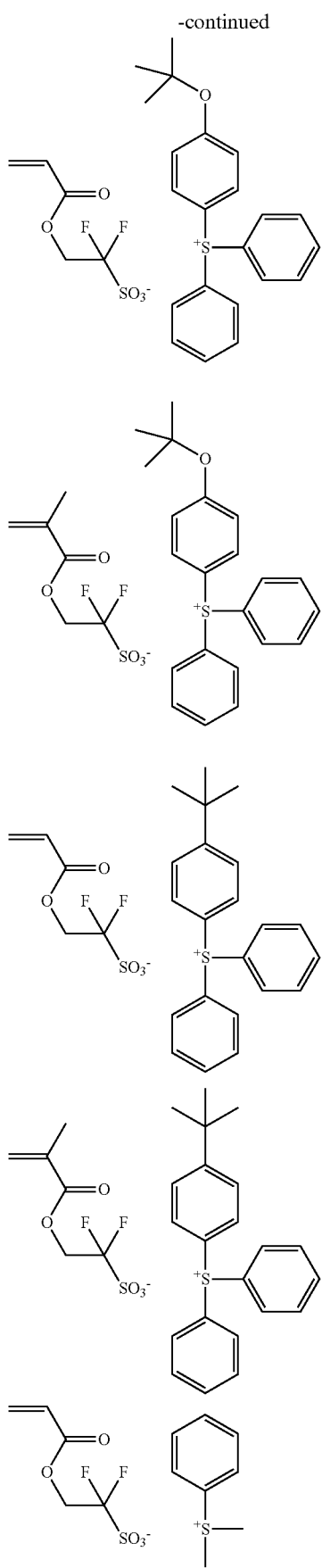
100
-continued
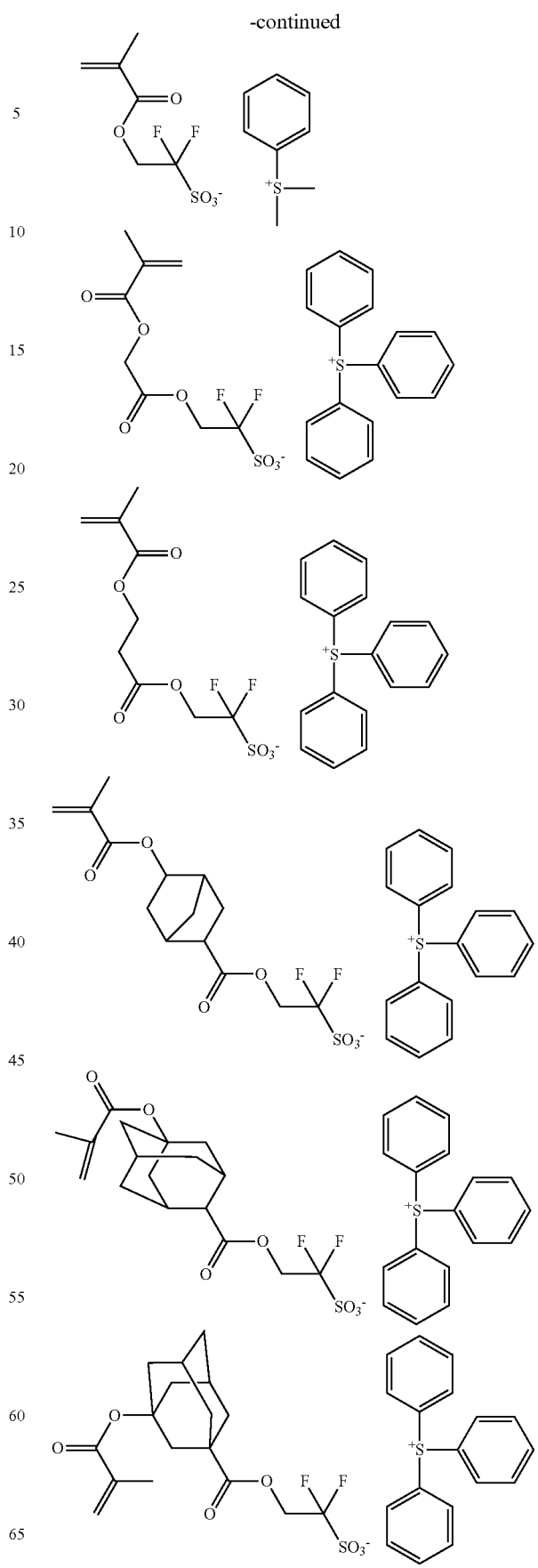

-continued
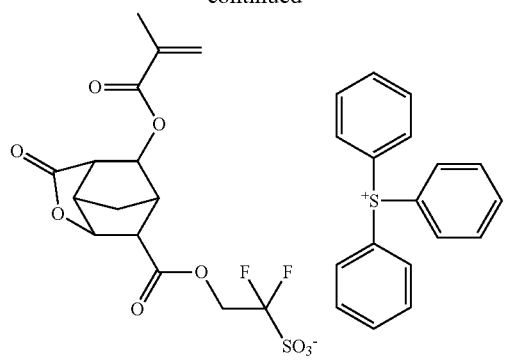
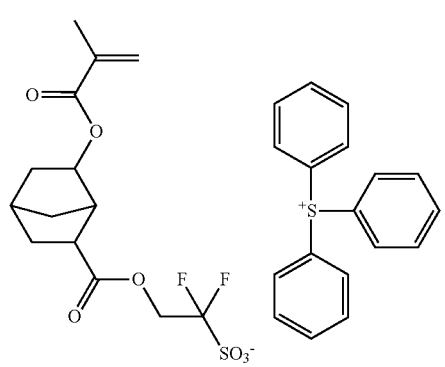
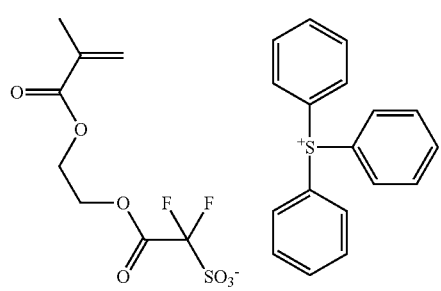
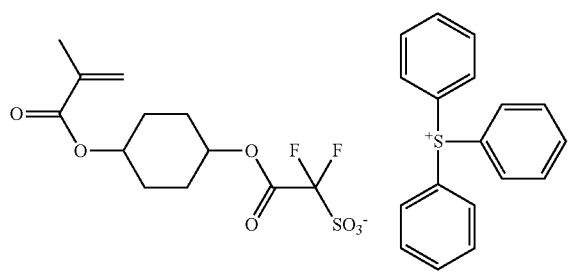
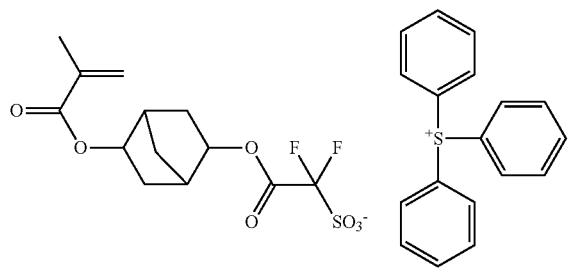
-continued
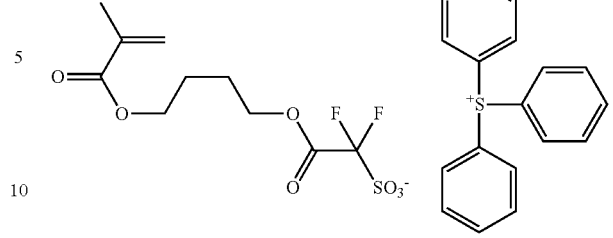
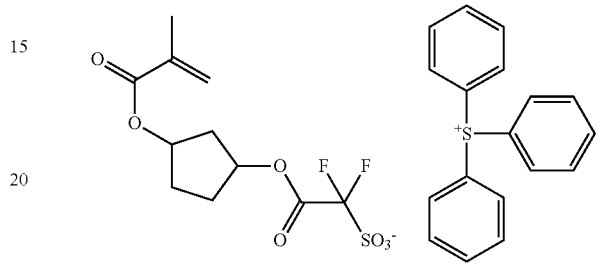
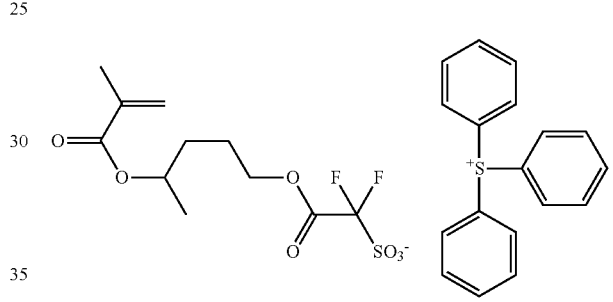
Illustrative examples of the monomer to give the repeating unit b3 having a sulfonium salt structure shown in the general formula (3) include the following compounds.
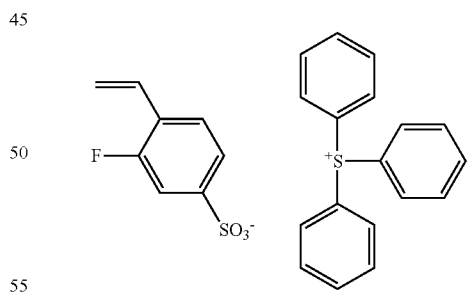
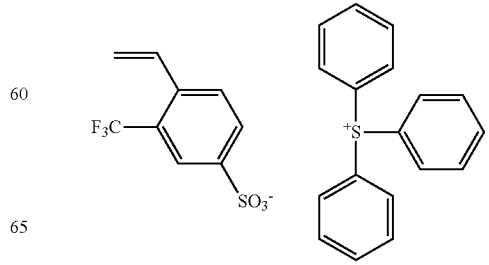

103
-continued
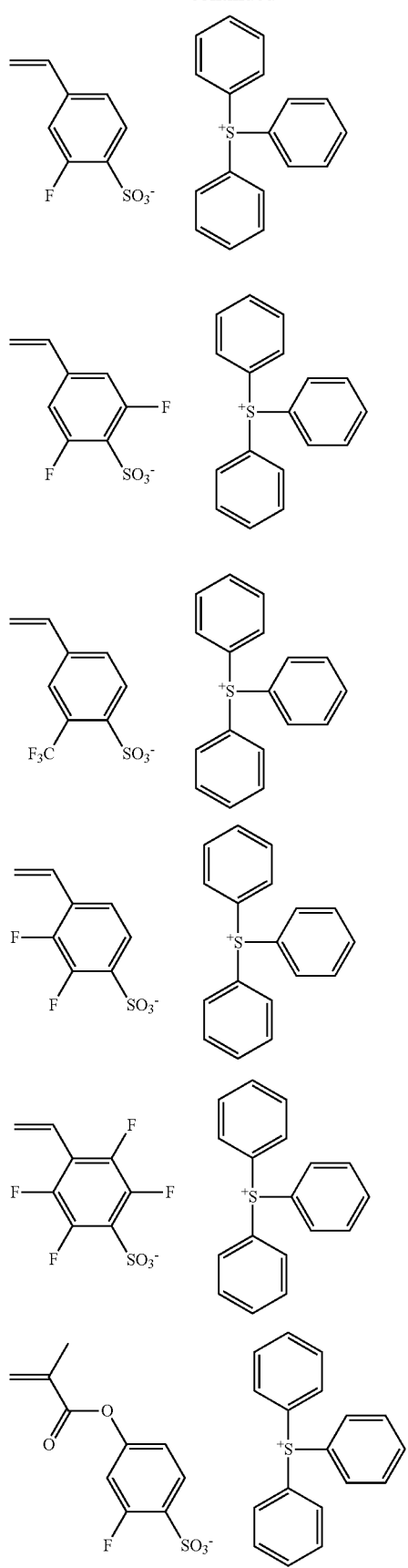
104
-continued
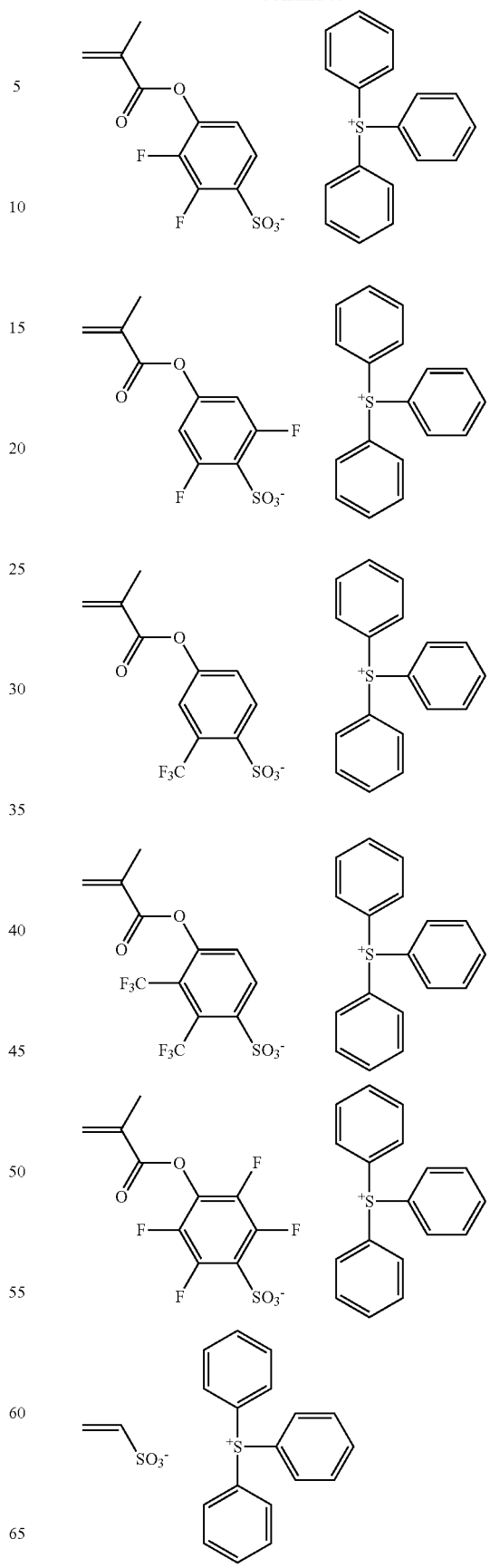

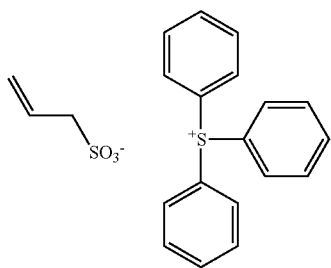 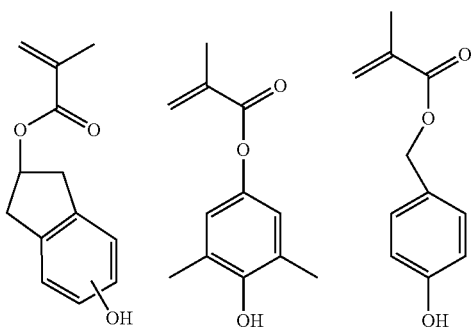

Further, as mentioned above, the base resin of the resist composition used in the present invention may contain a repeating unit having an adhesive group. As the repeating unit having an adhesive group, there may be mentioned repeating unit c having a phenolic hydroxyl group.

Illustrative examples of the monomer to give the repeating unit c having a phenolic hydroxyl group include the following compounds.

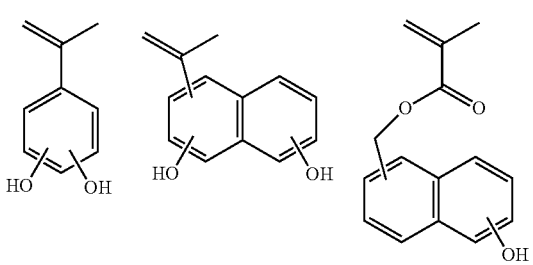
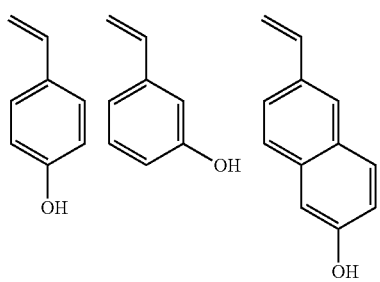
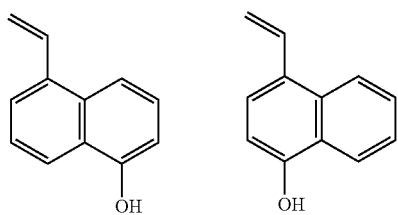
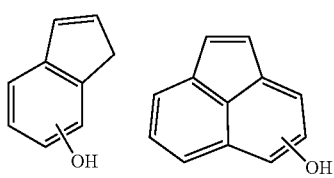
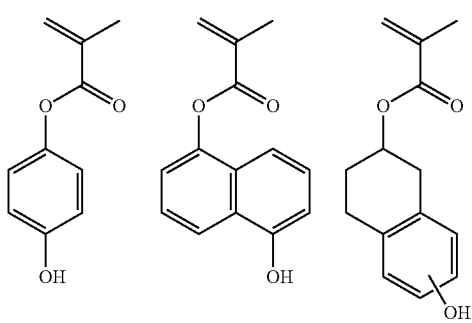

107
-continued
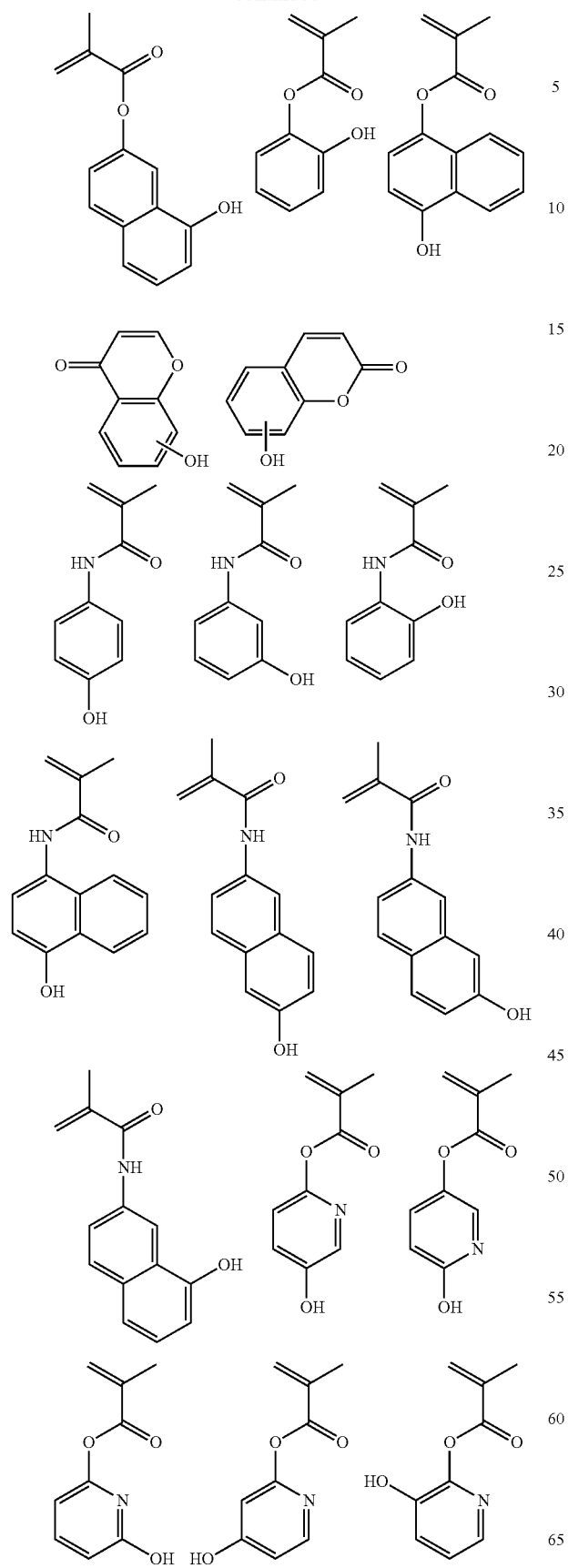
108
-continued
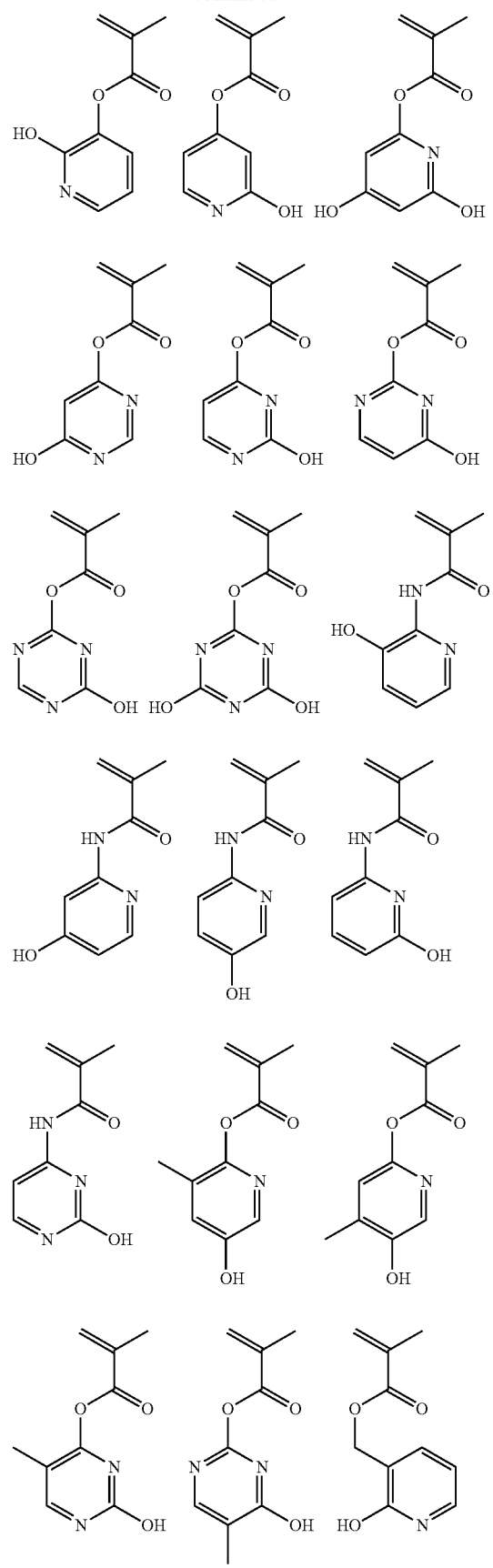

109
-continued
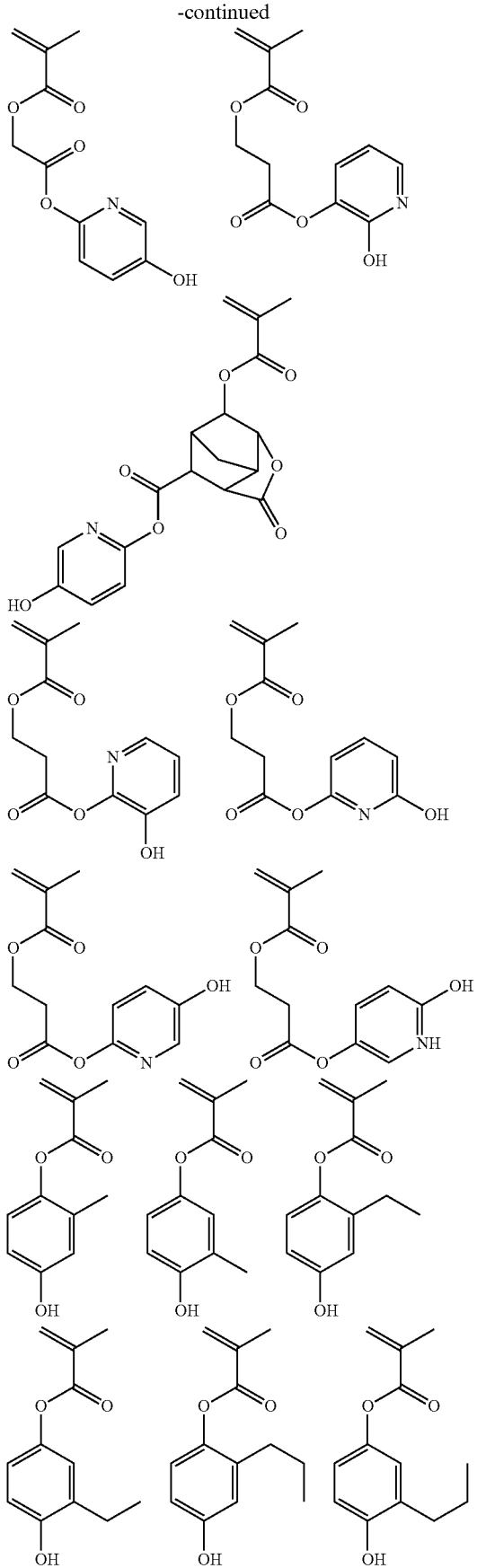
110
-continued
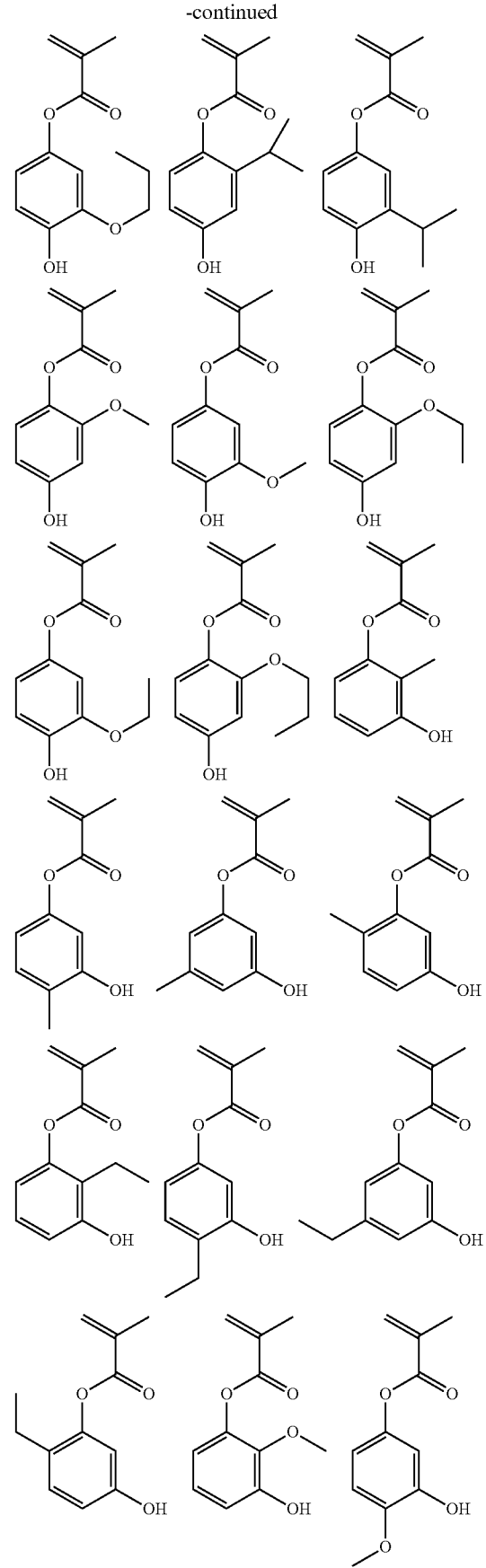

111
-continued
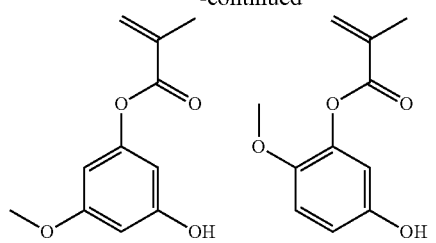
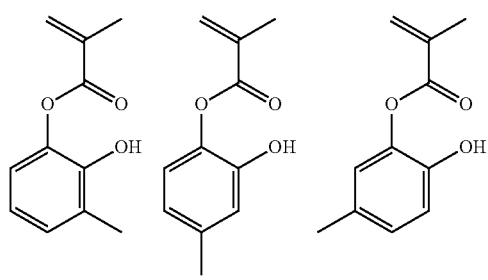
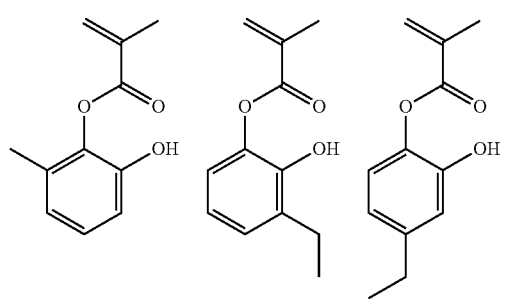
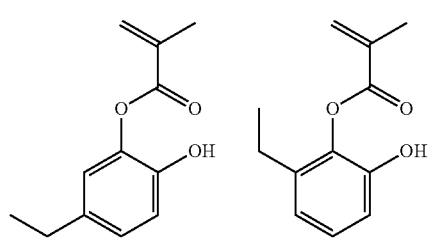
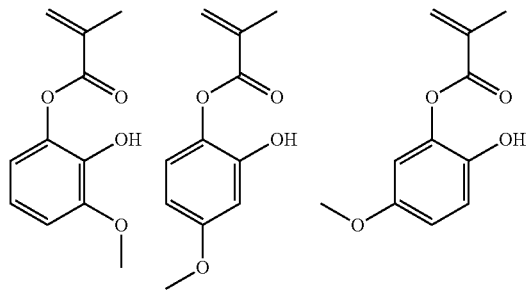
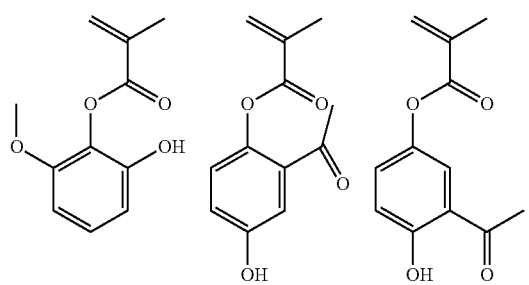
112
-continued
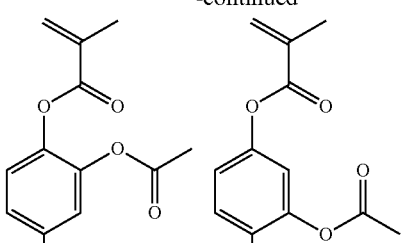
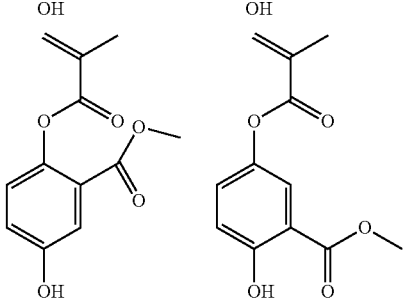
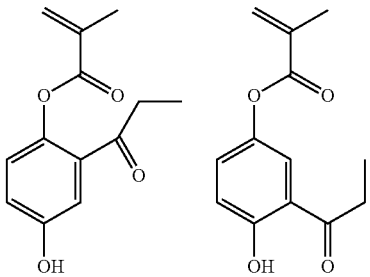
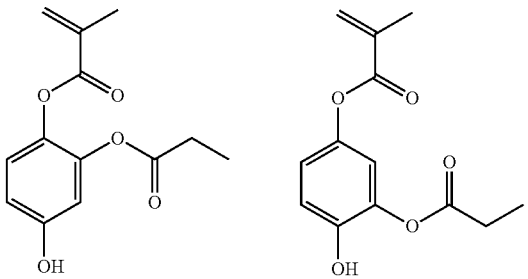
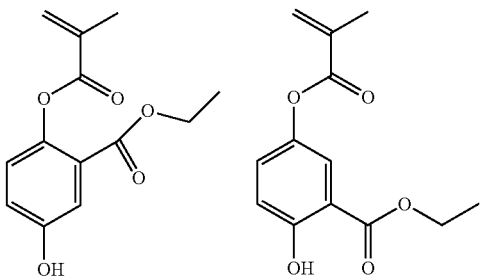
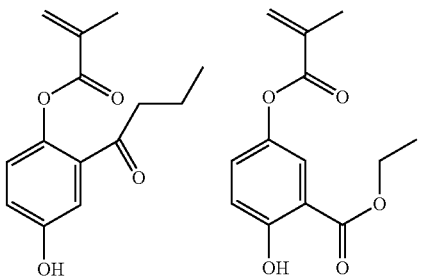

113
-continued
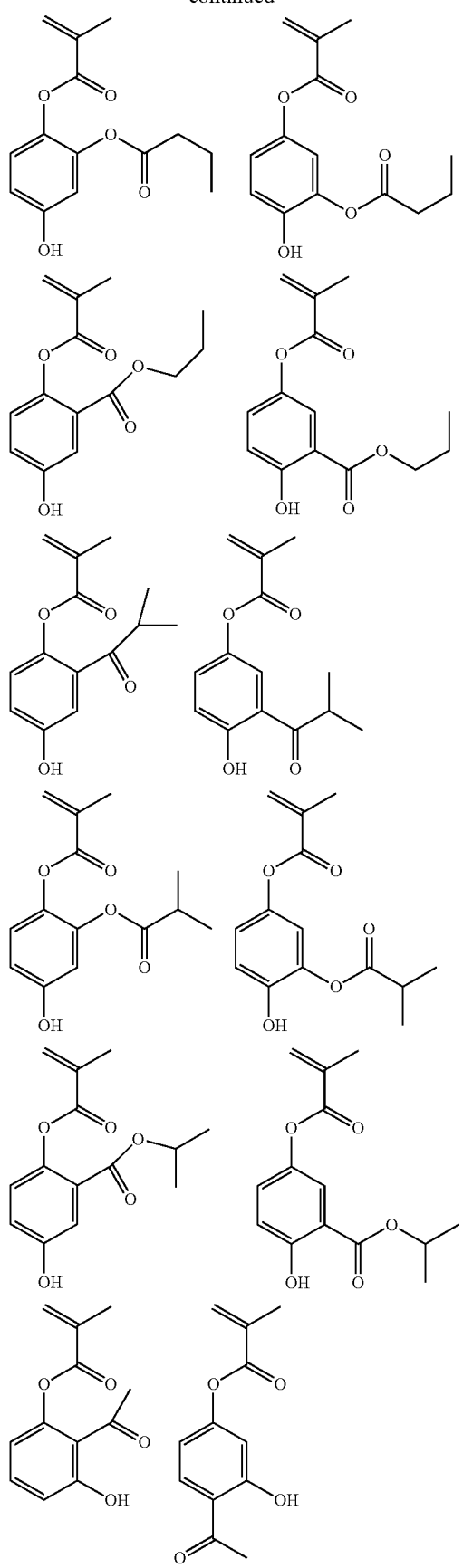
114
-continued
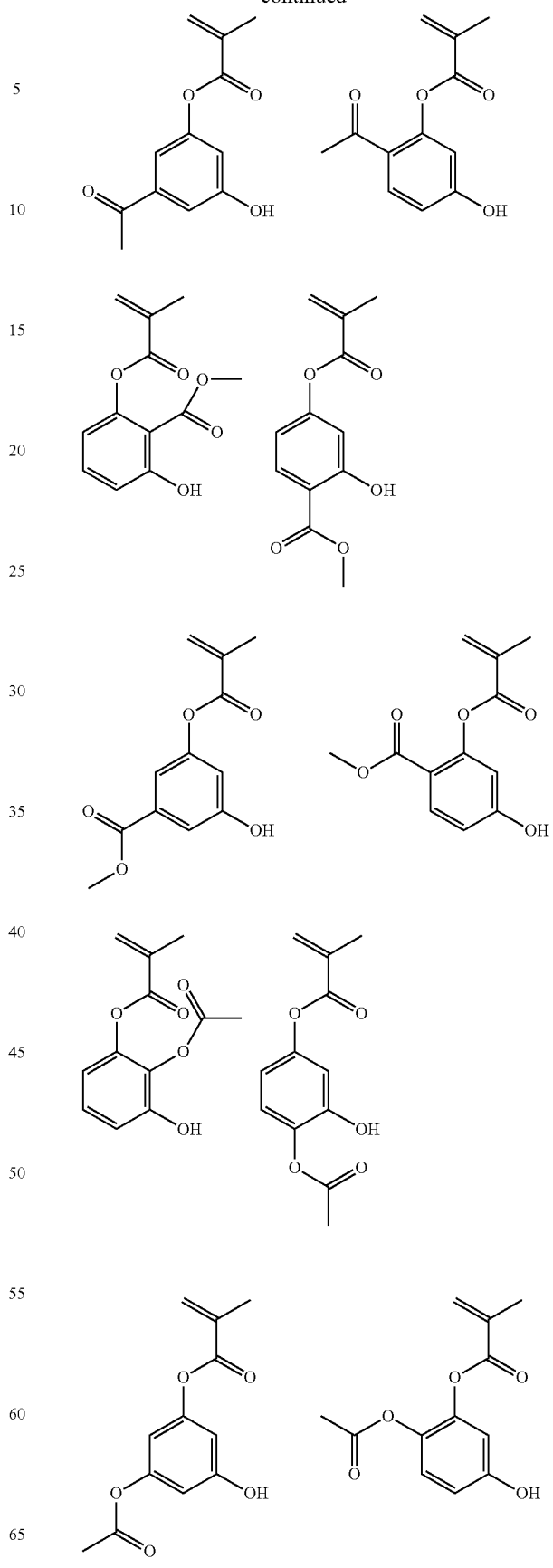

115
-continued
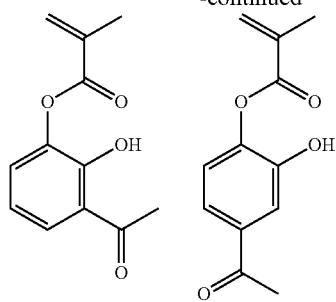
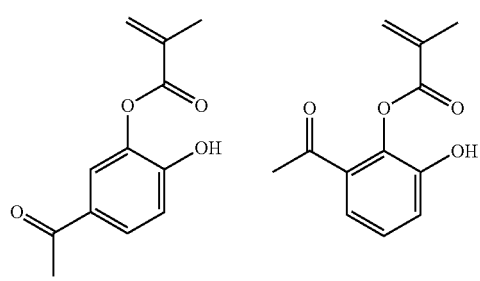
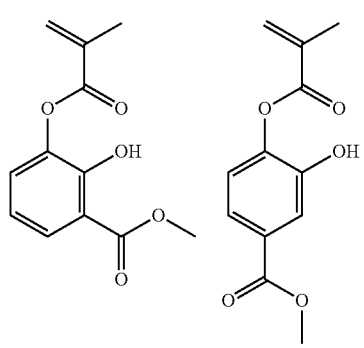
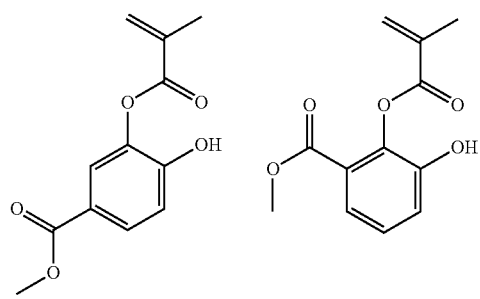
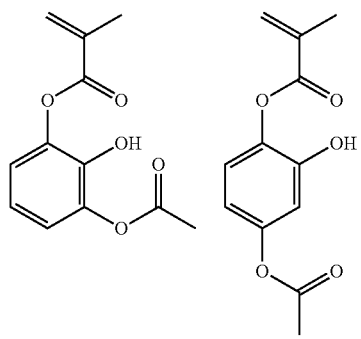
116
-continued
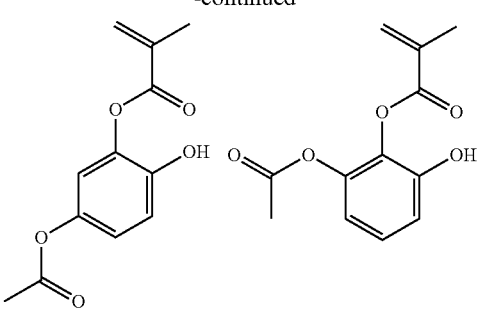
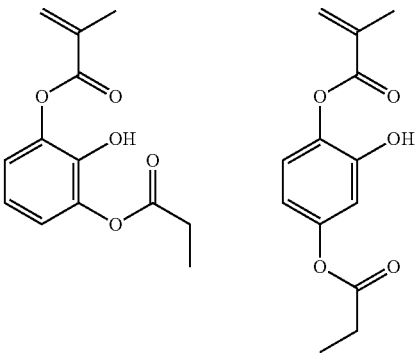
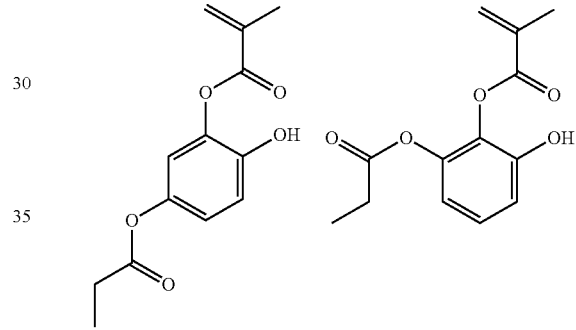
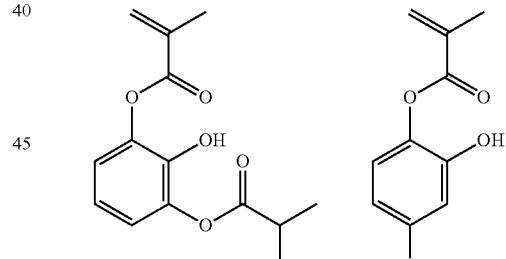
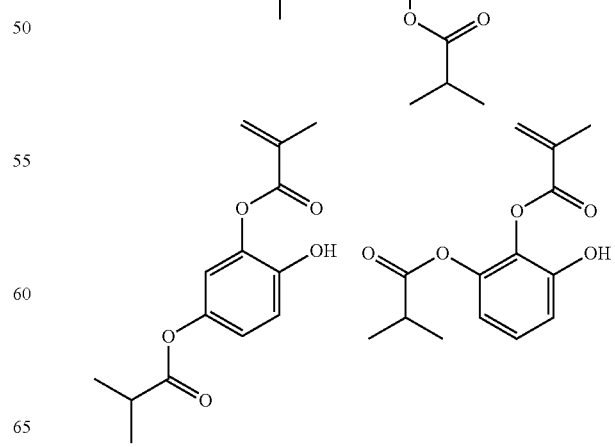

117
-continued
118
-continued
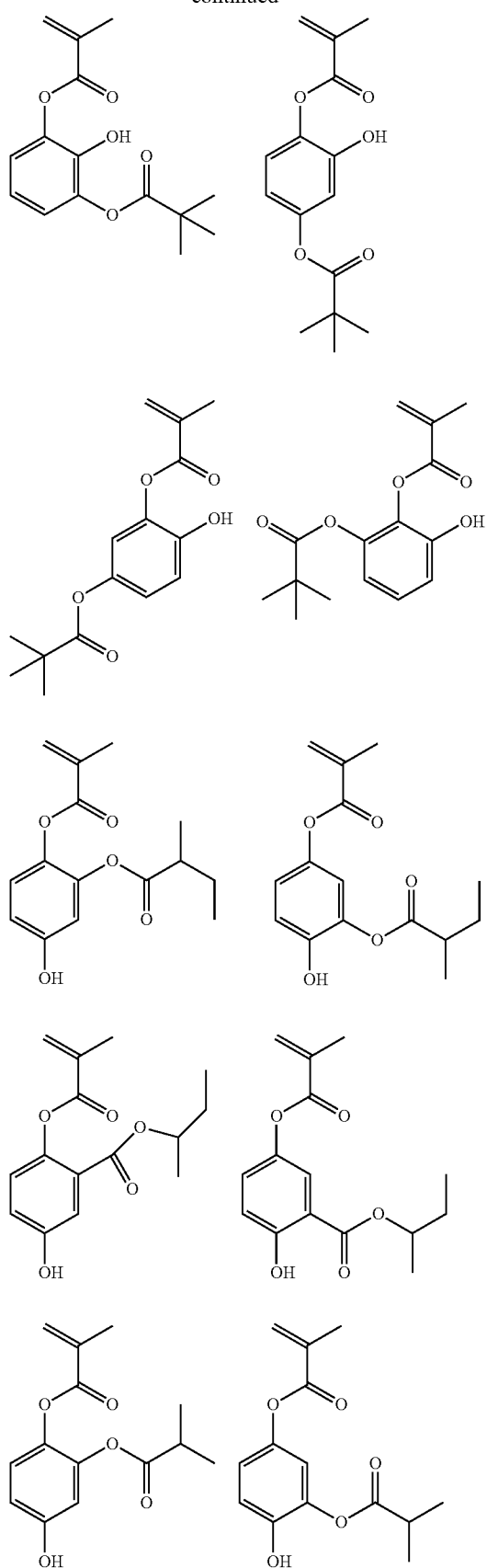
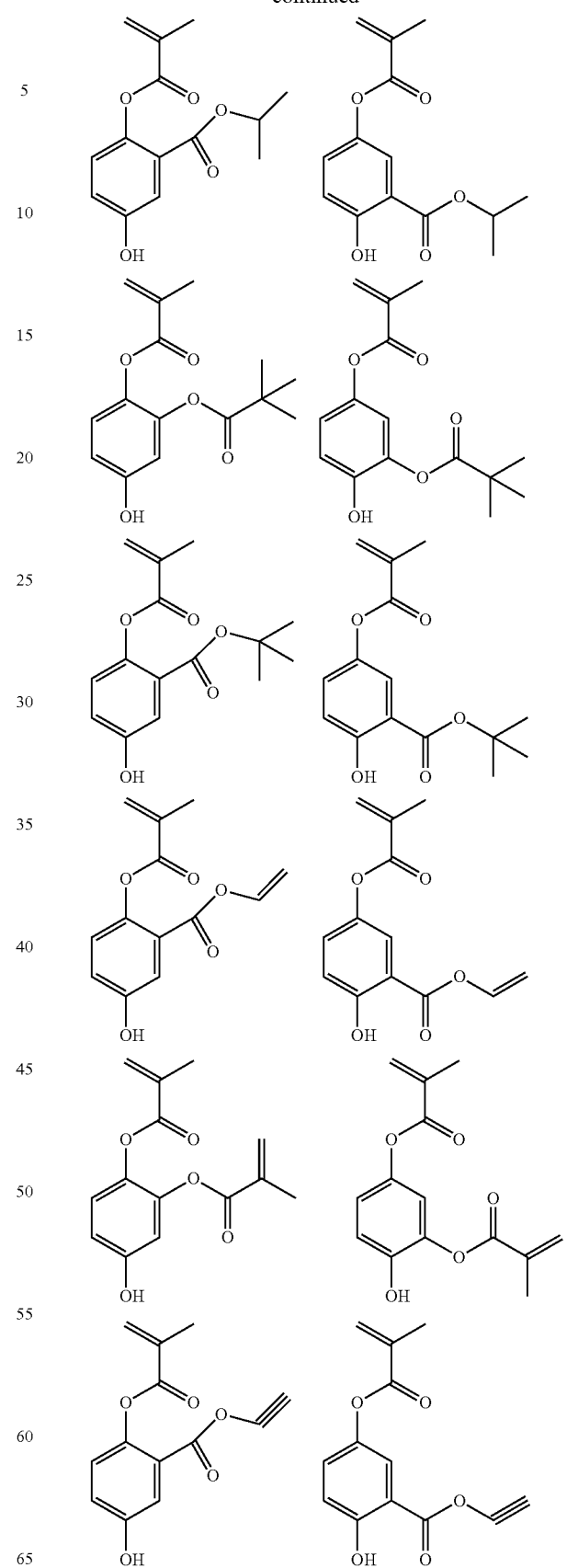

-continued

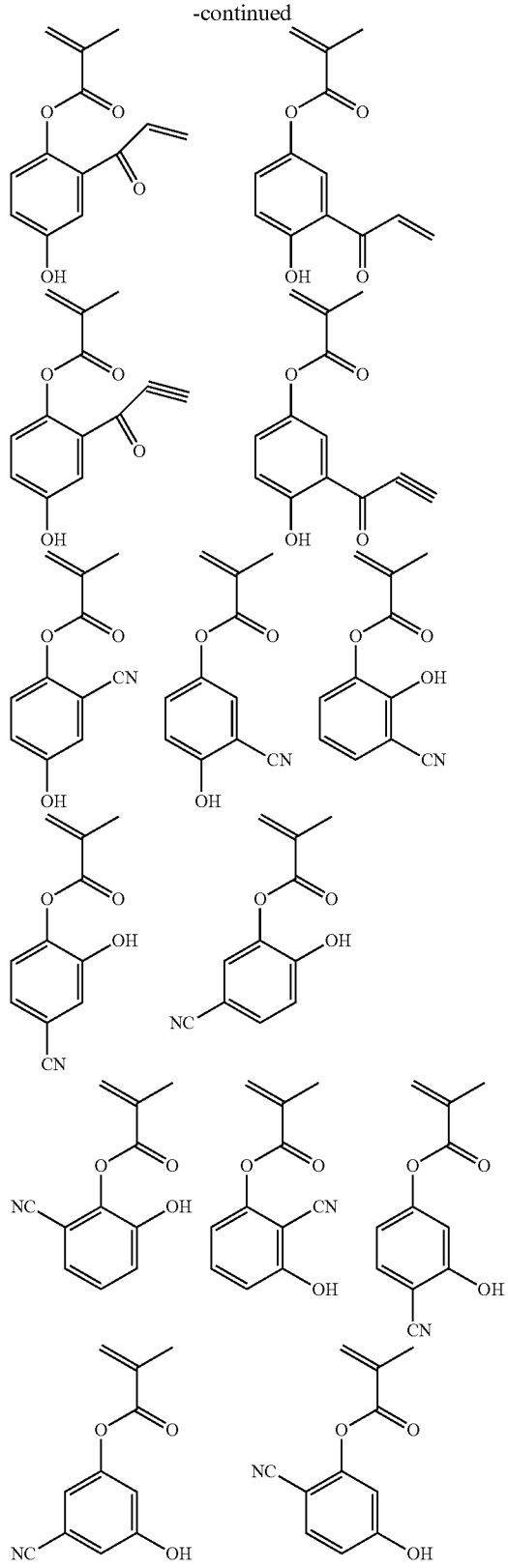

In addition, repeating unit d having another adhesive group selected from a carboxyl group, a lactone ring, a carbonate group, a thiocarbonate group, a carbonyl group, a cyclic acetal group, an ether group, an ester group, a sulfonate group, a cyano group, an amide group, and —O—C(=O)-G- (where G represents a sulfur atom or NH) may be copolymerized. Above all, a repeating unit having a lactone ring as an adhesive group is preferred.

Illustrative examples of the monomer to give the repeating unit d include the following compounds.

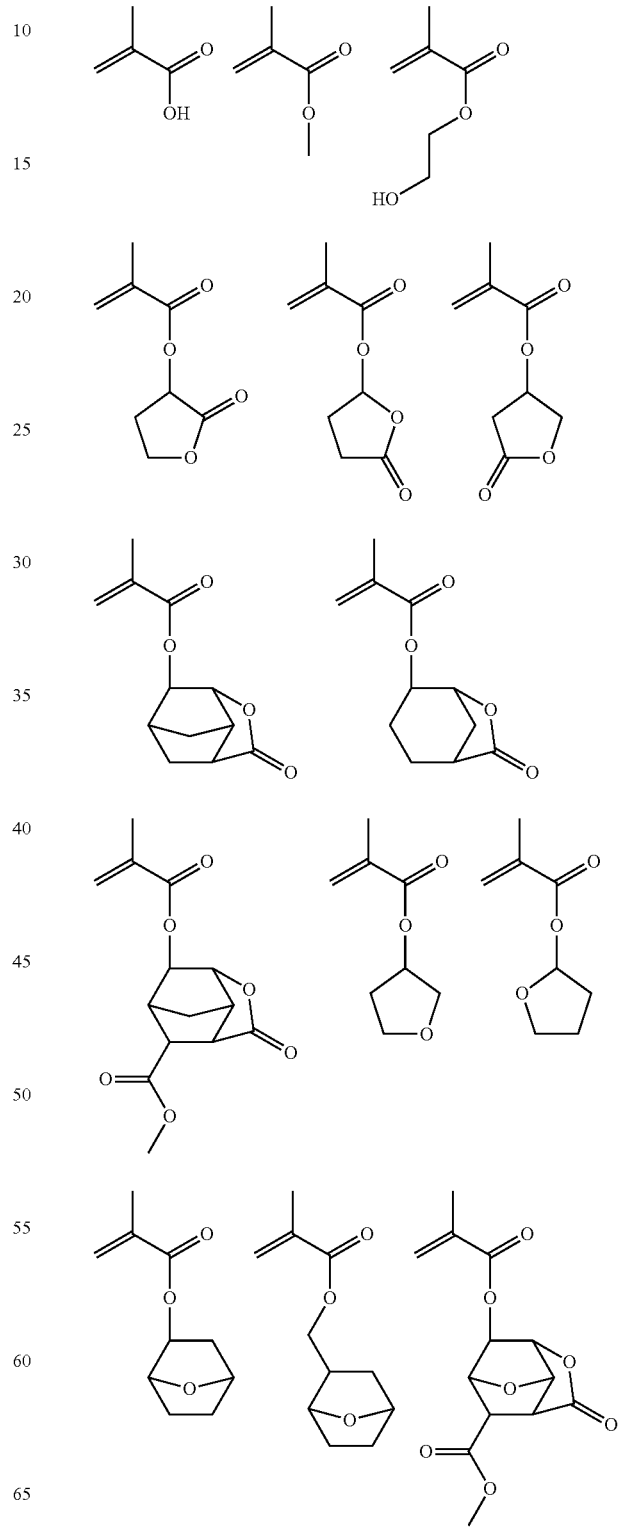

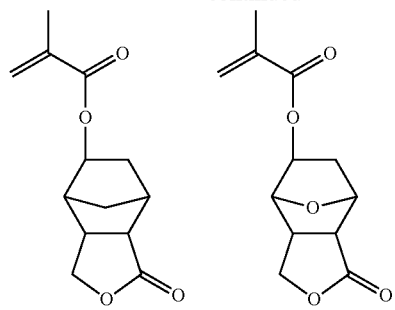
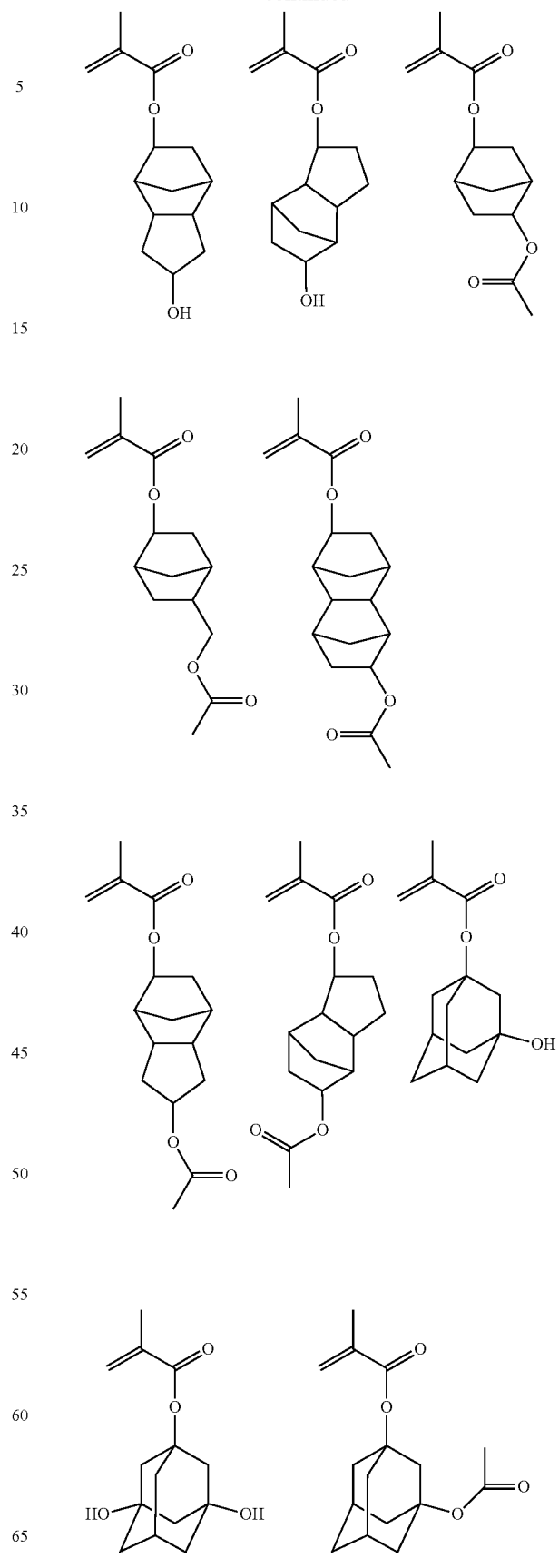

123
-continued
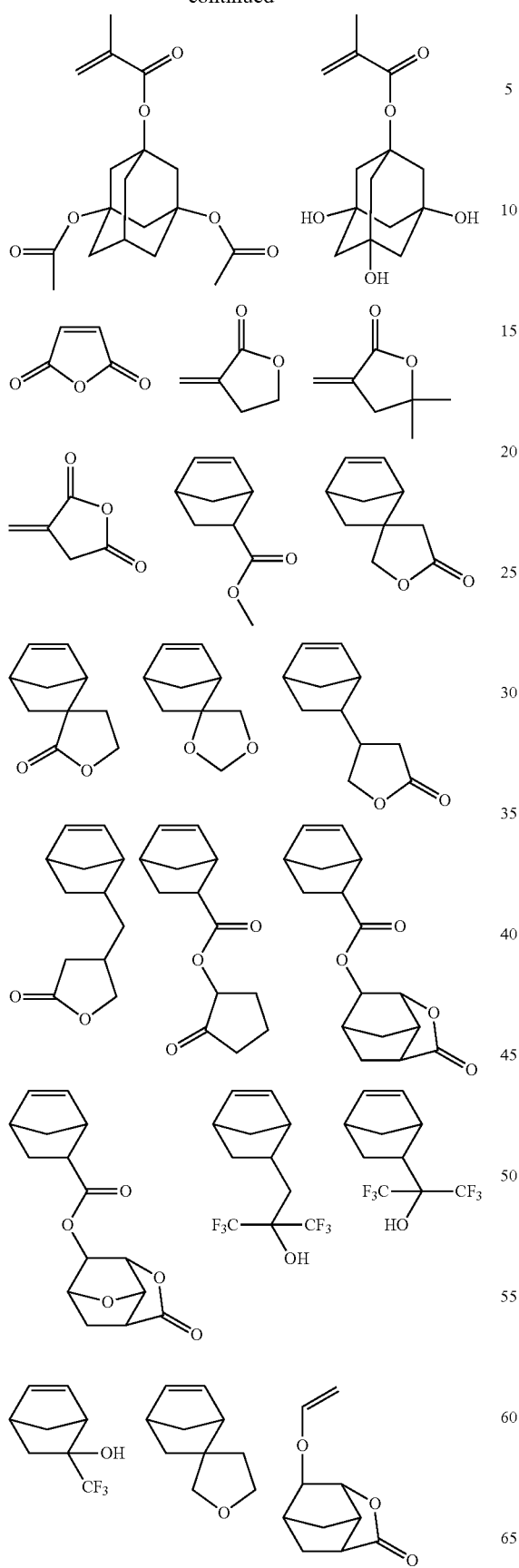
124
-continued
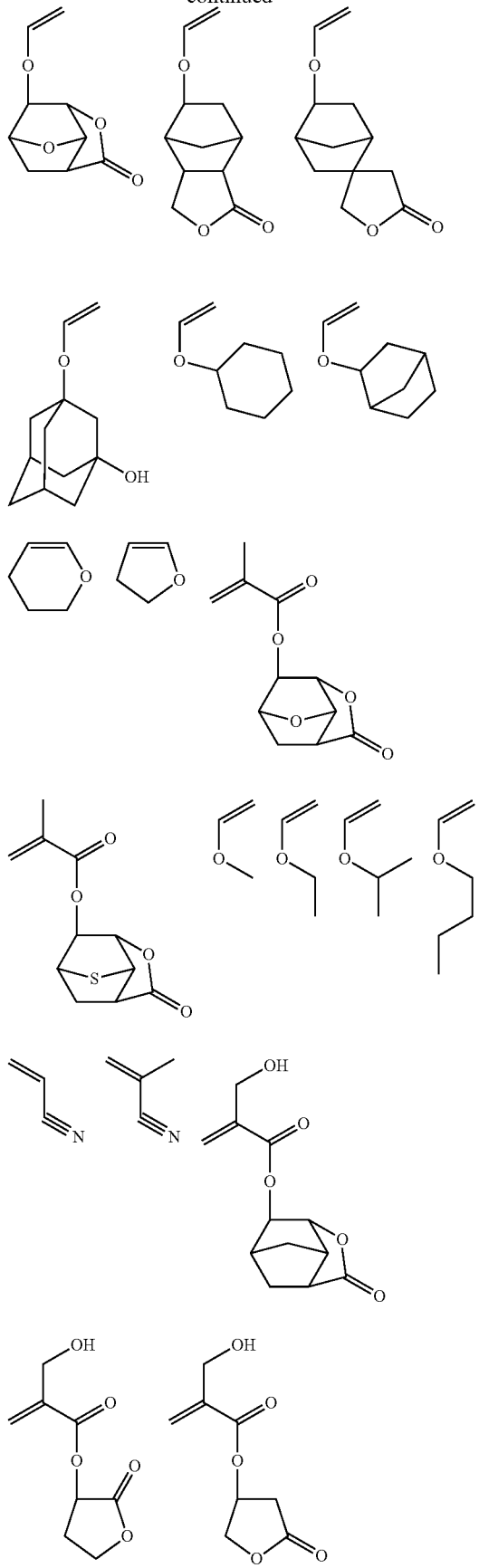

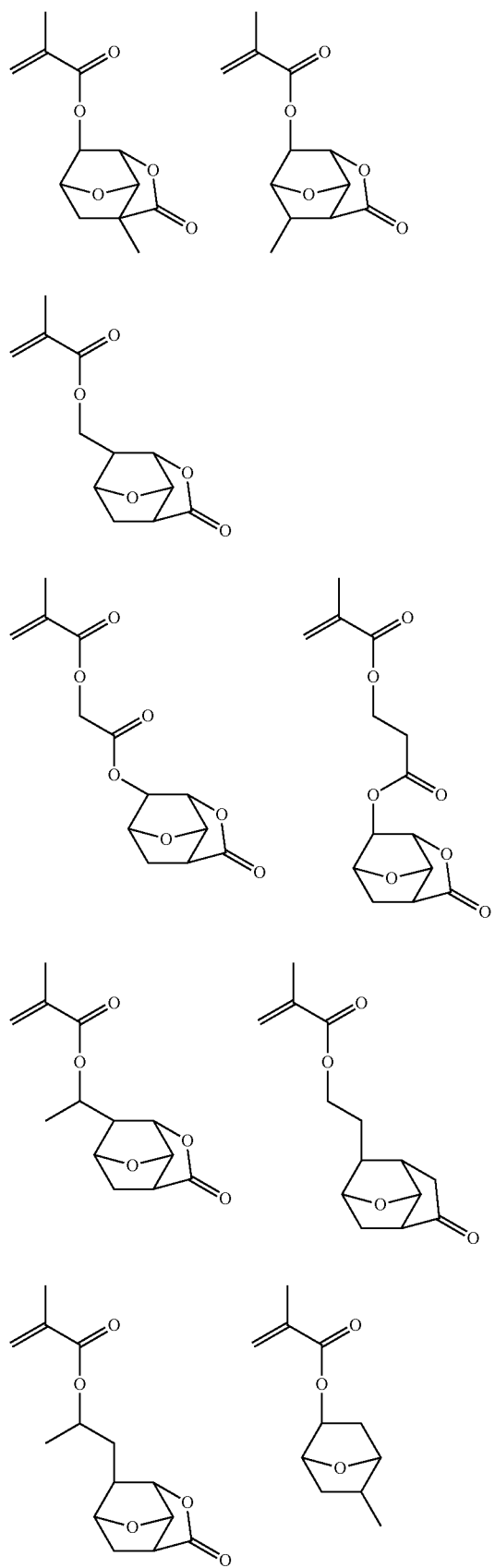
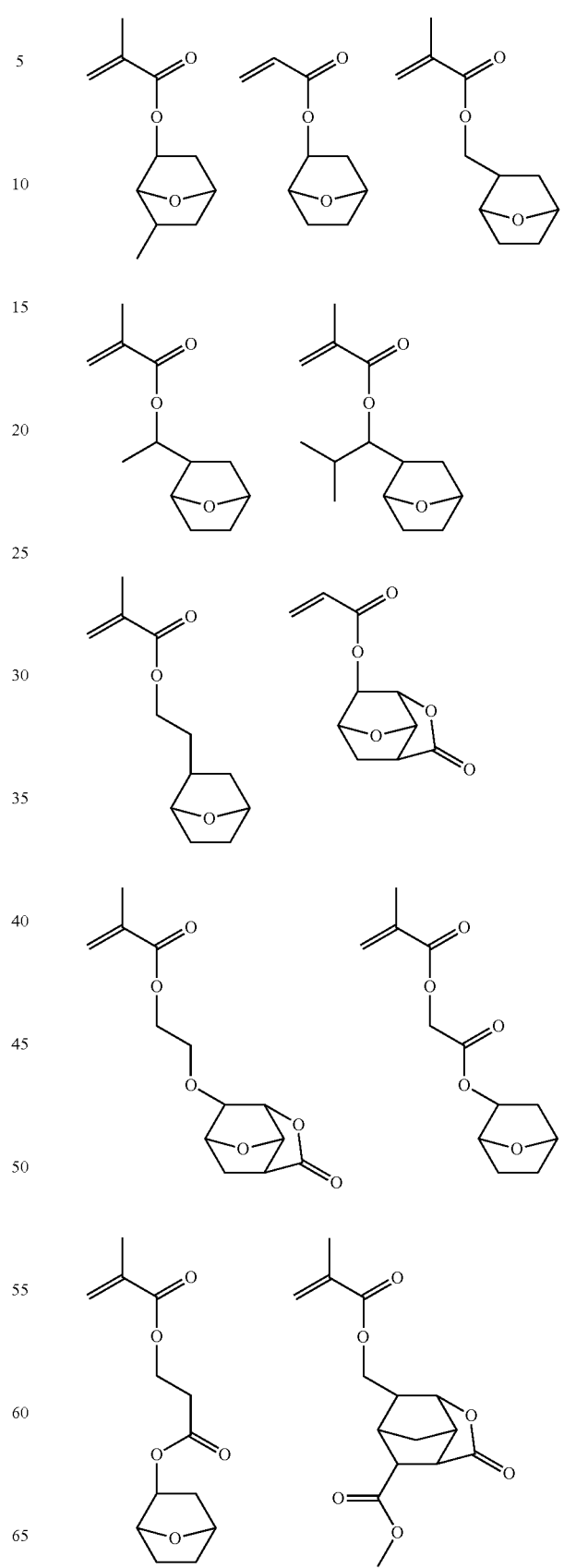

127
-continued
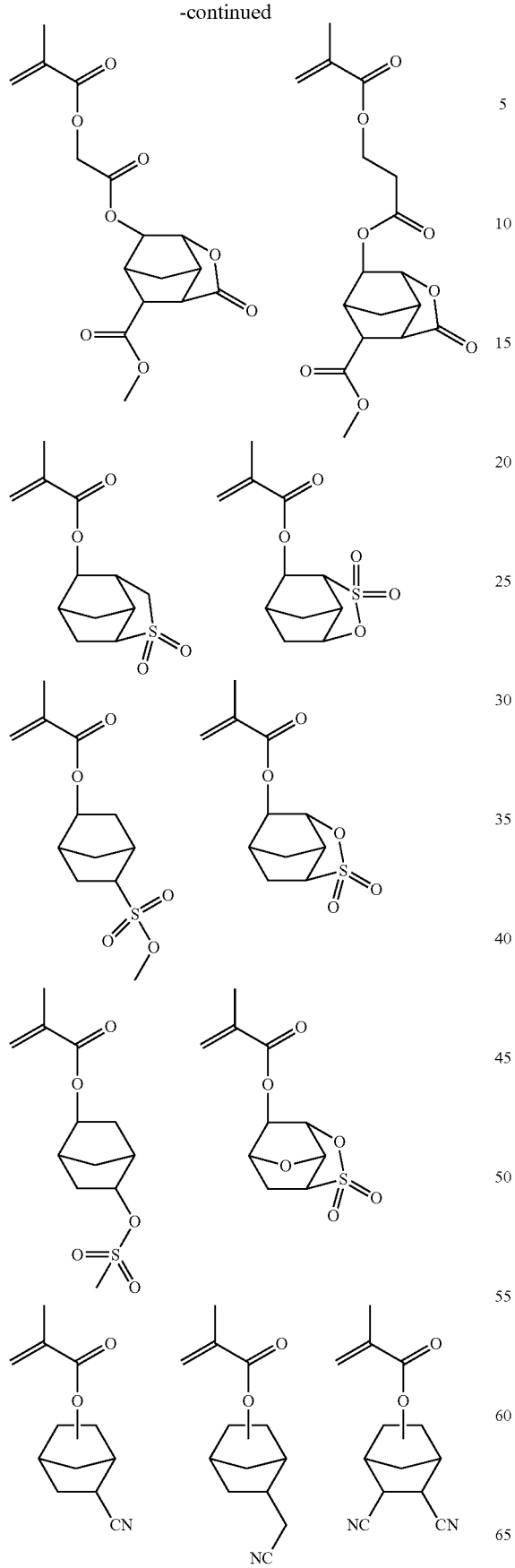
128
-continued
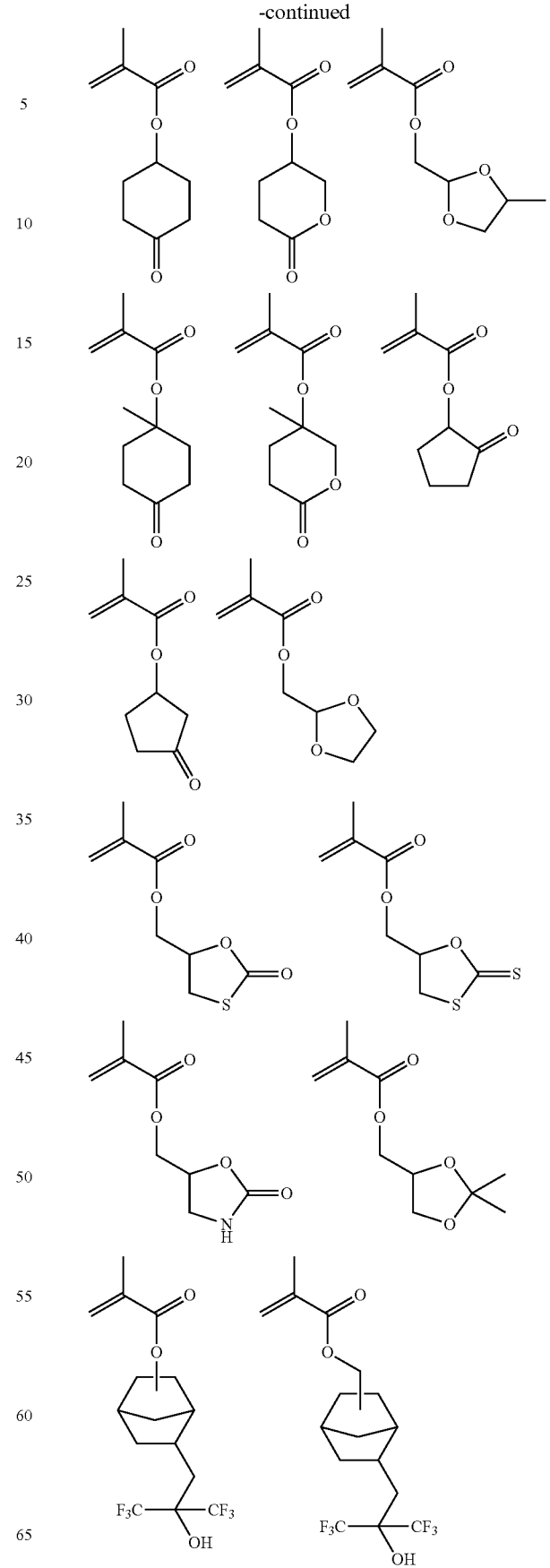

129
-continued
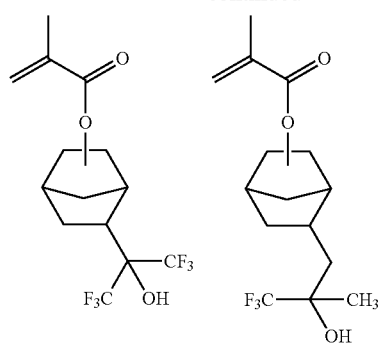
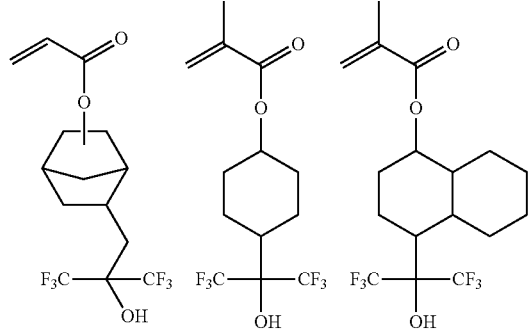
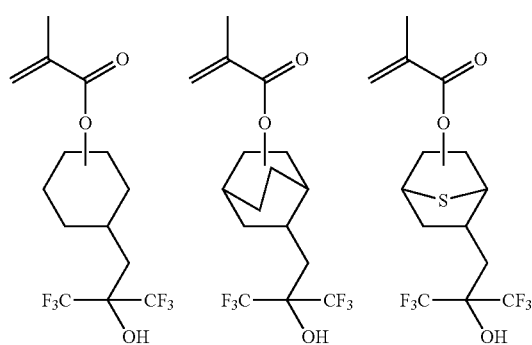
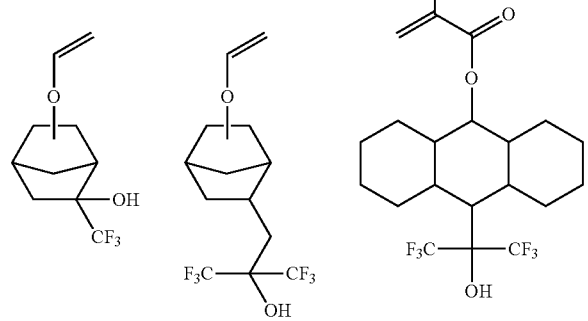
130
-continued
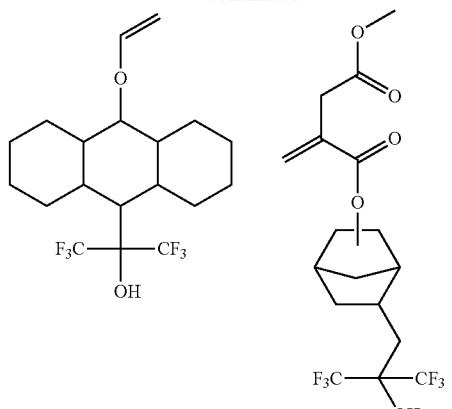
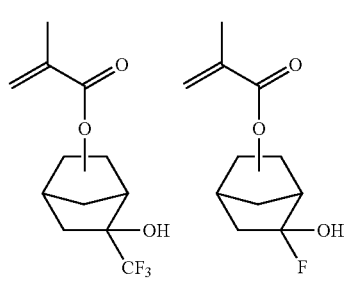
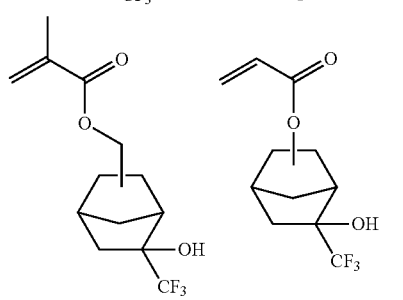
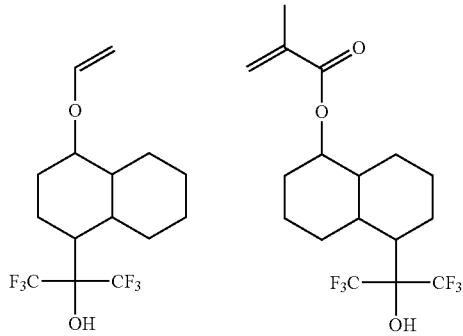
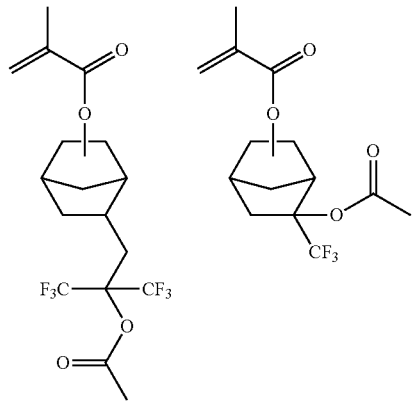

131
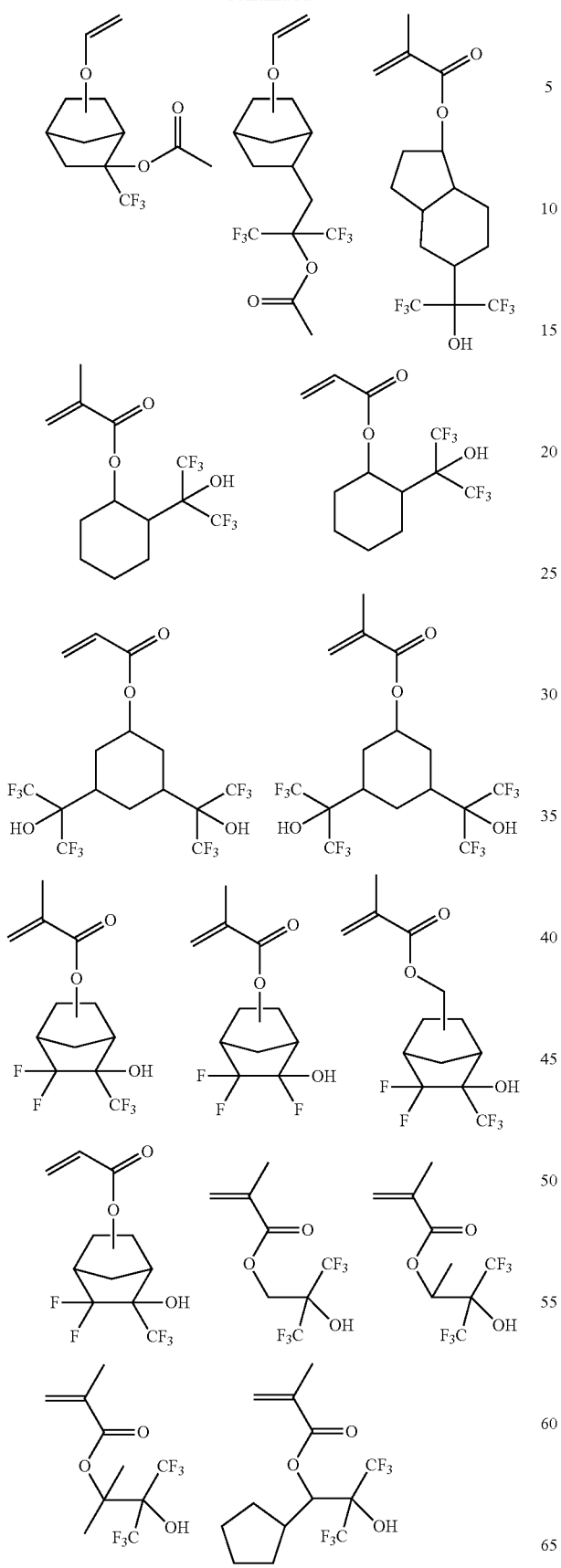
132
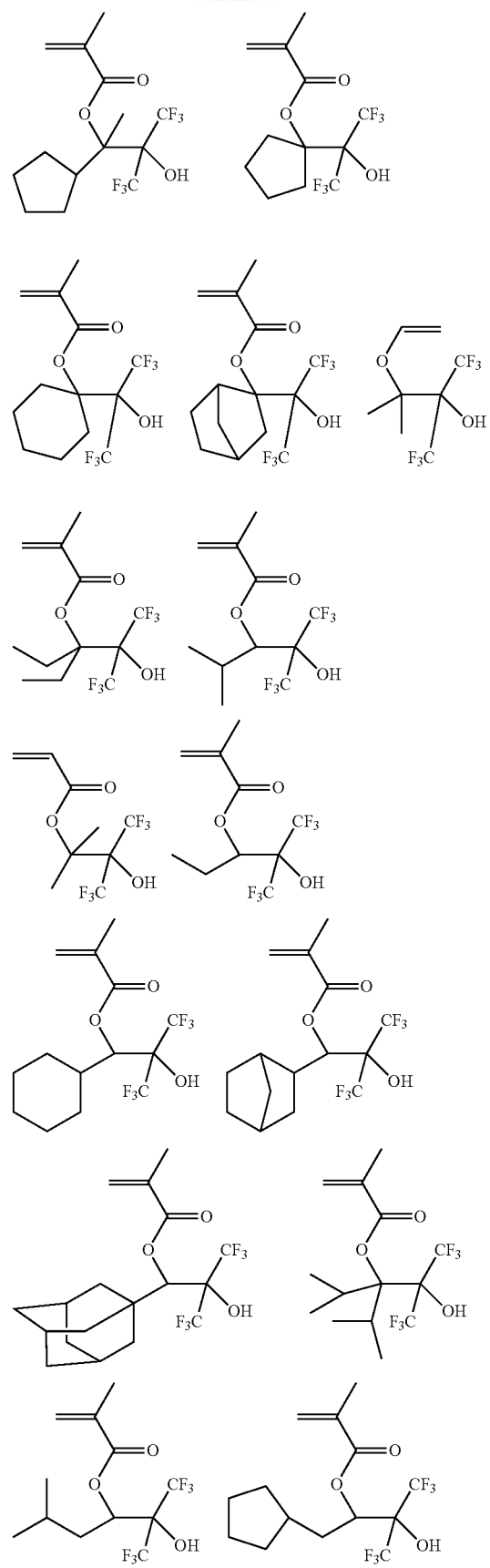

-continued
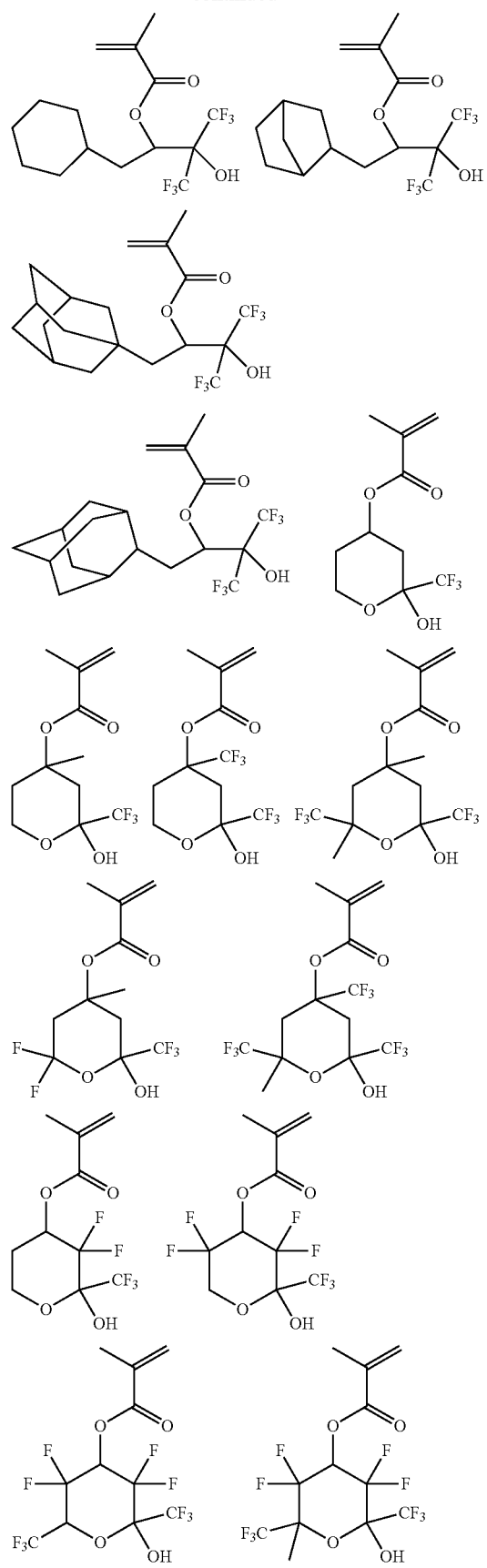
-continued
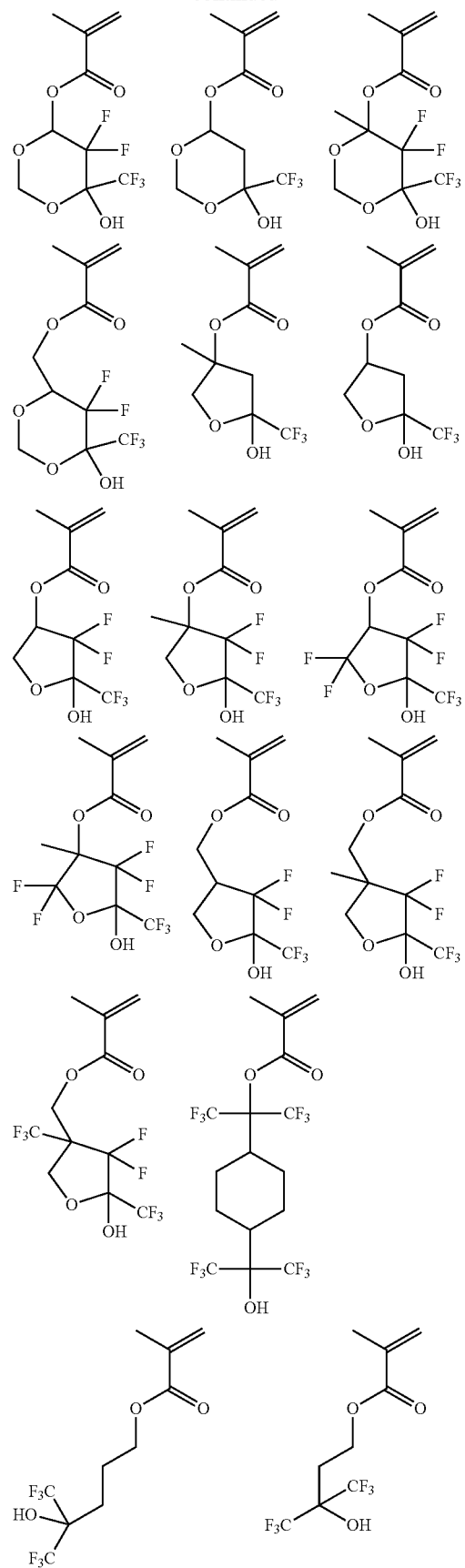

135
-continued
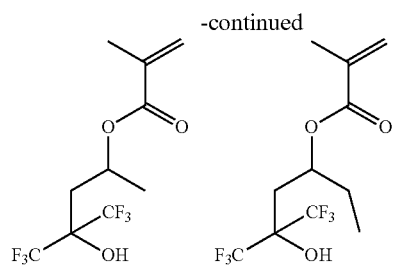
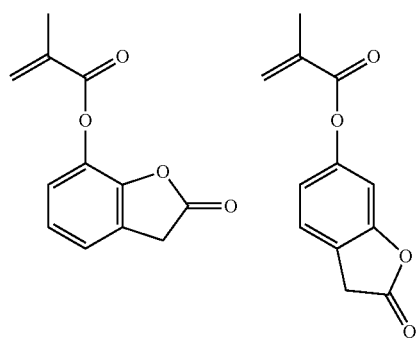
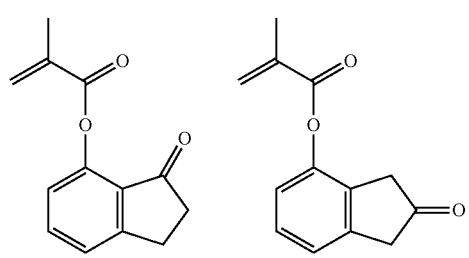
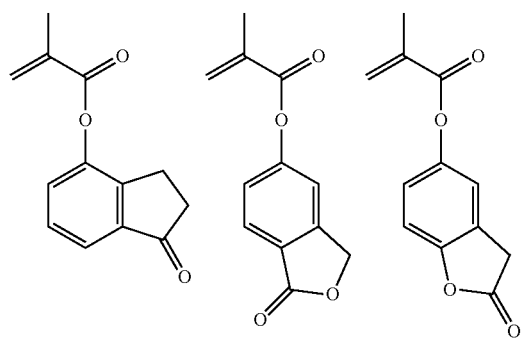
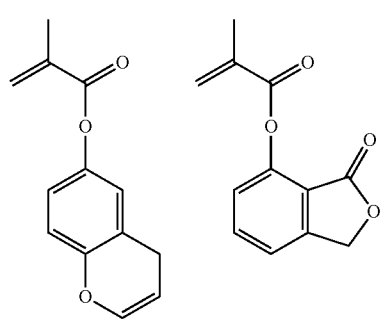
136
-continued
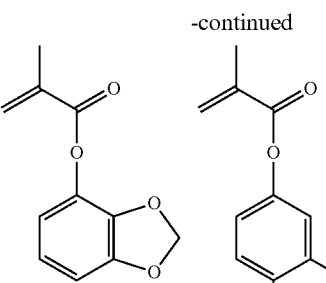
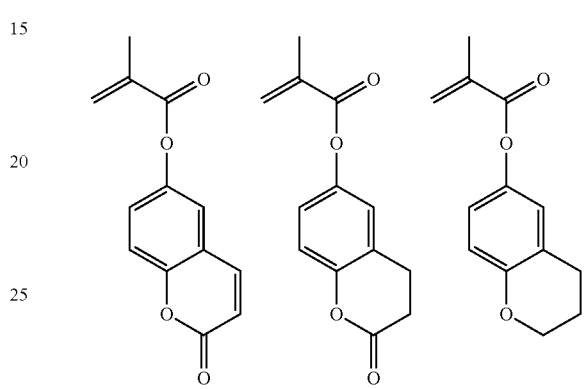
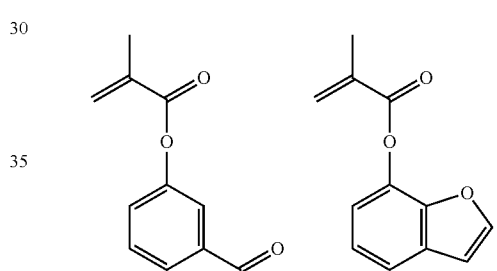
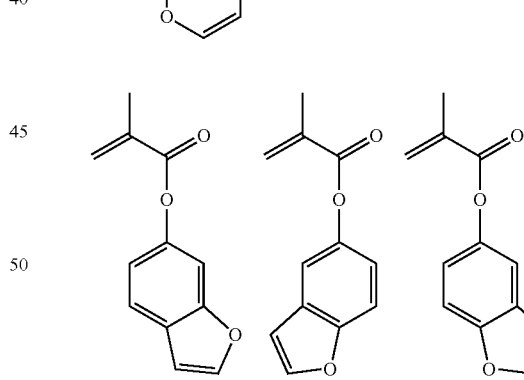
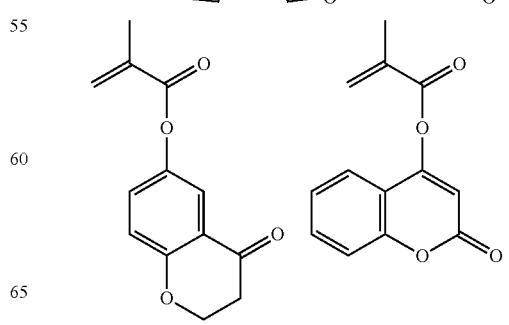

137
-continued
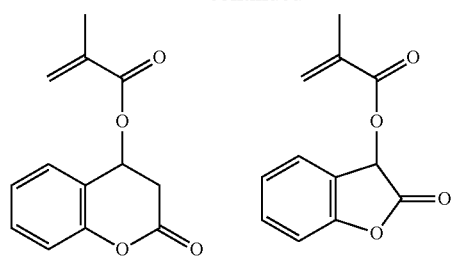
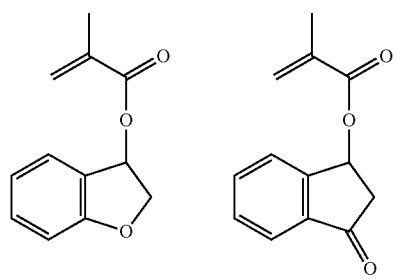
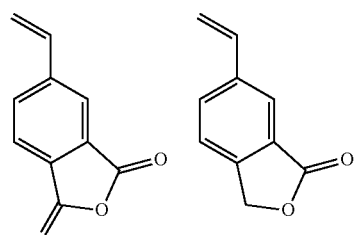
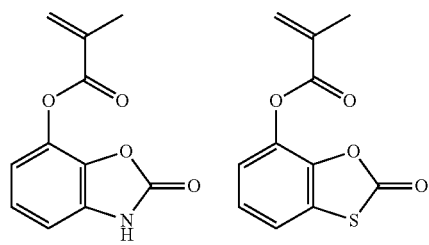
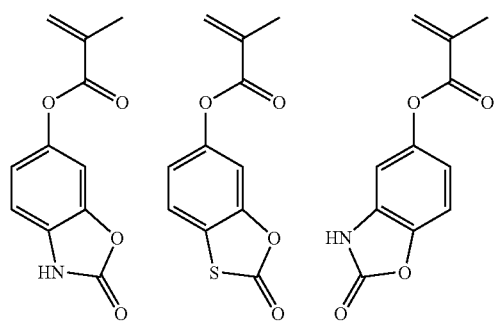
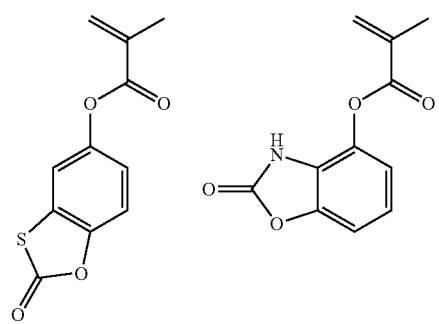
138
-continued
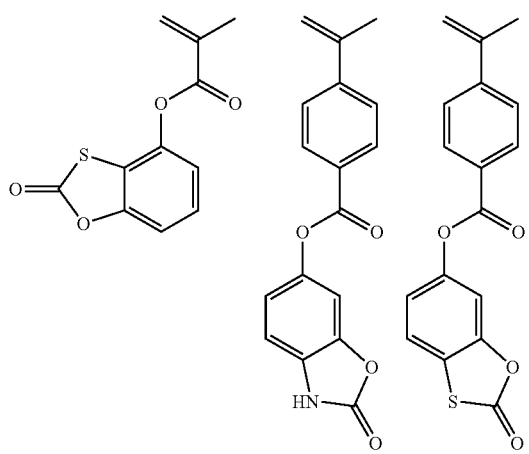
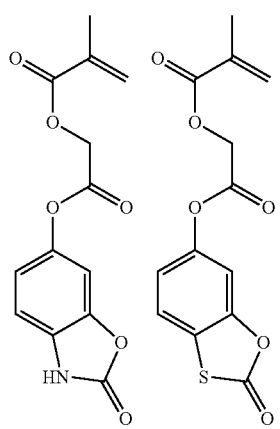
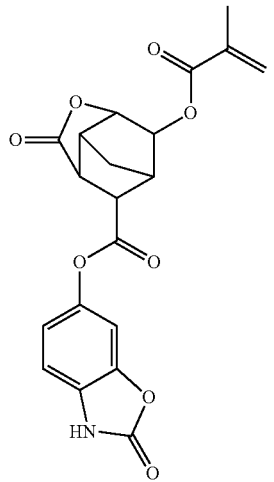

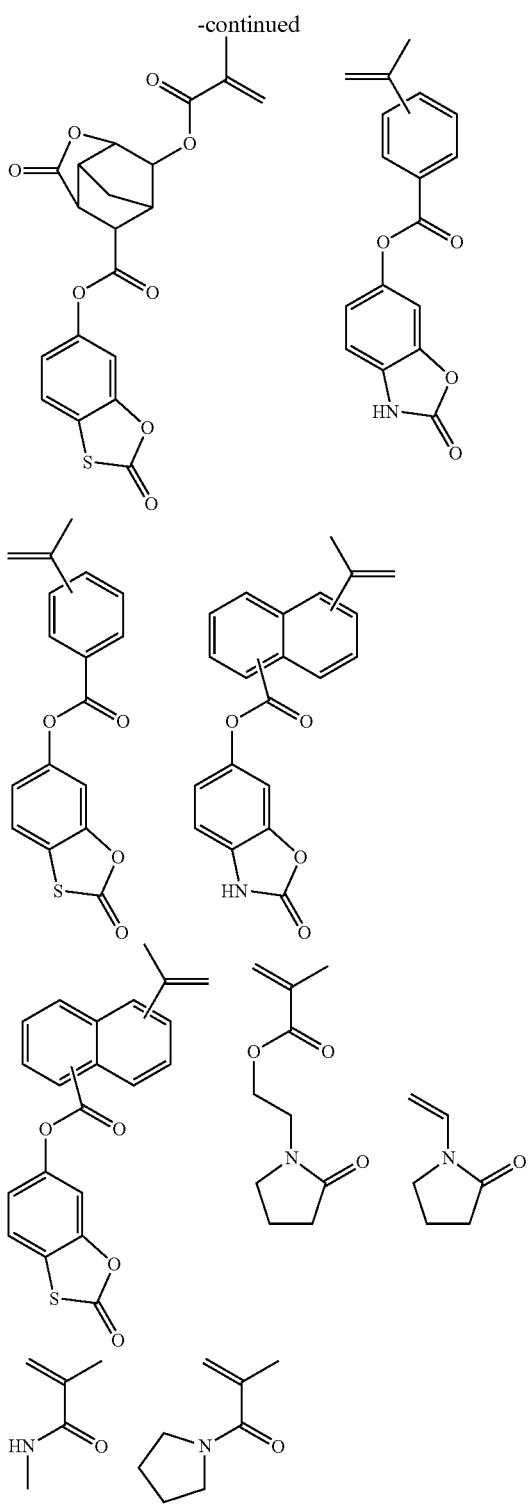

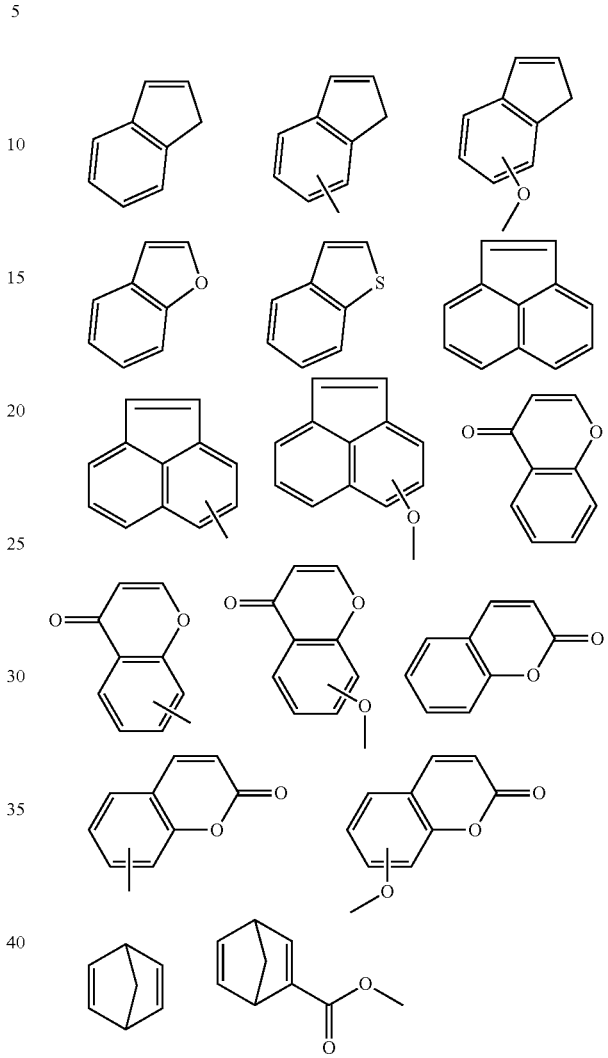

In the case of the polymerization of the monomer having a hydroxyl group, the hydroxyl group may be substituted with an acetal group such as an ethoxyethoxy group, which is easy to be deprotected by an acid, and then, this may be deprotected by a weak acid and water after polymerization thereof. Alternatively, the hydroxyl group may be substituted with an acetyl group, a formyl group, a pivaloyl group, or the like, and then, this may be subjected to an alkaline hydrolysis after polymerization thereof.

Further, indene, benzofuran, benzothiophene, acenaphthylene, chromone, cumarine, norbonadiene, and derivatives e thereof may be copolymerized. Illustrative examples thereof include the following compounds.

Examples of repeating unit f that can be copolymerized other than the above repeating units include styrene, vinylnaphthalene, vinylanthracene, vinylpyrene, and methyleneindane.

In the polymer compound that constitutes the base resin of the chemically amplified resist composition used in the patterning process of the present invention, the copolymerization ratio of the repeating units a1, a2, b1, b2, b3, c, d, e, and f is $0 \le a1 \le 0.9$, $0 \le a2 \le 0.9$, $0 < a1+a2 < 1.0$, $0 \le b1 \le 0.3$, $0 \le b2 \le 0.3$, $0 \le b3 \le 0.3$, $0 \le b1+b2+b3 \le 0.3$, $0 \le c < 1.0$, $0 \le d < 1.0$, $0 \le c+d < 1.0$, $0 \le e < 1.0$, $0 \le f < 1.0$, $0.7 \le a1+a2+b1+b2+b3+c+d \le 1.0$, preferably $0 \le a1 \le 0.8$, $0 \le a2 \le 0.8$, $0.1 \le a1+a2 \le 0.8$, $0 \le b1 \le 0.3$, $0 \le b2 \le 0.3$, $0 \le b3 \le 0.3$, $0 \le b1+b2+b3 \le 0.3$, $0 \le c \le 0.8$, $0 \le d \le 0.8$, $0.2 \le c+d \le 0.9$, $0 \le e \le 0.5$, $0 \le f \le 0.5$, $0.8 \le a1+a2+b1+b2+b3+c+d \le 1.0$, much more preferably $0 \le a1 \le 0.7$, $0 \le a2 \le 0.7$, $0.1 \le a1+a2 \le 0.7$, $0 \le b1 \le 0.3$, $0 \le b2 \le 0.3$, $0 \le b2 \le 0.3$, $0.02 \le b1+b2+b3 \le 0.3$, $0 \le c \le 0.7$, $0 \le b1 \le 0.3$, $0.28 \le c+d \le 0.88$, $0 \le e \le 0.4$, $0 \le f \le 0.4$, $0.85 \le a1+a2+b1+b2+b3+c+d \le 1.0$. Also, $a1+a2+b1+b2+b3+c+d+e+f=1.0$.

As the method for synthesizing the polymer compound, there may be mentioned copolymerization by subjecting the monomers corresponding to the repeating units a1 and/or a2, and if necessary, b1, b2, b3, and c to f to thermal polymerization in the presence of a radical polymerization initiator in an organic solvent.

Illustrative examples of the organic solvent used in the polymerization include toluene, benzene, tetrahydrofuran, diethyl ether, and dioxane. Illustrative examples of the polymerization initiator include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. These reaction materials can be polymerized by heating preferably at 50 to 80° C. The reaction time is in the range of 2 to 100 hours, preferably 5 to 20 hours.

In the case that hydroxystyrene or hydroxyvinyl-naphthalene is copolymerized, there is a method in which acetoxystyrene or acetoxyvinylnaphthalene, in place of hydroxystyrene or hydroxyvinylnaphthalene, is used for polymerization, followed by deprotection of these acetoxy groups by an alkaline hydrolysis to obtain polyhydroxystyrene or hydroxypolyvinylnaphthalene.

As to the base for the alkaline hydrolysis, an aqueous ammonia, triethylamine, and the like may be used. The reaction temperature is in the range of −20 to 100° C., preferably 0 to 60° C.; and the reaction time is in the range of 0.2 to 100 hours, preferably 0.5 to 20 hours.

Each polymer compound constituting the base resin of the chemically amplified resist composition used in the patterning process of the present invention preferably has a weight average molecular weight measured by gel permeation chromatography (GPC) in terms of polystyrene of 1,000 to 500,000, more preferably 2,000 to 300,000. If the weight average molecular weight is 1,000 or more, the resist composition is excellent in heat resistance; and when it is 500,000 or less, there is no possibility of lowering the solubility in alkaline solution and causing a footing profile after patterning.

In the polymer compound used in the resist composition, if the molecular weight distribution (Mw/Mn) of the multi-component copolymer is wide, there is possibility of foreign matters on the pattern or deterioration of the pattern profile after photo-exposure caused by a polymer having low molecular weight or high molecular weight. Accordingly, in order to obtain the resist composition advantageously usable for a fine pattern size, the molecular weight distribution of the multicomponent polymer compound to be used is preferably in the range of 1.0 to 2.0, particularly in a narrow range of 1.0 to 1.5, because influences of the molecular weight and the molecular weight distribution tend to become more significant as the pattern rule progresses toward further miniaturization.

The polymer compound shown herein is particularly suitable as the base resin of the positive resist composition; and thus, if this polymer compound is used as the base resin and is blended in an appropriate combination with an organic solvent, an acid generator, a dissolution control agent, a basic compound, a surfactant, acetylene alcohol, and so forth in accordance with the intended purpose to prepare a positive resist composition, the dissolution rate of this polymer compound into a developer by a catalytic reaction thereof is enhanced in the exposed part, thereby leading to a highly sensitive positive resist composition. In addition, the dissolution contrast and the resolution of the resist film can be made high, a large exposure margin can be realized, an excellent process adaptability can be obtained, and a further excellent etching resistance can be obtained with a good pattern profile after the photo-exposure. In particular, since the acid diffusion can be suppressed, the coarse-dense size difference of the resist composition can be reduced. Thus, the resist composition having the above polymer compound as the base resin is highly practical and effective as a resist composition for VLSI. Especially, a chemically amplified positive resist composition utilizing an acid catalyst reaction by incorporating an acid generator thereinto is suitably used in the patterning process of the present invention because sensitivity and various properties thereof can be further improved.

The positive resist composition used in the patterning process of the present invention may contain an acid generator as mentioned above. For example, a compound capable of generating an acid by responding to an active beam or a radiation beam (photo acid generator) may be contained therein. As to the photo acid generator component, a compound capable of generating an acid by exposure to a high energy beam can be used. Examples of the suitable photo acid generator include a sulfonium salt, an iodonium salt, a sulfonyldiazomethane, an N-sulfonyloxyimide, and an oxime-O-sulfonate type acid generator. These compounds may be used solely or as a mixture of two or more. Illustrative examples of the acid-generator are described in paragraphs (0122) to (0142) of Japanese Patent Laid-Open Publication No. 2008-111103. When the polymer compound having copolymerized repeating units b1 to b3 is used as the base resin, acid is generated without formulation of an acid generator.

Illustrative examples of the organic solvent are disclosed, for example, in paragraphs (0144) and (0145) of Japanese Patent Application Laid-Open No. 2008-111103, and include ketones such as cyclohexanone, cyclopentanone, and methyl-2-n-amyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; lactones such as γ-butyrolactone; and a mixed solvent thereof. Illustrative examples of the basic compound are disclosed in paragraphs (0146) to (0164) of said publication, and include primary, secondary, or tertiary amine compounds, particularly amine compounds having a hydroxyl group, an ether bond, an ester bond, a lactone ring, a cyano group, or a sulfonate bond.

Illustrative examples of the surfactant are disclosed in paragraphs (0165) and (0166) of Japanese Patent Application Laid-Open No. 2008-111103; the dissolution control agent in paragraphs (0155) to (0178) of Japanese Patent Laid-Open Publication No. 2008-122932; and the acetylene alcohols in paragraphs (0179) to (0182) of the same. Also, a polymer type quencher described in Japanese Patent Laid-Open Publication No. 2008-239918 may also be added. The polymer type quencher can enhance rectangularity of the resist pattern after development by applying it to the resist surface after coating. The polymer-type quencher also has the effects to prevent film loss of the pattern when a top coat for immersion exposure is formed thereon as well as rounding of the pattern head.

The formulation amount of the acid generator is preferably 0.01 to 100 parts by mass, particularly 0.1 to 80 parts by mass based on 100 parts by mass of the base resin. The formulation amount of the organic solvent is preferably 50 to 10,000 parts by mass, particularly 100 to 5,000 parts by mass based on 100 parts by mass of the base resin. The formulation amount of the dissolution control agent is preferably 0 to 50 parts by mass, particularly 0 to 40 parts by mass, the formulation amount of the basic compound is preferably 0 to 100 parts by mass, particularly 0.001 to 50 parts by mass, and the formulation amount of the surfactant is preferably 0 to 10 parts by mass, particularly 0.0001 to 5 parts by mass, based on 100 parts by mass of the base resin.

In particular, the photosensitive resist composition used in the patterning process of the present invention preferably contains any one or more of an organic solvent, a basic compound, a dissolution control agent, and a surfactant.

In the patterning process of the present invention, when the chemically amplified positive resist composition that contains an organic solvent, a polymer compound containing the repeating unit having an acid-labile group, represented by the general formula (2), an acid generator, and a basic compound, is used for manufacturing of various integrated circuits, known lithography techniques can be used, although it is not particularly limited thereto.

For example, the positive resist composition is applied onto a substrate for the integrated circuit manufacturing (Si, $SiO_2$, SiN, SiON, TiN, WSi, BPSG, SOG, an organic anti-reflective film, and so forth) or onto a substrate for the mask circuit manufacturing (Cr, CrO, CrON, MoSi, $SiO_2$, and so forth) by an appropriate coating method including a spin coating, a roll coating, a flow coating, a dip coating, a spray coating, and a doctor coating, so as to give a film thickness of 0.1 to 2.0 μm. This is then pre-baked on a hot plate at a temperature ranging from 60 to 150° C. for 10 seconds to 30 minutes, preferably at 80 to 120° C. for 30 seconds to 20 minutes.

Then, the intended pattern is exposed directly or through a prescribed mask to a light source selected from high energy beam such as an ultraviolet beam, a far ultraviolet beam, an electron beam, a X-ray beam, an excimer laser, a γ-beam, a synchrotron radiation beam, a vacuum ultraviolet beam (soft X-ray), and the like. The exposure is preferably done such that the exposure amount is in the range of about 1 to 200 $mJ/cm^2$, preferably 10 to 100 $mJ/cm^2$, or about 0.1 to 100 μC, preferably 0.5 to 50 μC. As the high energy beam, a KrF excimer laser having a wavelength of 248 nm, an ArF excimer laser having a wavelength of 193 nm, an electron beam, or a soft X-ray having a wavelength of 3 to 15 nm is preferably used.

Then, post exposure bake (PEB) is performed on a hot plate at a temperature ranging from 60 to 150° C. for 10 seconds to 30 minutes, preferably 80 to 120° C. for 30 seconds to 20 minutes.

Next, the development is performed by the developer containing the compound represented by the general formula (1) of the present invention. The development time is in the range of 1 to 300 seconds, preferably 3 to 100 seconds, and the temperature is in the range of 0 to 30° C., preferably 5 to 25° C. If the photosensitive resist composition is developed with the developer of the present invention, the occurrence of pattern collapse and bridge defect can be prevented by reducing swell of the resist film in the developer, thereby enabling a resist pattern with small edge roughness to be obtained.

After completion of the development, rinsing is preferably carried out. The rinsing after development is generally carried out by pure water, followed by spin drying. Alternatively, the rinsing may be carried out by pure water containing a surfactant. When a surfactant is used for rinsing, the pattern stress during spin drying and thus pattern collapse can be reduced. The pure water may be substituted with supercritical carbon dioxide to evaporate the solid carbon oxide without passing through the liquid state. In this case, drying is performed without the surface tension, so that pattern collapse hardly occurs. However, since it requires a specific chamber for making supercritical state under high pressure, throughput is remarkably lowered.

As mentioned above, the inventive patterning process using the inventive developer can prevent pattern collapse and bridge defect, and can provide a resist patter with small edge roughness.

EXAMPLES

Hereinafter, the present invention will be specifically described with reference to Examples and Comparative examples, but the present invention is not restricted thereto.

Examples and Comparative Examples

Preparation of Developer

Developers 1 to 4 were prepared with the composition shown in Table 1.

TABLE 1

|  | Compound shown in general formula (1) (parts by mass) | Surfactant (parts by mass) | Water (parts by mass) |
| --- | --- | --- | --- |
| Developer 1 | Hexamethonium hydroxide (3.10) | — | (97) |
| Developer 2 | Hexamethonium hydroxide (2.36) | Acetylene alcohol 1 (0.1) | (97) |
| Developer 3 | Decamethonium hydroxide (3.82) | — | (96) |
| Developer 4 | Succinylcholine hydroxide (4.23) | — | (96) |

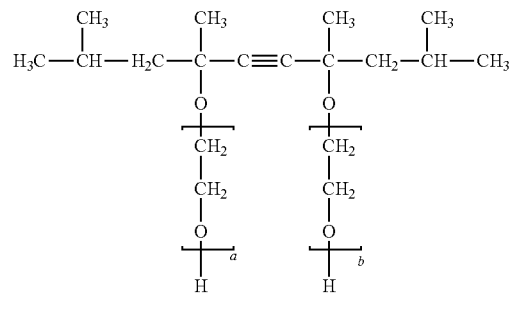

Acetylene alcohol 1 a + b = 30

(Preparation of Resist Composition)

The following resist polymer obtained by usual radical polymerization, a photo acid generator (PAG), a quencher, and a surfactant were dissolved in a solvent with the composition shown in Table 2, and the solution was filtered through a 0.2-μm filter to prepare Positive resist compositions 1 to 5.

TABLE 2

| | Polymer (parts by mass) | PAG (parts by mass) | Quencher (parts by mass) | Surfactant (parts by mass) | Solvent (parts by mass) |
|---|---|---|---|---|---|
| Positive resist composition 1 | Resist polymer 1 (100) | — | Quencher 1 (1.123) | FC-4430 (0.001) | PGMEA (2,000) PGME (1,000) Cyclohexanone (3,000) |
| Positive resist composition 2 | Resist polymer 2 (100) | — | Quencher 1 (1.123) | FC-4430 (0.001) | PGMEA (2,000) PGME (1,000) Cyclohexanone (3,000) |
| Positive resist composition 3 | Resist polymer 3 (100) | — | Quencher 1 (1.123) | FC-4430 (0.001) | PGMEA (2,000) PGME (1,000) Cyclohexanone (3,000) |
| Positive resist composition 4 | Resist polymer 4 (100) | — | Quencher 1 (1.123) | FC-4430 (0.001) | PGMEA (2,000) PGME (1,000) Cyclohexanone (3,000) |
| Positive resist composition 5 | Resist polymer 5 (100) | PAG 1 (25) | Quencher 2 (5.00) | FC-4430 (0.001) | PGMEA (4,000) Cyclohexanone (2,000) |

PGMEA: propylene glycol monomethyl ether acetate
PGME: propylene glycol monomethyl ether
FC-4430: fluorine based surfactant, manufactured by Sumitomo 3M, Ltd.)

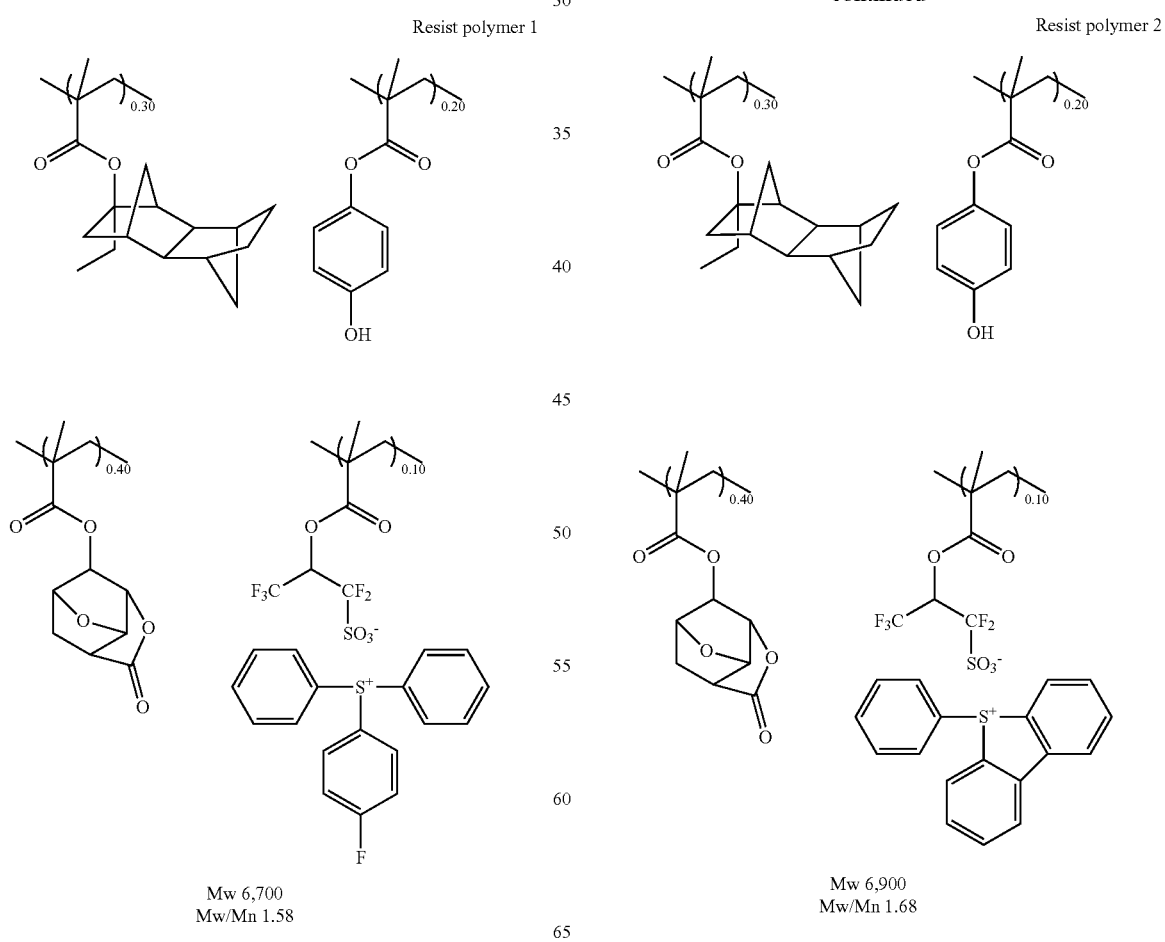

Resist polymer 1

Resist polymer 2

Mw 6,700
Mw/Mn 1.58

Mw 6,900
Mw/Mn 1.68

-continued
Resist polymer 3
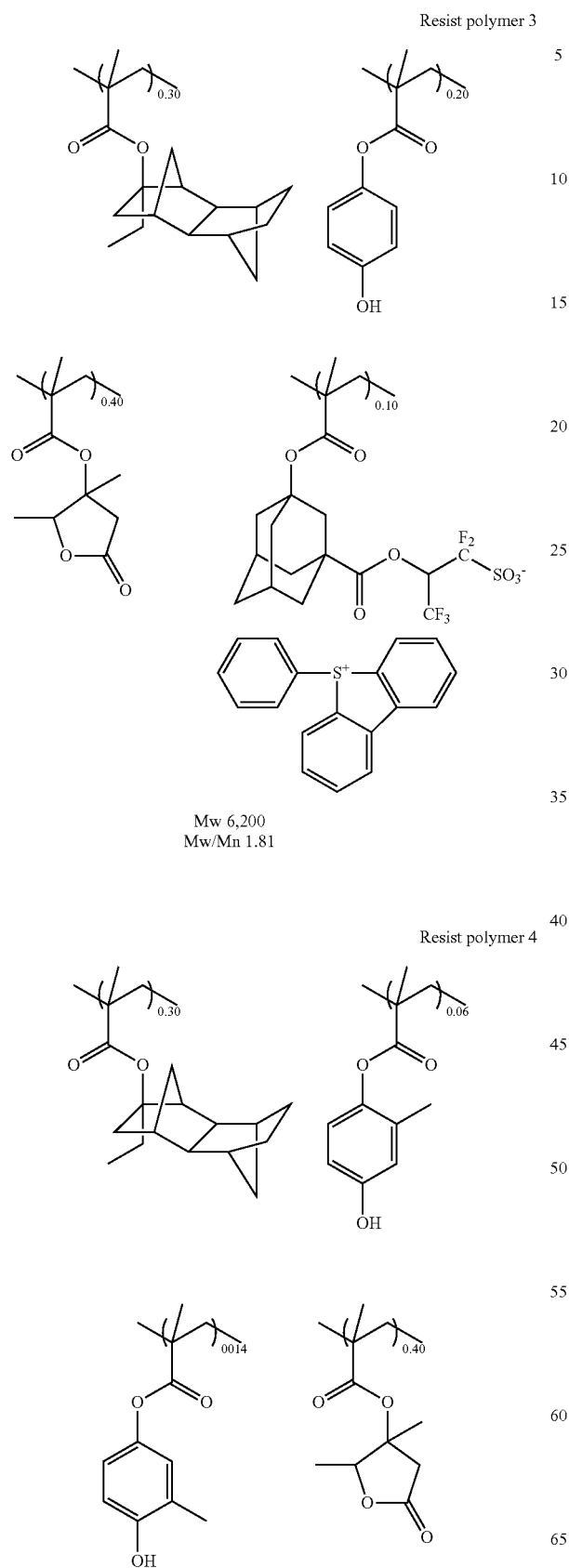
Mw 6,200
Mw/Mn 1.81
Resist polymer 4
-continued
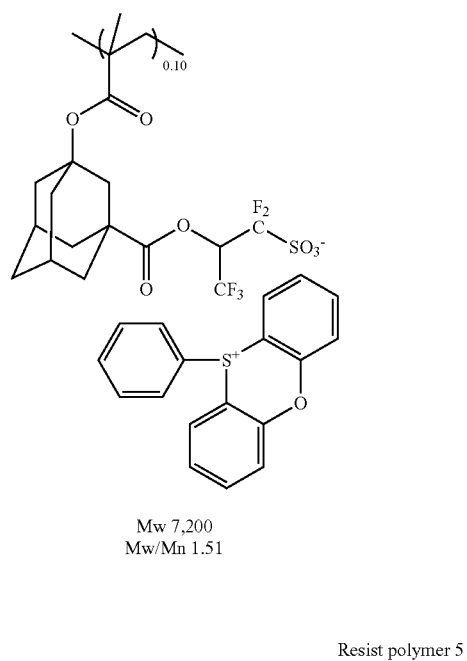
Mw 7,200
Mw/Mn 1.51
Resist polymer 5
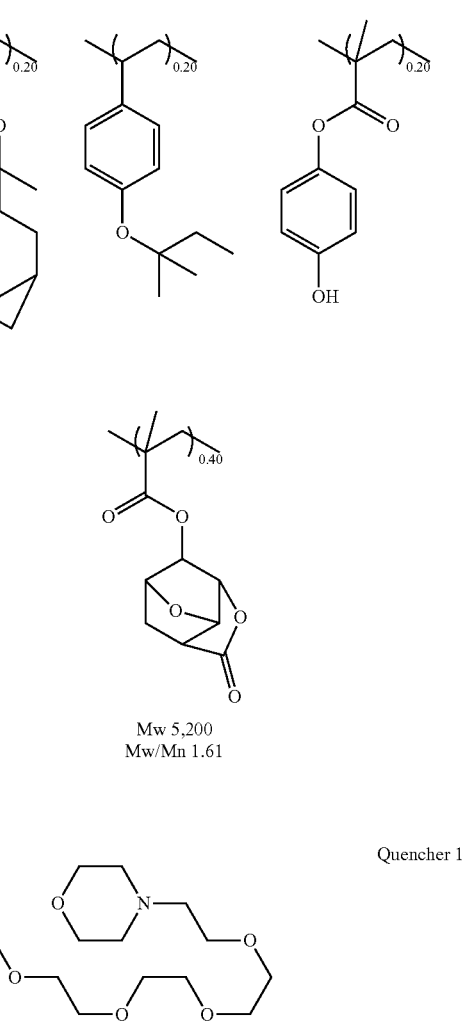
Mw 5,200
Mw/Mn 1.61
Quencher 1

-continued

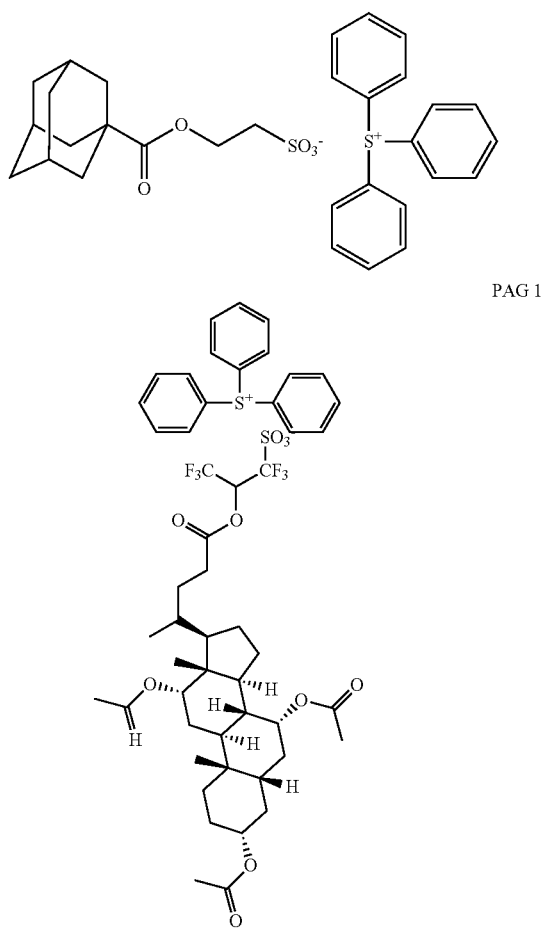

Quencher 2

PAG 1

(EUV Evaluation)

Positive resist compositions 1 to 5 thus prepared were each applied onto a silicon-containing SOG film, SHB-A940 (available from Shin-Etsu Chemical Co., Ltd.) with a film thickness of 35 nm laminated on a 4-inches (100 nm) Si substrate, and then pre-baked on a hot plate at 110° C. for 60 seconds to form a resist film having a thickness of 35 nm. This film was exposed to EUV by using Pseudo PSM (phase shift mask) with NA=0.3, and PEB was performed under temperature condition shown in Table 3. Then, development was performed with Developers 1 to 4 prepared above, an aqueous TMAH solution, or an aqueous TBAH solution for 20 seconds, followed by rinsing and spin-drying to form a resist pattern. The sensitivity when a 20-nm line and space pattern was formed, the limiting resolution of the minimum resolvable dimension at this time, and edge roughness (LWR) was measured by a scanning electron microscope (SEM). As the rinsing liquid, pure water or Extreme 10 (available from AZ electronic materials Ltd.) was used. The results were shown in Table 3. Note that the limiting resolution was determined by pattern collapse. The higher limiting resolution (i.e., the smaller value of limiting resolution) means that pattern collapse and bridge defect hardly occur.

TABLE 3

| | Resist | PEB temperature (° C.) | Developer | Rinsing liquid | Sensitivity (mJ/cm$^2$) | Limiting resolution (nm) | LWR (nm) |
|---|---|---|---|---|---|---|---|
| Example 1 | Positive resist composition 1 | 90 | Developer 1 | Pure water | 14 | 18 | 4.5 |
| Example 2 | Positive resist composition 2 | 85 | Developer 1 | Extreme 10 | 15 | 16 | 4.6 |
| Example 3 | Positive resist composition 3 | 85 | Developer 1 | Extreme 10 | 15 | 16 | 4.1 |
| Example 4 | Positive resist composition 4 | 85 | Developer 1 | Extreme 10 | 16 | 16 | 4.8 |
| Example 5 | Positive resist composition 5 | 85 | Developer 1 | Extreme 10 | 17 | 15 | 4.9 |
| Example 6 | Positive resist composition 4 | 85 | Developer 2 | Extreme 10 | 18 | 16 | 4.7 |
| Example 7 | Positive resist composition 4 | 85 | Developer 3 | Extreme 10 | 18 | 16 | 4.1 |
| Example 8 | Positive resist composition 4 | 85 | Developer 4 | Extreme 10 | 18 | 16 | 4.6 |

TABLE 3-continued

| Resist | | PEB temperature (° C.) | Developer | Rinsing liquid | Sensitivity (mJ/cm²) | Limiting resolution (nm) | LWR (nm) |
|---|---|---|---|---|---|---|---|
| Comparative example 1 | Positive resist composition 4 | 85 | 2.38% by mass aqueous TMAH solution | Pure water | 20 | 20 | 5.6 |
| Comparative example 2 | Positive resist composition 4 | 85 | 2.38% by mass aqueous TMAH solution | Extreme 10 | 20 | 19 | 5.2 |
| Comparative example 3 | Positive resist composition 4 | 85 | 6.77% by mass aqueous TBAH solution | Extreme 10 | 21 | 18 | 5.9 |

TMAH: tetramethylammonium hydroxide
TBAH: tetrabutylammonium hydroxide

From the above results, it was revealed that Examples 1 to 8, in which the pattern was formed by using the developer of the present invention, showed high sensitivity of the resist film, could prevent pattern collapse and bridge defect, and could provide a resist pattern with small edge roughness, compared with Comparative examples 1 to 3, which used the conventional developer.

It should be noted that the present invention is not limited to the foregoing embodiment. The embodiment is just an exemplification, and any examples that have substantially the same feature and demonstrate the same functions and effects as those in the technical concept described in claims of the present invention are included in the technical scope of the present invention.

What is claimed is:

1. A developer for a photosensitive resist composition, comprising water and a compound represented by the general formula (1)

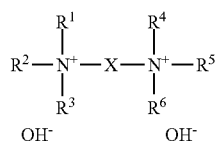

wherein $R^1$ to $R^6$ represent a linear, branched, or cyclic alkyl group having 1 to 4 carbon atoms; and X represents a linear or branched alkylene group having 6 to 16 carbon atoms and optionally having an ester group.

2. The developer according to claim 1, wherein the compound represented by the general formula (1) is contained in an amount of 0.1 to 20% by mass based on a total amount of the developer.

3. The developer according to claim 1, wherein the compound represented by the general formula (1) is any of hexamethonium hydroxide, decamethonium hydroxide, and succinylcholine hydroxide.

4. The developer according to claim 2, wherein the compound represented by the general formula (1) is any of hexamethonium hydroxide, decamethonium hydroxide, and succinylcholine hydroxide.

5. The developer according to claim 1, further comprising 0.0001 to 5% by mass of an acetylene alcohol represented by the general formula (AA-1),

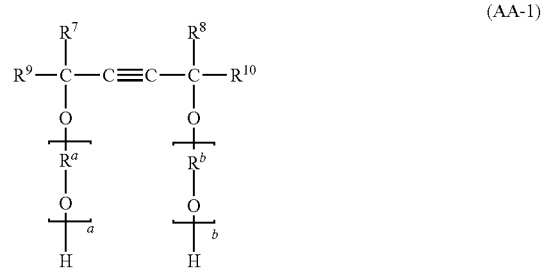

wherein $R^7$ to $R^{10}$ each represent an identical or different alkyl group having 1 to 20 carbon atoms; $R^a$ and $R^b$ each represent an identical or different alkylene group having 1 to 10 carbon atoms; and "a" and "b" are each an integer satisfying $0 \leq a+b \leq 60$.

6. The developer according to claim 2, further comprising 0.0001 to 5% by mass of an acetylene alcohol represented by the general formula (AA-1),

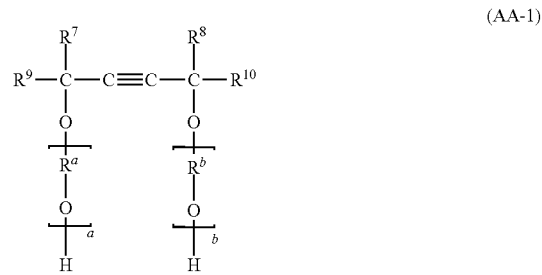

wherein $R^7$ to $R^{10}$ each represent an identical or different alkyl group having 1 to 20 carbon atoms; $R^a$ and $R^b$ each represent an identical or different alkylene group having 1 to 10 carbon atoms; and "a" and "b" are each an integer satisfying $0 \leq a+b \leq 60$.

7. The developer according to claim 3, further comprising 0.0001 to 5% by mass of an acetylene alcohol represented by the general formula (AA-1),

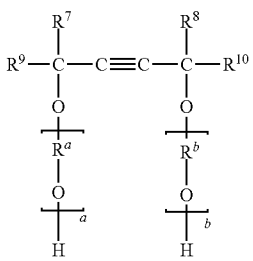

(AA-1)

wherein $R^7$ to $R^{10}$ each represent an identical or different alkyl group having 1 to 20 carbon atoms; $R^a$ and $R^b$ each represent an identical or different alkylene group having 1 to 10 carbon atoms; and "a" and "b" are each an integer satisfying $0 \leq a+b \leq 60$.

8. The developer according to claim 4, further comprising 0.0001 to 5% by mass of an acetylene alcohol represented by the general formula (AA-1),

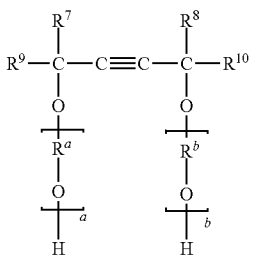

(AA-1)

wherein $R^7$ to $R^{10}$ each represent an identical or different alkyl group having 1 to 20 carbon atoms; $R^a$ and $R^b$ each represent an identical or different alkylene group having 1 to 10 carbon atoms; and "a" and "b" are each an integer satisfying $0 \leq a+b \leq 60$.

9. A patterning process comprising the steps of: applying a photosensitive resist composition onto a substrate; performing exposure to a high energy beam after heat treatment; performing development by using the developer according to claim 1.

10. A patterning process comprising the steps of: applying a photosensitive resist composition onto a substrate; performing exposure to a high energy beam after heat treatment; performing development by using the developer according to claim 2.

11. A patterning process comprising the steps of: applying a photosensitive resist composition onto a substrate; performing exposure to a high energy beam after heat treatment; performing development by using the developer according to claim 3.

12. A patterning process comprising the steps of: applying a photosensitive resist composition onto a substrate; performing exposure to a high energy beam after heat treatment; performing development by using the developer according to claim 4.

13. A patterning process comprising the steps of: applying a photosensitive resist composition onto a substrate; performing exposure to a high energy beam after heat treatment; performing development by using the developer according to claim 5.

14. A patterning process comprising the steps of: applying a photosensitive resist composition onto a substrate; performing exposure to a high energy beam after heat treatment; performing development by using the developer according to claim 6.

15. The patterning process according to claim 9, wherein the photoresist composition is a chemically amplified positive resist composition an alkali dissolution rate of which is increased by acid.

16. The patterning process according to claim 15, wherein a base resin of the chemically amplified positive resist composition is a polymer compound that contains a repeating unit having an acid-labile group and a repeating unit having an hydroxyl group and/or a lactone ring as an adhesive group.

17. The patterning process according to claim 16, wherein the polymer compound has a weight average molecular weight within a range of 1,000 to 500,000, and the repeating unit having an acid-labile group is one or more repeating units selected from repeating units a1 and a2 represented by the general formula (2), in which a hydrogen atom of a carboxyl group or a phenolic hydroxyl group is substituted with an acid-labile group,

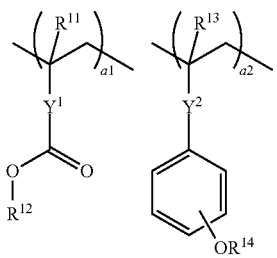

(2)

wherein $R^{11}$ and $R^{13}$ independently represent a hydrogen atom or a methyl group; $R^{12}$ and $R^{14}$ represent an acid-labile group; $Y^1$ represents a single bond or a divalent linking group having 1 to 12 carbon atoms and any one or more of an ester group, a lactone ring, a phenylene group, and a naphthylene group; $Y^2$ represents a single bond, an ester group, or an amide group; $0 \leq a1 \leq 0.9$; $0 \leq a2 \leq 0.9$; and $0 < a1+a2 < 1.0$.

18. The patterning process according to claim 17, wherein the polymer compound further contains one or more repeating units selected from repeating units b1 to b3 having a sulfonium salt structure represented by the general formula (3),

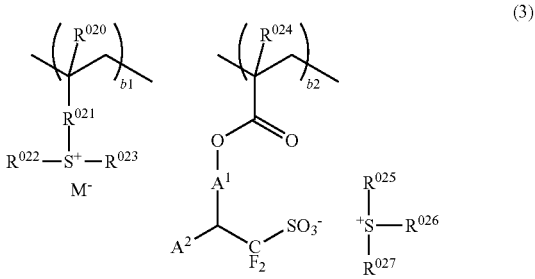

(3)

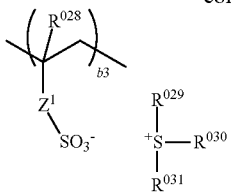

wherein $R^{020}$, $R^{024}$, and $R^{028}$ represent a hydrogen atom or a methyl group; $R^{021}$ represents a single bond, a phenylene group, —O—$R^{033}$—, or —C(=O)—Y—$R^{033}$—, where Y represents an ether group or a NH group, and $R^{033}$ represents a phenylene group or a linear, branched, or cyclic alkylene group or alkenylene group having 1 to 6 carbon atoms and optionally containing a carbonyl group, an ester group, an ether group, or a hydroxyl group; $R^{022}$, $R^{023}$, $R^{025}$, $R^{026}$, $R^{027}$, $R^{029}$, $R^{030}$, and $R^{031}$ may be the same or different and represent a linear, branched, or cyclic alkyl group having 1 to 12 carbon atoms and optionally containing a carbonyl group, an ester group, or an ether group, an aryl group having 6 to 12 carbon atoms, an aralkyl group having 7 to 20 carbon atoms, or a thiophenyl group; $A^1$ represents a single bond, -$A^0$-C(=O)—O—, -$A^0$-O—, or -$A^0$-O—C(=O)—, where $A^0$ represents a linear, branched, or cyclic alkylene group having 1 to 12 carbon atoms and optionally containing a carbonyl group, an ester group, or an ether group; $A^2$ represents a hydrogen atom, a $CF_3$ group, or =O; $Z^1$ represents a single bond, a methylene group, an ethylene group, a phenylene group, a fluorinated phenylene group, —O—$R^{032}$—, or —C(=O)—$Z^2$—$R^{032}$—, where $Z^2$ represents an ether group or a NH group, and $R^{032}$ represents a phenylene group, a fluorinated phenylene group, a phenylene group substituted with a trifluoromethyl group, or a linear, branched, or cyclic alkylene group or alkenylene group having 1 to 6 carbon atoms and optionally containing a carbonyl group, an ester group, an ether group, or a hydroxyl group; $M^-$ represents a non-nucleophilic counter ion; $0 \leq b1 \leq 0.3$; $0 \leq b2 \leq 0.3$; $0 \leq b3 \leq 0.3$; and $0 < b1+b2+b3 \leq 0.3$.

19. The patterning process according to claim 9, wherein the photosensitive resist composition contains any one or more of an organic solvent, a basic compound, a dissolution control agent, and a surfactant.

20. The patterning process according to claim 9, wherein the high energy beam is a KrF excimer laser having a wavelength of 248 nm, an ArF excimer laser having a wavelength of 193 nm, an electron beam, or a soft X-ray having a wavelength of 3 to 15 nm.

\* \* \* \* \*